United States Patent
Hoemann et al.

(10) Patent No.: US 7,148,209 B2
(45) Date of Patent: Dec. 12, 2006

(54) COMPOSITION AND METHOD FOR THE REPAIR AND REGENERATION OF CARTILAGE AND OTHER TISSUES

(75) Inventors: Caroline D. Hoemann, Montreal (CA); Michael D. Buschmann, Montreal (CA); Marc D. McKee, Westmount (CA)

(73) Assignee: Ecole Polytechnique, Montreal (CA)

( * ) Notice: Subject to any disclaimer, the term of this patent is extended or adjusted under 35 U.S.C. 154(b) by 26 days.

(21) Appl. No.: 11/031,325

(22) Filed: Jan. 7, 2005

(65) Prior Publication Data
US 2006/0029578 A1 Feb. 9, 2006

Related U.S. Application Data

(63) Continuation of application No. 09/896,912, filed on Jun. 29, 2001, now abandoned.

(60) Provisional application No. 60/214,717, filed on Jun. 29, 2000.

(51) Int. Cl.
| | |
|---|---|
| A01N 43/04 | (2006.01) |
| A01N 47/08 | (2006.01) |
| A61K 38/02 | (2006.01) |
| A61F 2/00 | (2006.01) |
| A61D 99/00 | (2006.01) |

(52) U.S. Cl. .................... 514/55; 514/12; 514/515; 424/422; 606/213

(58) Field of Classification Search ............ 514/55, 514/12, 515; 424/422; 606/213
See application file for complete search history.

(56) References Cited

U.S. PATENT DOCUMENTS 4,394,373 A 7/1983 Malette et al.

(Continued)

FOREIGN PATENT DOCUMENTS

EP 1 077 253 2/2001

(Continued)

OTHER PUBLICATIONS

W. Douglas Appling et al., "Synergistic enhancement of type I and III collagen production in cultured fibroblasts by transforming growth factor-β and ascorbate", *FEBS Letters*, 250(2):541-544, (Jul. 1989).

(Continued)

*Primary Examiner*—Jon Weber
*Assistant Examiner*—Rosanne Kosson
(74) *Attorney, Agent, or Firm*—Nixon Peabody LLP

(57) ABSTRACT

The present invention relates to a new method for repairing human or animal tissues such as cartilage, meniscus, ligament, tendon, bone, skin, cornea, periodontal tissues, abscesses, resected tumors, and ulcers. The method comprises the step of introducing into the tissue a temperature-dependent polymer gel composition such that the composition adhere to the tissue and promote support for cell proliferation for repairing the tissue. Other than a polymer, the composition preferably comprises a blood component such as whole blood, processed blood, venous blood, arterial blood, blood from bone, blood from bone-marrow, bone marrow, umbilical cord blood, placenta blood, erythrocytes, leukocytes, monocytes, platelets, fibrinogen, thrombin and platelet rich plasma. The present invention also relates to a new composition to be used with the method of the present invention.

44 Claims, 26 Drawing Sheets

U.S. PATENT DOCUMENTS

| | | |
|---|---|---|
| 4,956,350 A | 9/1990 | Mosbey |
| 5,368,051 A | 11/1994 | Dunn et al. |
| 5,468,787 A | 11/1995 | Braden et al. |
| 5,612,028 A | 3/1997 | Sackier et al. |
| 5,655,546 A | 8/1997 | Halpern |
| 5,709,854 A | 1/1998 | Griffith-Cima et al. |
| 5,723,331 A | 3/1998 | Tubo et al. |
| 5,736,372 A | 4/1998 | Vacanti et al. |
| 5,749,874 A | 5/1998 | Schwartz |
| 5,770,193 A | 6/1998 | Vacanti et al. |
| 5,770,417 A | 6/1998 | Vacanti et al. |
| 5,773,033 A | 6/1998 | Cochrum et al. |
| 5,811,094 A | 9/1998 | Caplan et al. |
| 5,837,235 A | 11/1998 | Mueller et al. |
| 5,842,477 A | 12/1998 | Naughton et al. |
| 5,855,619 A | 1/1999 | Caplan et al. |
| 5,866,415 A | 2/1999 | Villeneuve |
| 5,894,070 A | 4/1999 | Hansson et al. |
| 5,902,741 A | 5/1999 | Purchio et al. |
| 5,902,798 A | 5/1999 | Gouda et al. |
| 5,906,934 A | 5/1999 | Grande et al. |
| 5,908,784 A | 6/1999 | Johnstone et al. |
| 6,005,161 A | 12/1999 | Brekke et al. |
| 6,080,194 A | 6/2000 | Pachence et al. |
| 6,110,209 A | 8/2000 | Stone |
| 6,124,273 A | 9/2000 | Drohan et al. |
| 6,179,872 B1 | 1/2001 | Bell et al. |
| 6,200,606 B1 | 3/2001 | Peterson et al. |

FOREIGN PATENT DOCUMENTS

| | | |
|---|---|---|
| WO | WO 98/22114 | 5/1998 |
| WO | WO 99/07416 | 2/1999 |
| WO | WO 99/47186 | 9/1999 |
| WO | WO 00/02905 | 1/2000 |
| WO | WO 00/44413 | 8/2000 |
| WO | WO 00/48550 | 8/2000 |

OTHER PUBLICATIONS

Jayne E. Aston et al., "Repair of Articular Surfaces by Allografts of Articular and Growth-Plate Cartilage", *The Journal of Bone and Joint Surgery*, 68-B(1):29-35, (Jan. 1986).

G.A. Ateshian, "A Theoretical Formulation for Boundary Friction in Articular Cartilage", *Journal of Biomechanical Engineering*, 119:81-86, (Feb. 1997).

P.R. Austin et al., "Chitin: New Facets of Research", *Science*, 212:749-753, (May 15, 1981).

Francis F. Bartone et al., "Chitosan: Effects on Wound Healing in Urogenital Tissue: Preliminary Report", *The Journal of Urology*, 140:1134-1137, (1988).

George Bentley et al., "Homotransplantation of Isolated Epiphyseal and Articular Cartilage Chondrocytes in Joint Surfaces of Rabbits", *Nature*, 230:385-388, (Apr. 9, 1971).

Andreas Bernkop-Schnurch et al., "Intestianl Peptide and Protein Delivery: Novel Bioadhesive Drug-Carrier Matrix Shielding from Enzymatic Attack", *Journal of Pharmaceutical Sciences*, 87(4):430-434, (Apr. 1998).

Vladimir Bobic et al., "Articular Cartilage—To Repair or Not to Repair", *Annotation—The Journal of Bone and Joint Surgery*, 82-B(2):165-166, (Mar. 2000).

Howard A. Breinan et al., "Effect of Cultured Autologous Chondrocytes on Repair of Chondral Defects in a Canine Model", *The Journal of Bone and Joint Surgery, American Volume*, 79-A(10):1439-1451, (Oct. 1997).

Howard A. Breinan et al., "Healing of Canine Articular Cartilage Defects Treated with Microfracture, a Type-II Collagen Matrix, or Cultured Autologous Chondrocytes", *Journal of Orthopaedic Research*, 18(5):781-789, (2000).

Mats Brittberg et al., "A critical analysis of cartilage repair", *Acta Orthop Scand.*, 68(2):186-191, (1997).

Mats Brittberg et al., "Treatment of Deep Cartilage Defects in the Knee with Autologous Chondrocyte Transplantation", *The New England Journal of Medicine*, 331(14):889-895, (Oct. 6, 1994).

Mats Brittberg et al., "Rabbit Articular Cartilage Defects Treated With Autologous Cultured Chondrocytes", *Clinical Orthopaedics and Related Research*, 326:270-283, (1996).

J.A. Buckwalter et al., "Articular Cartilage Part II: Degeneration and Osteoarthrosis, Repair Regeneration, and Transplantation", *The Journal of Bone and Joint Surgery*, 79-A(4):612-632, (Apr. 1997).

Michael D. Buschmann et al., "Chondrocytes in Agarose Culture Synthesize a Mechanically Functional Extracellular Matrix", *Journal of Orthopaedic Research*, 10(6):745-757, (1992).

Miriam Butnariu-Ephrat et al., "Resurfacing of Goat Articular Cartilage by Chondrocytes Derived From Bone Marrow", *Clinical Orthopaedics and Related Research*, 330:234-243, (Sep. 1996).

Arnold I. Caplan et al., "Principles of Cartilage Repair and Regeneration", *Clinical Orthopaedics and Related Research*, 342:254-269, (1997).

Begoña Carreniño-Gómez et al., "Evaluation of the biological properties of soluble chitosan and chitosan microspheres", *International Journal of Pharmaceutics*, 148:231-240, (1997).

A. Chenite et al., "Novel injectable neutral solutions of chitosan form biodegradable gels in situ", *Biomaterials*, 21:2155-2161, (2000).

P.J. Chesterman et al., "Homotransplantation of Articular Cartilage and Isolated Chondrocytes", An experimental Study in Rabbits, *The Journal of Bone and Joint Surgery*), 50 B(1):184-197, (Feb. 1968).

J.C. Childers et al., "Partial Chondrectomy and Subchondral Bone Drilling for Chondromalacia", *Clinical Orthopaedics and Related Research*, 144:114-120, (Oct. 1979).

Yong-Woo Cho et al., "Water-soluble chitin as a wound healing accelerator", *Biomaterials*, 20:2139-2145, (1999).

Constance R. Chu et al., "Articular cartilage repair using allogeneic perichondrocyte-seeded biodegradable porous polylactic acid (PLA): A tissue-engineering study", *Journal of Biomedical Materials Research*, 29:1147-1154, (1995).

Constance R. Chu et al., "Osteochondral Repair Using Perichondrial Cells", A 1-Year Study In Rabbits, *Clinical Orthopaedics and Related Research*, 340:220-229, (1997).

Isaac Cohen et al., "Fibrin-Blood Platelet Interaction in a Contracting Clot", *British Journal of Haemotology*, 31:45-50, (1975).

Anne Denuziere et al., "Chitosan-chondroitin sulfate and chitosan-hyaluronate polyelectrolyte complexes: biological properties", *Biomaterials*, 19:1275-1285, (1998).

Anthony F. De Palma et al., "Process of Repair of Articular Cartilage Demonstrated by Histology and Autoradiography With Tritiated Thymidine", *Clinical Orthopaedics and Related Research*, 48:229-242, (Sep.-Oct. 1966).

George P. Dillon et al., "The influence of physical structure and charge on neurite extension in a 3D hydrogel scaffold", *J. Biomater Sci. Polymer Edn.*, 9(10):1049-1069, (1998).

A. Eser Elcin et al., "Neural tissue engineering: Adrenal chromaffin cell attachment and viability on chitosan scaffolds", *Neurological Research*, 20:648-654, (Oct. 1998).

Sally R. Frenkel et al., "Chondrocyte Transplantation Using a Collagen Bilayer Matrix for Cartilage Repair", *The Journal of Bone and Joint Surgery*, 79-B(5):831-836, (Sep. 1997).

L.E. Freed et al., "Joint resurfacing using allograft chondrocytes and synthetic biodegradable polymer scaffolds", *Journal of Biomedical Materials Research*, 28:891-899, (1994).

Tamo Fukamizo et al., "Chitosanase from *Streptomyces* sp. strain N174: a comparative review of its structure and function", *Biochem. Cell Biol*, 75:687-697, (1997).

Daniel A. Grande et al., "The Repair of Experimentally Produced Defects in Rabbit Articular Cartilage by Autologous Chondrocyte Transplantation", *Journal of Orthopaedic Research*, 7(2):208-218, (1989).

William T. Green, "Articular Cartilage Repair", Behavior of Rabbit Chondrocytes During Tissue Culture and Subsequent Allografting, *Clinical Orthopaedics and Related Research*, Section III, Basic Science and Pathology, 124:237-250, (May 1977).

L. Hangody et al., "Arthroscopic autogenous osteochondral mosaicplasty for the treatment of femoral condylar articular defects", A preliminary report, *Knee Surg. Sports Traumatol, Arthrosc.*, 5:262-267, (1997).
L. Hangody et al., "Treatment of Osteochondritis Dissecans of the Talus: Use of the Mosaicplasty Technique—A Preliminary Report", *Foot & Ankle International*, 18(10):628-634, (1997).
Dean A. Hendrickson et al., "Chondrocyte-Fibrin Matrix Transplants for Resurfacing Extensive Articular Cartilage Defects", *Journal of Orthopaedic Research*, 12(4):485-497, (1994).
Hidehiko Higaki et al., "Lubricating Ability of Langmuir-Blodgett Films as Boundary Lubricating Films on Articular Surfaces", *JSME International Journal*, Series C, 40(4):776-781, (1997).
George N. Homminga et al., "Repair of sheep articular cartilage defects with a rabbit costal perichondrial graft", *Acta Orthop. Scand.*, 62(5):415-418 (1991).
Ernst B. Hunziker et al., "Repair of Partial-Thickness Defects in Articular Cartilage: Cell Recruitment from the Synovial Membrane", *The Journal of Bone and Joint Surgery*, 78-A(5):721-733, (May 1996).
Anna Hyc et al., "Immunological Response Against Allogeneic Chondrocytes Transplanted Into Joint Surface Defects in Rats", *Cell Transplantation*, 6(2):119-124, (1997).
S. Itay et al., "Use of Cultured Embryonal Chick Epiphyseal Chondrocytes as Grafts for Defects in Chick Articular Cartilage", *Cartilage Repair by Cultured Chondrocytes*, 220:284-303, (Jul. 1987).
Lanny L. Johnson, "Arthroscopic Abrasion Arthroplasty", *Operative Arthorscopy*, Chapter 24, 341-360, (1991).
K. Jurgensen et al., "A New Biological Glue for Cartilage-Cartilage Interfaces: Tissue Transglutaminase", *The Journal of Bone and Joint Surgery*, 79-A(2):185-193, (Feb. 1997).
R.A. Kandel et al., "Transplantation of Cartilagenous Tissue Generated in Vitro into Articular Joint Defects", *Art. Cells, Blood Subs., and Immob. Biotech.*, 23(5):565-577, (1995).
Sadahito Kawamura et al., "Articular cartilage repair, Rabbit experiments with a collagen gel-biomatrix and chondrocytes cultured in it", *Acta Orthop. Scand.*, 69(1):56-62, (1998).
Martin U. Kopp et al., "Down-Regulation of Collagen XII in Transformed Mesenchymal Cells", *Int. J. Cancer*, 60:275-279, (1995).
Tomoe Koyano et al., "Attachment and growth of cultured fibroblast cells on PVA/chitosan-blended hydrogels", *J. Biomed. Mater. Res.*, Growth of Fibroblast Cells, 39:486-490, (1998).
Klaus E. Kuettner, "Biochemistry of Articular Cartilage in Health and Disease", *Clinical Biochemistry*, 25:155-163, (1992).
Ashkan Lahiji et al., "Chitosan supports the expression of extracellular matrix proteins in human osteoblasts and chondrocytes", *Matrix proteins in human osteoblasts*, pp. 586-595, (2000).
K.Y. Lee et al., "Preparation of chitosan self-aggregates as a gene delivery system", *Journal of controlled release*, 51:213-220, (1998).
Yong-Moo Lee et al., "Tissue Engineered Bone Formation Using Chitosan/Tricalcium Phosphate Sponges", *Periodontol.*, 71(3):410-417, (Mar. 2000).
Elizabeth A. Leistikow, "Platelet Internalization in Early Thrombogeneis", *Seminars in Thrombosis and Hemostasis*, 22(3):289-294, (1996).
Jian Xi Lu et al., "Effects of chitosan on rat knee cartilages", *Biomaterials*, 20:1937-1944, (1999).
M.N. Mahomed et al., "Allograft Bones and Soft Tissues, The Long-Term Success of Fresh, Small Fragment Osteochondral Allograft Used Intraarticular Post-Traumatic Defects in the Knee Joint", *Orthopedics*, Small Fragment Osetochondral Allografts, 15(10), 1191-1199, (Oct. 1992).
William G. Mallette et al., "Chitosan: A New Hemostatic", *The Annals of Thoracic Surgery*, 36(1):55-58, (Jul. 1983).
Henry J. Mankin, The Reaction of Articular Cartilage to Injury and Osteoarthritis (First of Two Parts), *The New England Journal of Medicine*, Medical Progress, pp. 1285-1293, (Dec. 12, 1974).
M. Mattioli-Belmonte et al., "N-N-dicarboxymethyl chitosan as delivery agent for bone morphogenetic protein in the repair of articular cartilage", *Medical & Biological Engineering & Computing*, 37:130-134, (1999).

Karola Messner et al., "Cartilage repair,", A critical review, *Acta Orthop. Scand.*, 67(5):523-529 (1996).
Tom Minas et al., Current Concepts in the Treatment of Articular Cartilage Defects, Orthopedics, pp. 525-537, (1997).
Riccardo A.A. Muzzarelli et al., "Depolymerization of chitosan and substituted chitosans with the aid of a wheat germ lipase preparation", *Enzyme Microb. Technol.*, 17:541-545, (Jun. 1995).
Riccardo A.A. Muzzarelli et al., "Role and fate of exogenous chitosans in human would tissues", *Eur. Chitin Soc.*, (1993).
R.A.A. Muzzarelli et al., "Stimulatory effect on bone formation exerted by a modified chitosan", *Biomaterials*, 15(13):1075-1081, (1994).
Robert S. Namba et al., "Spontaneous Repair of Superficial Defects in Articular Cartilage in a Fetal Lamb Model", *The Journal of Bone and Joint Surgery*, 80-A(1):4-10, (Jan. 1998).
Zvi Nevo et al., "The Manipulated Mesenchymal Stem Cells in Regenerated Skeletal Tissues", *Cell Transplantation*, 7(1):63-70, (1998).
Alan P. Newman, "Articular Cartilage Repair", *The American Journal of Sports Medicine*, 26(2):309-324, (1998).
Alan J. Nixon et al., "Enhanced Repair of Extensive Articular Defects by Insulin-like Growth Factor-I-laden Fibrin Composites", *Journal of Orthopaedic Research*, 17(4):475-487, (1999).
Takashi Noguchi et al., "Repair of Osteochondral Defects With Grafts of Cultured Chondrocytes", *Clinical Orthopaedics and Related Research*, 302:251-258, (May 1994).
Shawn W. O'Driscoll et al., "Chondrogenesis in Periosteal Explants", *The Journal of Bone and Joint Surgery*, 76-A(7):1042-1051, (Jul. 1994).
Shawn W. O'Driscoll et al., "Durability of Regenerated Articular Cartilage Produced by Free Autogenous Periosteal Grafts in Major Full-Thickness Defects in Joint Surfaces under the Influence of Continuous Passive Motion", *The Journal of Bone and Joint Surgery*, 70-A(4):595-606, (Apr. 1988).
Yoshiharu Okamoto et al., "Evaluation of Chitin and Chitosan on Open Wound Healing in Dogs", pp. 851-854, (1995).
H.K. Outerbridge et al., "The Use of a Lateral Patellar Autologous Graft for the Repair of a Large Osteochondral Defect in the Knee", *The Journal of Bone and Joint Surgery*, 77-A(1):65-72, (Jan. 1995).
George A. Paletta et al., "The repair of osteochondral defects using an exogenous fibrin clot", *The American Journal of Sports Medicine*, 20(6):725-731, (1992).
D.G. Pechak et al., "Morphology of Bone Development and Bone Remodeling in Embryonic Chick Limbs", *Bone*, 7:459-472, (1986).
Gianfranco Peluso et al., "Chitosan-mediated stimulation of macrophage function", *Biomaterials*, 15(15):1215-1220, (1994).
K.H. Pridie, "A method of resurfacing osteoarthritic knee joints", *The Journal of Bone and Joint Surgery*, 41-B(3):618-619, (Aug. 1959).
S. Bhaskara Rao et al., "Use of chitosan as a biomaterial: Studies on its safety and hemostatic potential", *Journal of Biomedical Materials Research*, 34:21-28, (1997).
Dror Robinson et al., "Regenerating Hyaline Cartilage in Articular Defects of Old Chickens Using Implants of Embryonal Chick Chondrocytes Embedded in a New Natural Delivery Substance", *Calcif Tissue Int.*, 46:246-253, (1990).
Juan J. Rodrigo et al., "Osteoarticular Injuries of the Knee", *Operative Orthopaedics*, Second Edition, pp. 2077-2082, (1993).
Kenneth N. Sall et al., "The Effect of Chitosan on Corneal Wound Healing", *Ann Ophtalmol.*, 19:31-33, (1987).
Andrew E. Sams et al., "Chondrocyte-laden collagen scaffolds for resurfacing extensive articular cartilage defects", *Osteoarthritis and Cartilage*, 3(1):47-59, (1995).
Nicolaas G.M. Schipper et al., "Chitosans as Absorption Enhancers for Poorly Absorbable Drugs 2: Mechanism of Absorption Enhancement", *Pharmaceutical Research*, 14(7):923-929, (1997).
I.M. Schwarz et al., "Surface-Active Phospholipid as the Lubricating Component of Lubricin", *British Journal of Rheumatology*, 37(1):21-26, (1998).
V. Franklin Sechriest et al., "GAG-augmented polysaccharide hydrogel: A novel biocompatible and biodegradable material to support chondrogeneis", pp. 534-541, (2000).

Rani S. Sellers et al., "The Effect of Recombinant Human Bone Morphogenetic Protein-2 (rhBMP-2) on the Healing of Full-Thickness Defects of Articular Cartilage", *The Journal of Bone and Joint Surgery*, 79-A(10):1452-1463, (Oct. 1997).

Rani S. Sellers et al., "Repair of Articular Cartilage Defects One Year After Treatment with Recombinant Human Bone Morphogenetic Protein-2 (rhBMP-2)", *The Journal of Bone and Joint Surgery, American Volume*, 82-A(2):151-160, (Feb. 2000).

Pierre Shephard et al., "Studies on the bone morphogenetic protein type II receptor and its ligands in would healing", *XVIIth FECTS Meeting*, Abstract Form, (2000).

Yoshihiro Shigemasa et al., "Applications of Chitin and Chitosan for Biomaterials", *Biotechnology and Genetic Engineering Reviews*, 13:383-420, (Dec. 1995).

J. Soulhat et al., "A Fibril-Network-Reinforced Biphasic Model of Cartilage in Unconfined Compression", *Journal of Biomechanical Engineering*, 121:340-347, (Jun. 1999).

Nicola Specchia et al., "Fetal chondral homografts in the repair of articular cartilage defects", *Bulletin Hospital for Joint Diseases*, 54(4):230-235, (1996).

J.R. Steadman et al., "The microfracture procedure: Rationale, technique, and clinical observations for treatment of articular cartilage defects", *J. Sports Traumatol. rel. res.*, 20(2):61-70, (1998).

C.A. Stone et al., "Healing at skin graft donor sites dressed with chitosan", *British Journal of Plastic Surgery*, 53:601-606, (2000).

J.-K. Francis Suh et al., "Application of chitosan-based polysaccharaide biomaterials in cartilage tissue engineering: a review", *Biomaterials*, 21:2589-2598, (2000).

M. Terbojevich et al., "Molecular parameters of chitosans depolymerized with the aid of papain", *Carbohydrate Polymers*, 29(1):63-68, (1996).

Hiroshi Ueno et al., "Accelerating effects of chitosan for healing at early phase of experimental open wound in dogs", *Biomaterials*, 20:1407-1414, (1999).

G.W. Vasios et al., "Chitotriosidase is Expressed in Normal Chondrocytes and is Upregulated in Chondrocytes Derived from Osteoarthritic Cartilage", 45th Annual Meeting, Orthopaedic research Society, p. 711, (Feb. 1-4, 1999).

Shigeyuki Wakitani et al., "Repair of Rabbit Articular Surfaces with Allograft Chondrocytes Embedded in Collagen Gel", *The Journal of Bone and Joint Surgery*, 71-B(1):74-80, (Jan. 1989).

Shigeyuki Wakitani et al., "Mesenchymal Cell-Based Repair of Large, Full-Thickness Defects of Articular Cartilage", *The Journal of Bone and Joint Surgery*, 76-A(4):579-592, (Apr. 1994).

Xiaochun Wei et al., "Maturation-dependent repair of untreated osteochondral defects in the rabbit knee joint", *Journal of Biomedical Materials Research*, 34:63-72, (1997).

Kiyohito Yagi et al., "Effectiveness of Fuctose-Modified Chitosan as a Scaffold for Hepatocyte Attachment", *Biol. Pharm. Bull.*, 20(12):1290-1294, (1997).

C. Zoppou et al., Dynamics of Human Milk Extraction: A Comparative Study of Breast Feeding and Breast Pumping, *Bulletin of Mathematical Biology*, 59(5):953-973, (1997).

Arnoczky, S.P., R.F. Warren and J. M. Spivak. 1988. "Meniscal repair using an exogenous fibrin clot. An experimental study in dogs." *J. Bone Joint Sug Am* 70, No. 8, p. 1209-17.

Clark, Richard A.F. 1996. *The molecular and cellular biology of wound repair*. 2 ed. New York: Plenum.

Hall, B.K. 1983. Cartilage. New York, NY: Academic Press.

Insall, J.N. 1967. Intra-articular surgery for degenerative arthritis of the knee. A report of the work of the late K.H. Pridie. *J. Bone Joint Surg Br* 49, No. 2, p. 211-28.

Inui, H., M. Tsujikubo, S. Hirano. 1995. "Low molecular weight chitosan stimulation of mitogenic response to platelet-drived growth factor in vasuclar smooth muscle cells." *Biosci Biotechnol Biochem*, v. 59, p. 211-4.

McCarthy, D.J. and W.J. Koopman. 1993. "Arthritis and allied conditions. A textbook of rheumatology." *Philadelphia: Lea and Febiger*.

Sashiwa, H., H. Saimoto, Y. Shigemasa, R. Ogawa and S. Tokura. 1990. "Lysozyme susceptibility of partially deacetylated chitin." *International Journal of Biological Macromolecules* 12, No. 5, p. 295-6.

Yalpani, M and D. Pantaleone. 1994. "An examination of the unusual suceptbilities of aminoglycans to enzymatic hydrolysis." *Carbohydrate Research* 256, No. 1, p. 159-75.

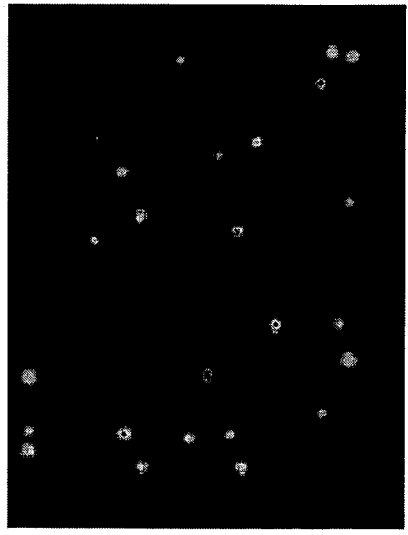
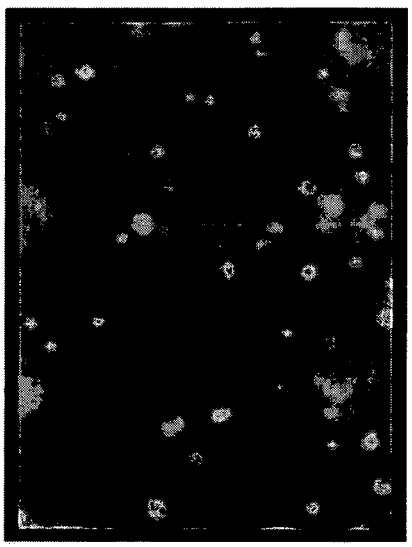
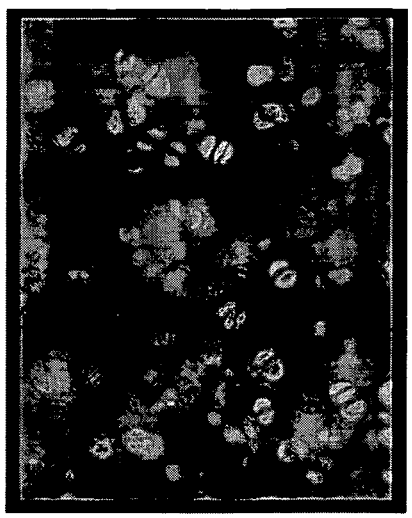
FIG. 2A
FIG. 2B
FIG. 2C

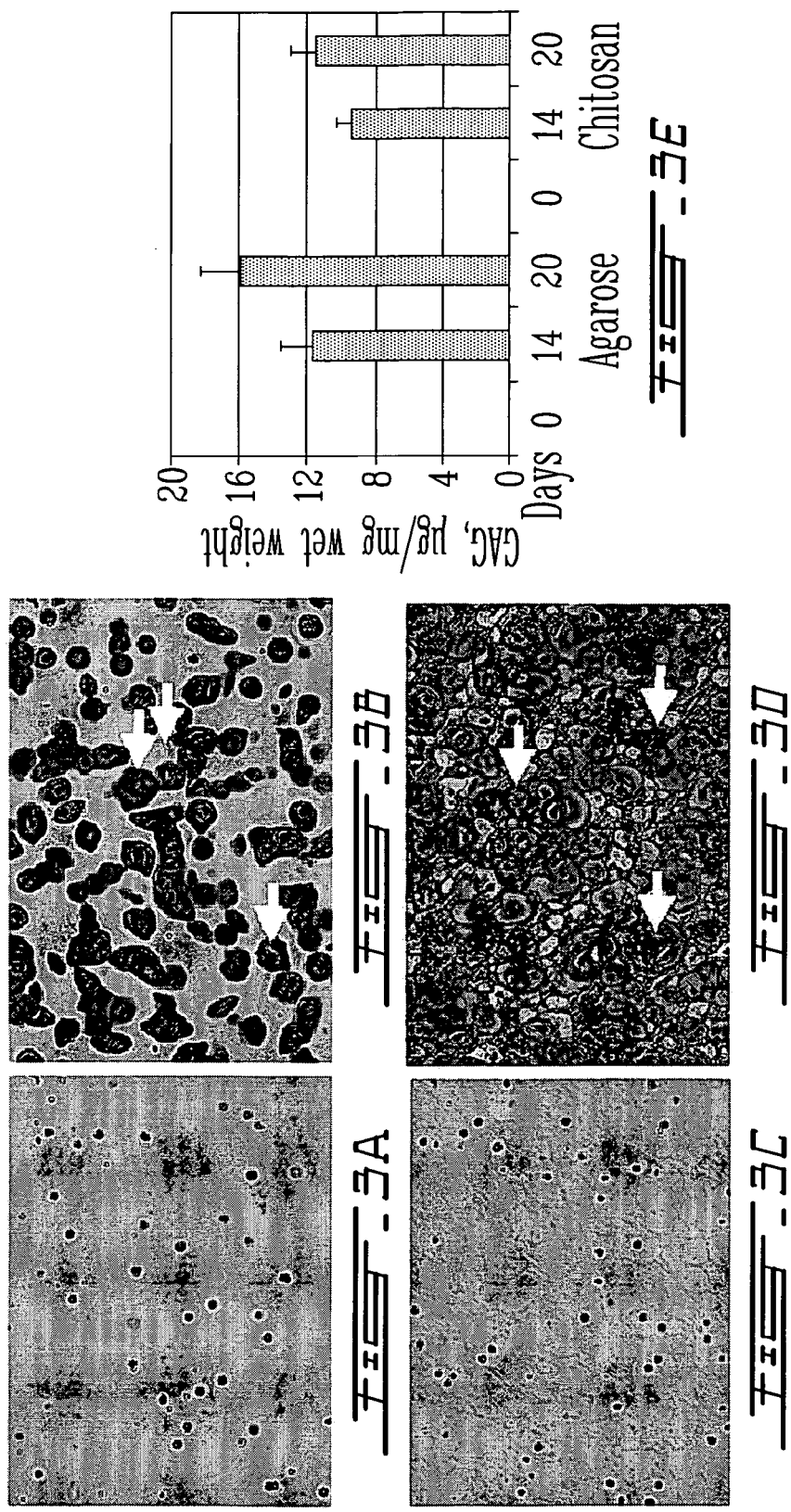

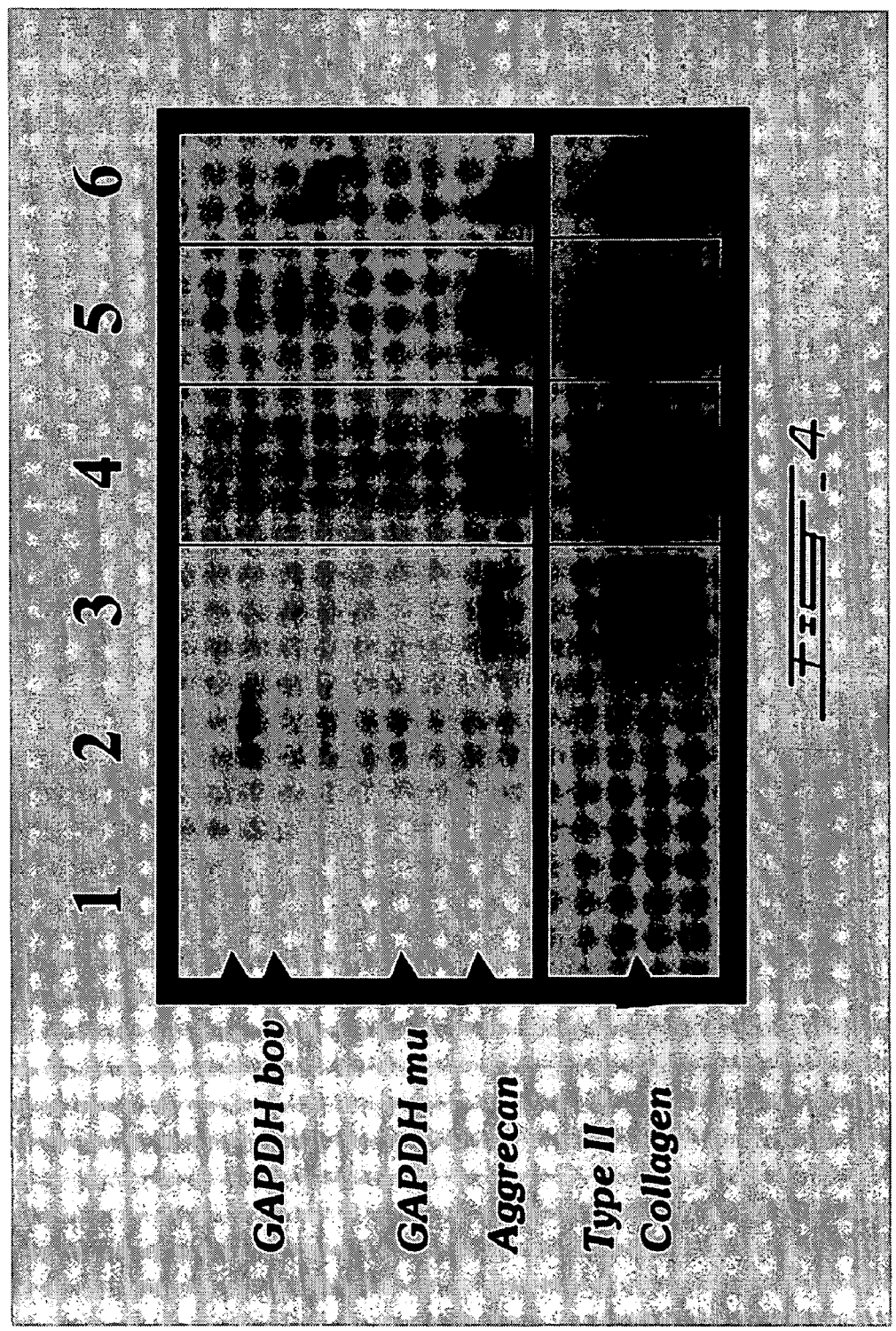

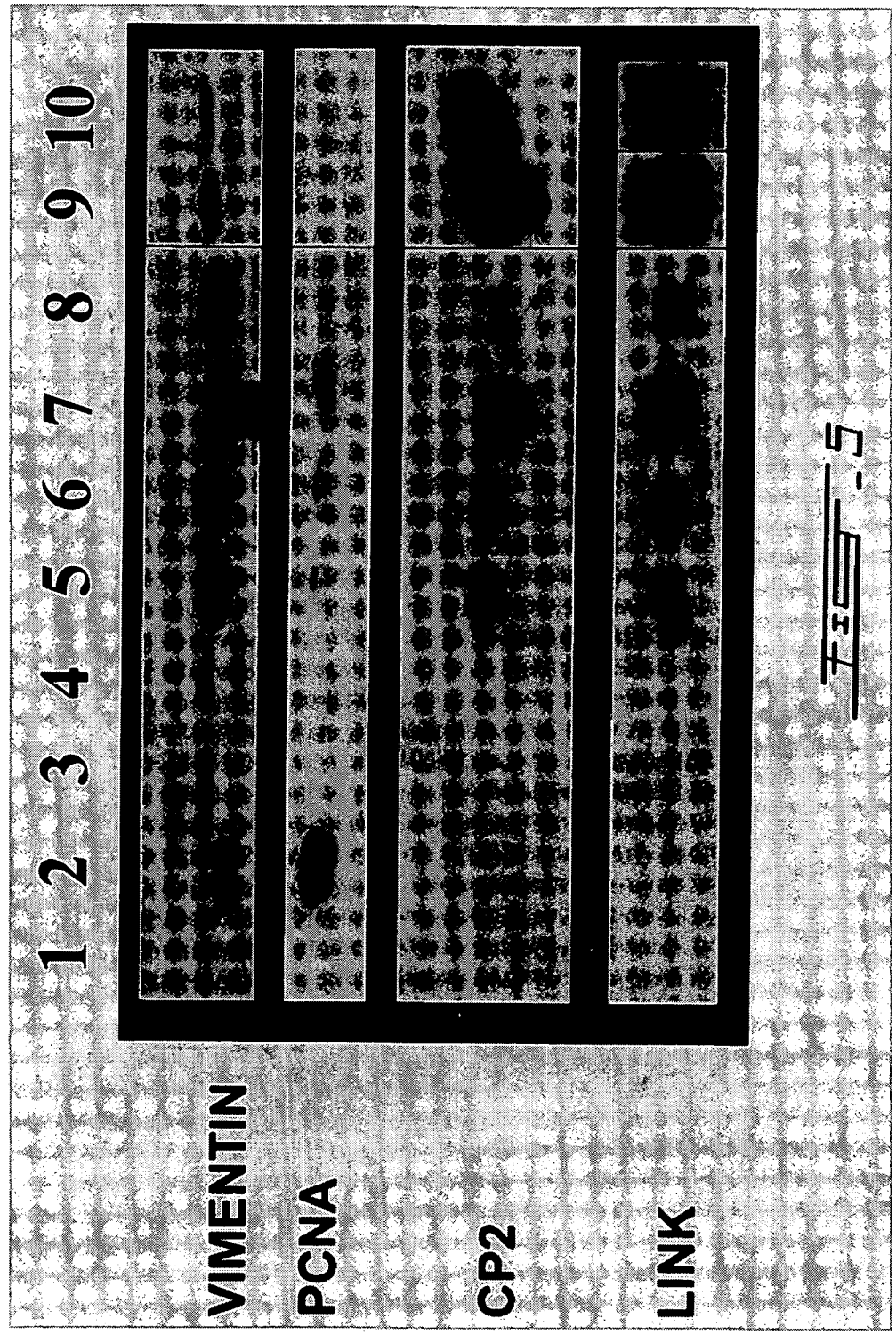

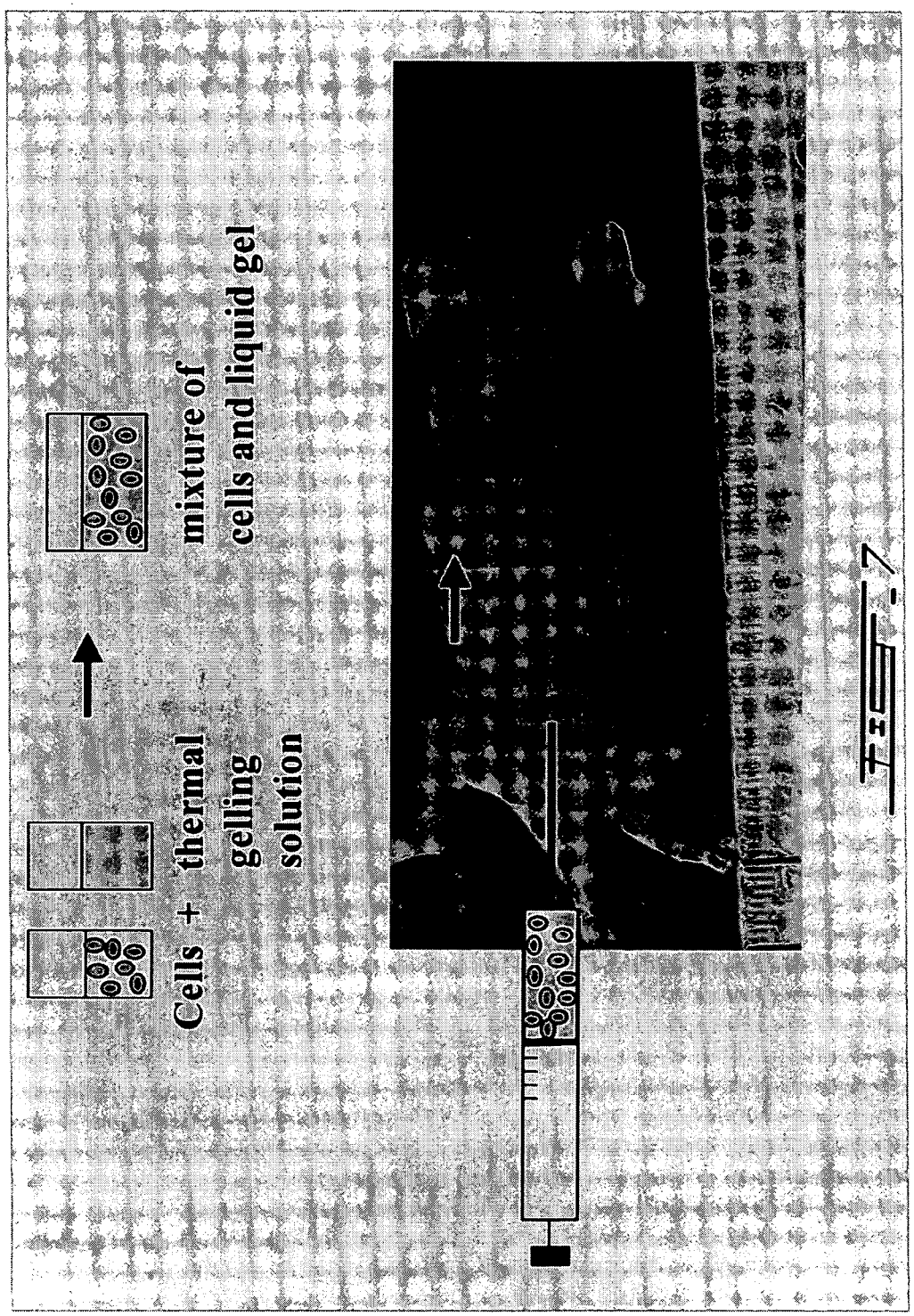

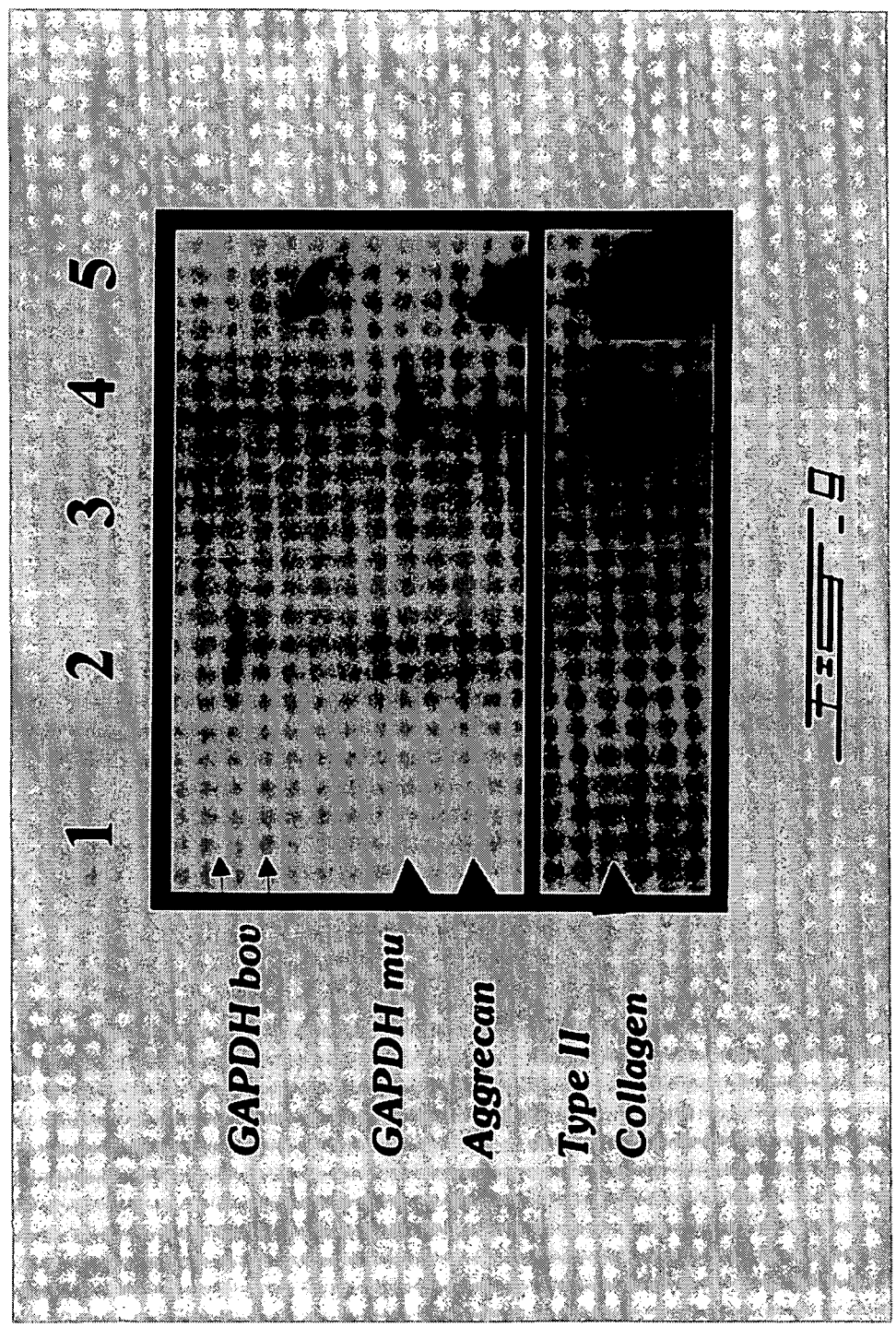

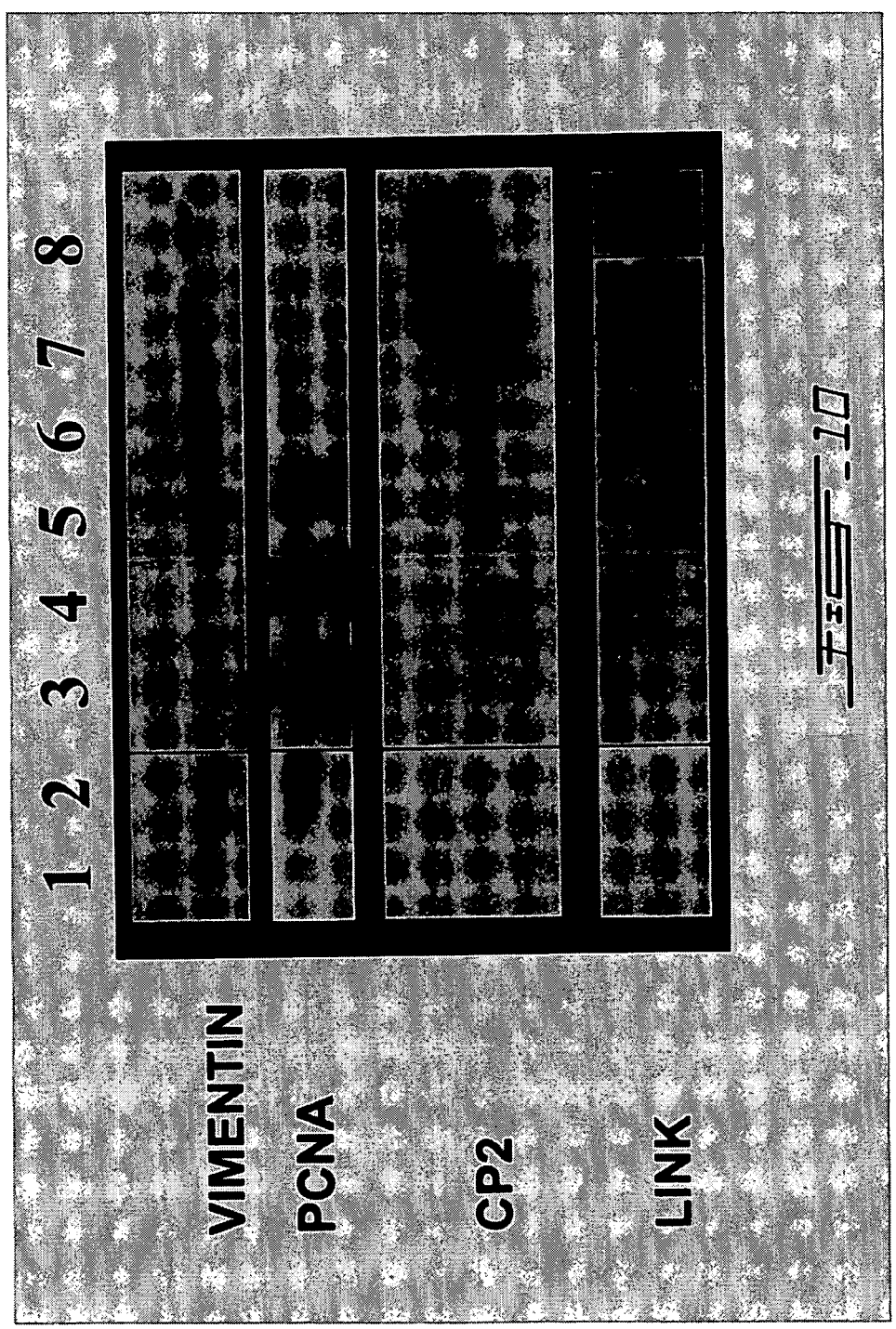

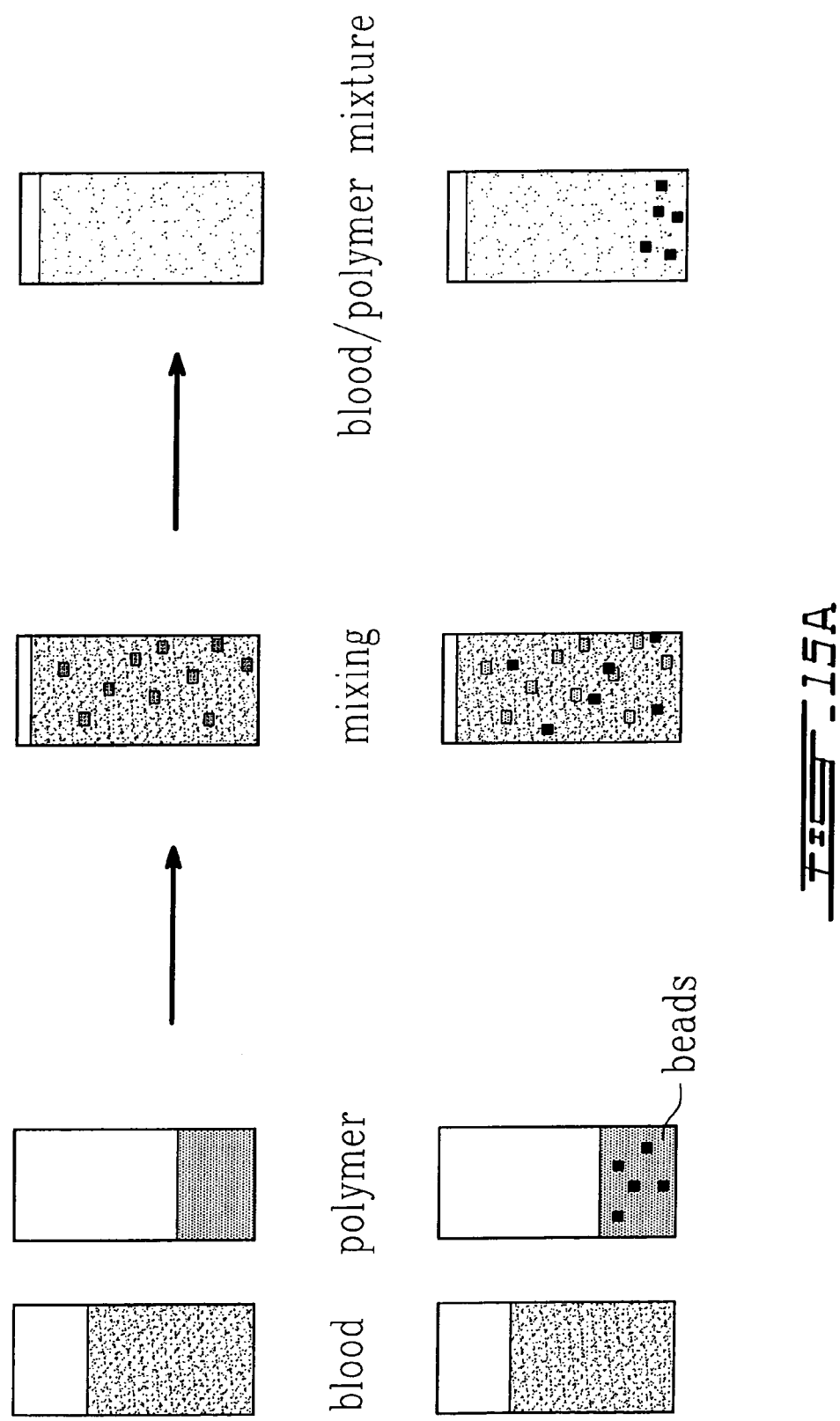

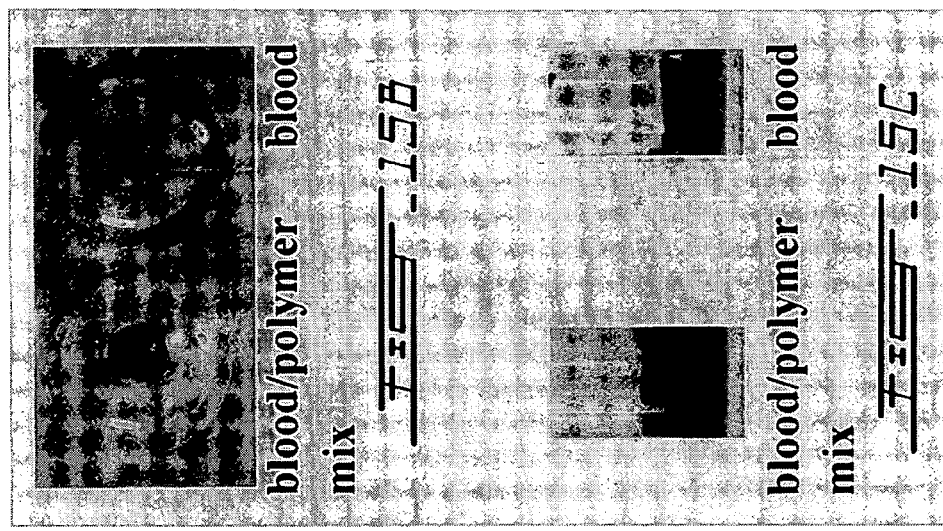

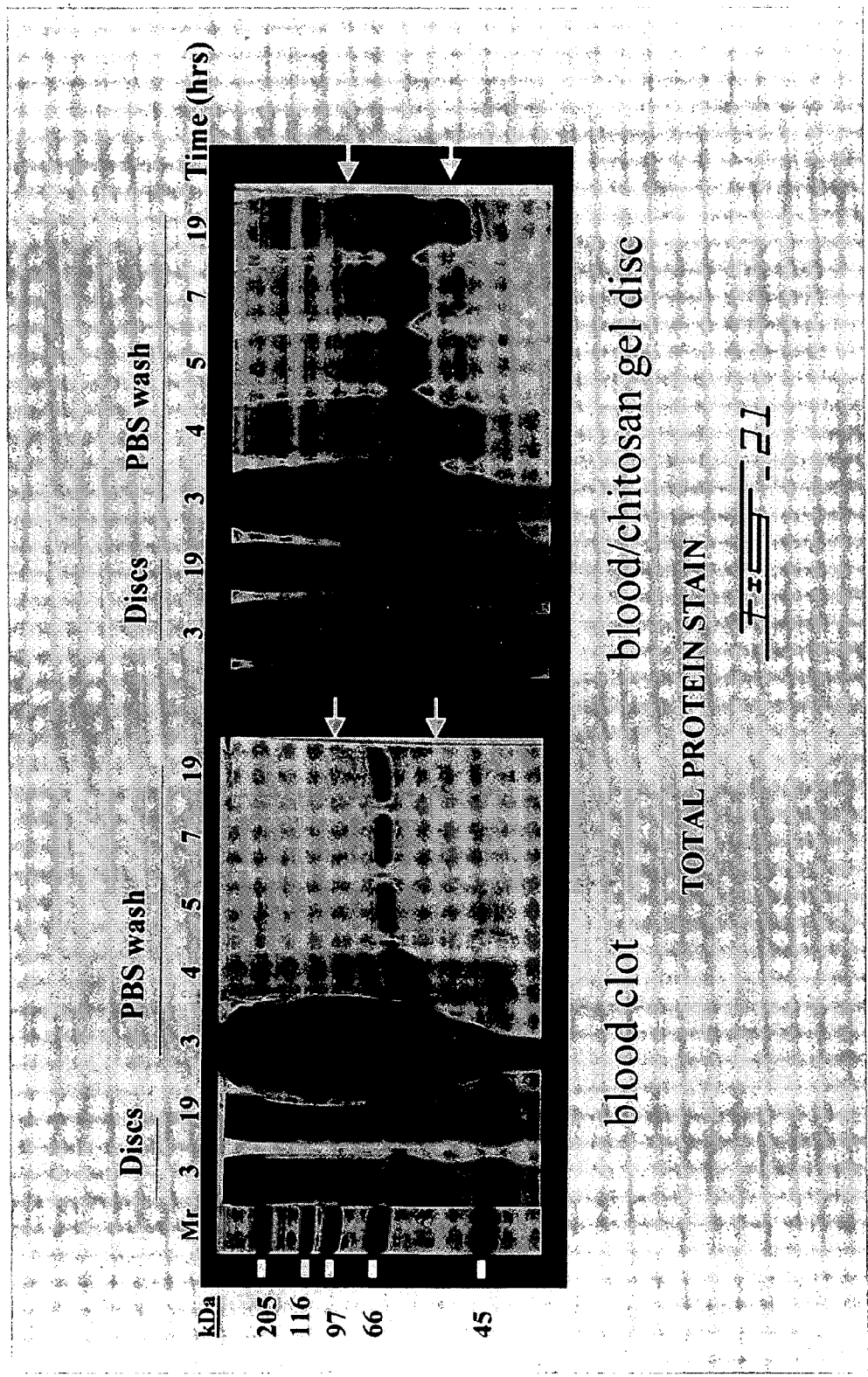

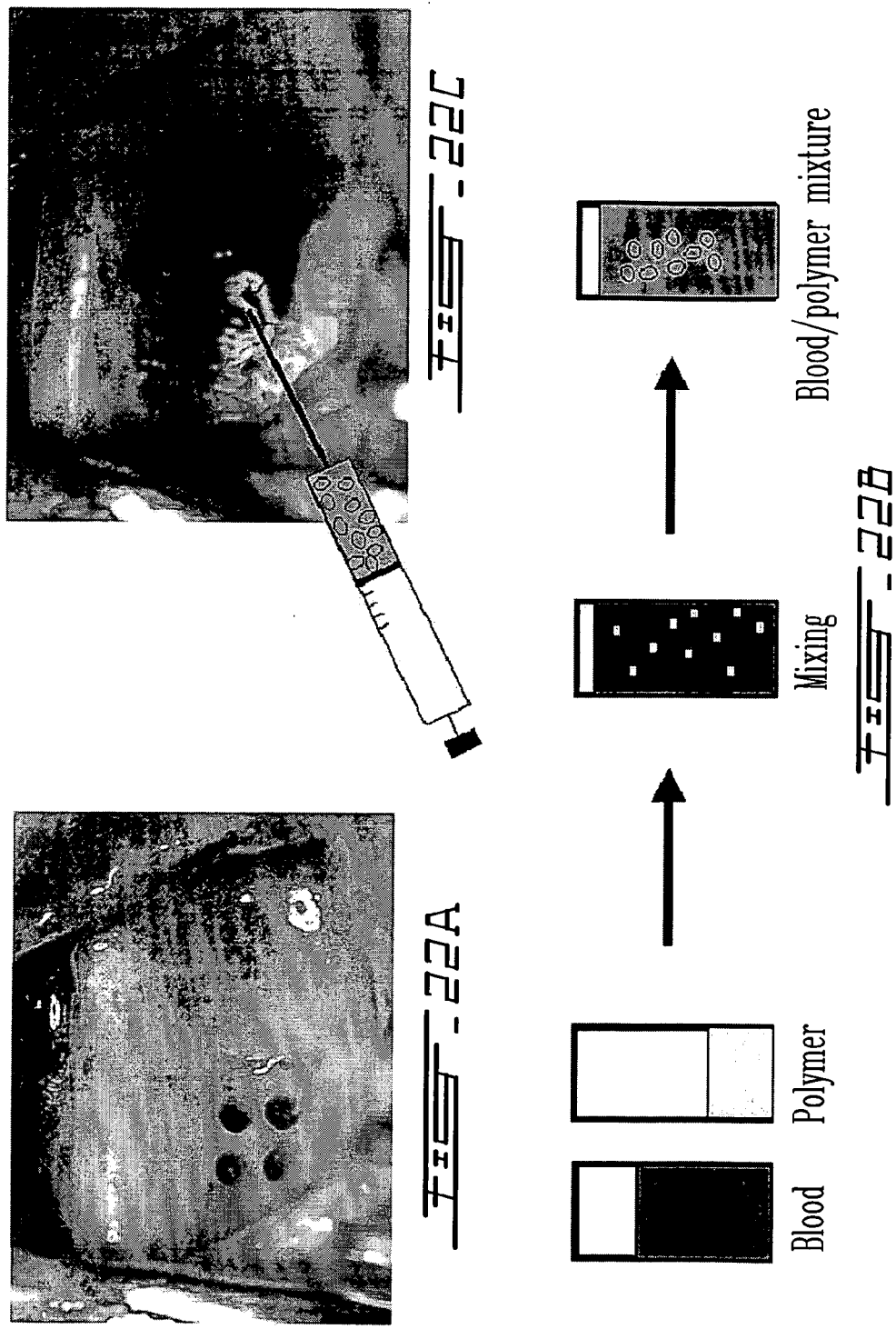

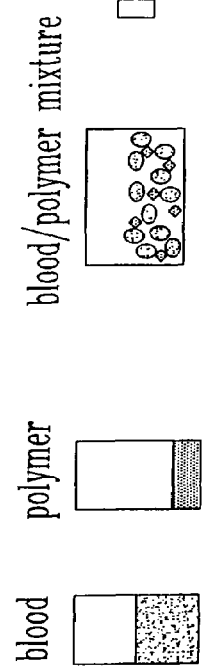

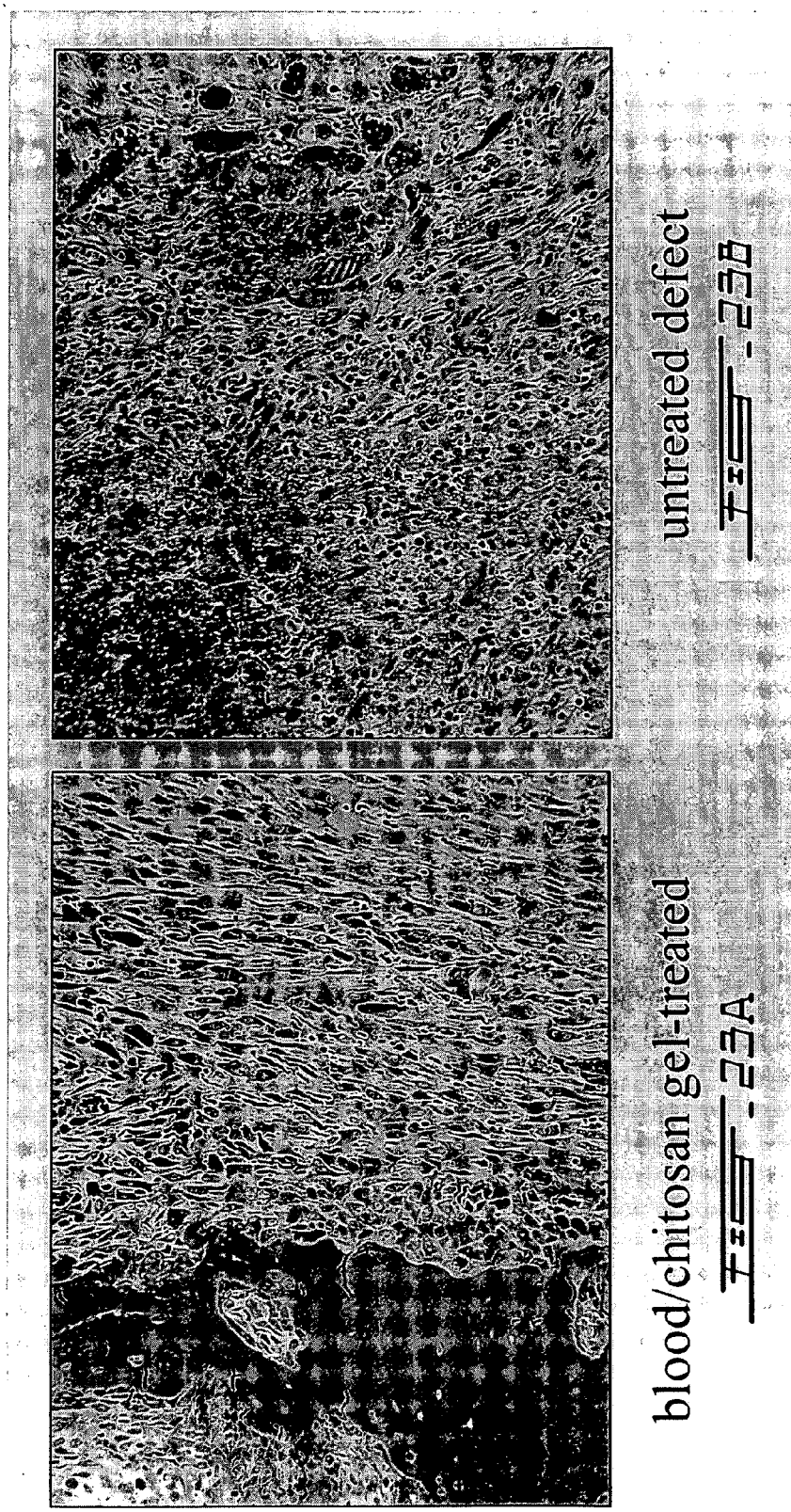
FIG. 23A blood/chitosan gel-treated
FIG. 23B untreated defect

Untreated defect

Blood/chitosan gel-treated

COMPOSITION AND METHOD FOR THE REPAIR AND REGENERATION OF CARTILAGE AND OTHER TISSUES

CROSS-REFERENCE TO RELATED APPLICATIONS

This application is a continuation of U.S. Ser. No. 09/896,912 filed Jun. 29, 2001 now abandoned, which claims the benefit under 35 U.S.C. § 119(e) of United States Provisional Application Nos. 60/214,717 filed Jun. 29, 2000.

BACKGROUND OF THE INVENTION (a) Field of the Invention

The invention relates to a composition and method of application to improve the repair and to regenerate cartilaginous tissues and other tissues including without limitation meniscus, ligament, tendon, bone, skin, cornea, periodontal tissues, abscesses, resected tumors, and ulcers.

(b) Description of Prior Art

1) The Cartilage Repair Problem:

Cartilage: Structure, Function, Development, Pathology

Articular cartilage covers the ends of bones in diarthroidial joints in order to distribute the forces of locomotion to underlying bone structures while simultaneously providing nearly frictionless articulating interfaces. These properties are furnished by the extracellular matrix composed of collagen types II and other minor collagen components and a high content of the proteoglycan aggrecan. In general, the fibrillar collagenous network resists tensile and shear forces while the highly charged aggrecan resists compression and interstitial fluid flow. The low friction properties are the result of a special molecular composition of the articular surface and of the synovial fluid as well as exudation of interstitial fluid during loading onto the articular surface (Ateshian, 1997; Higaki et al., 1997; Schwartz and Hills, 1998).

Articular cartilage is formed during the development of long bones following the condensation of prechondrocytic mesenchymal cells and induction of a phenotype switch from predominantly collagen type I to collagen type II and aggrecan (Hall, 1983; Pechak et al., 1986). Bone is formed from cartilage when chondrocytes hypertrophy and switch to type X collagen expression, accompanied by blood vessel invasion, matrix calcification, the appearance of osteoblasts and bone matrix production. In the adult, a thin layer of articular cartilage remains on the ends of bones and is sustained by chondrocytes through synthesis, assembly and turnover of extracellular matrix (Kuettner, 1992). Articular cartilage disease arises when fractures occur due to physical trauma or when a more gradual erosion, as is characteristic of many forms of arthritis, exposes subchondral bone to create symptomatic joint pain (McCarty and Koopman, 1993). In addition to articular cartilage, cartilaginous tissues remain in the adult at several body sites such as the ears and nose, areas that are often subject to reconstructive surgery.

2) Cartilage Repair: The Natural Response

Articular cartilage has a limited response to injury in the adult mainly due to a lack of vascularisation and the presence of a dense proteoglycan rich extracellular matrix (Newman, 1998; Buckwalter and Mankin, 1997; Minas and Nehrer, 1997). The former inhibits the appearance of inflammatory and pluripotential repair cells, while the latter emprisons resident chondrocytes in a matrix non-conducive to migration. However, lesions that penetrate the subchondral bone create a conduit to the highly vascular bone allowing for the formation of a fibrin clot that traps cells of bone and marrow origin in the lesion leading to a granulation tissue. The deeper portions of the granulation tissue reconstitute the subchondral bone plate while the upper portion transforms into a fibrocartilagenous repair tissue. This tissue can temporarily possess the histological appearance of hyaline cartilage although not its mechanical properties (Wei et al., 1997) and is therefore unable to withstand the local mechanical environment leading to the appearance of degeneration before the end of the first year post-injury. Thus the natural response to repair in adult articular cartilage is that partial thickness lesions have no repair response (other than cartilage flow and localized chondrocyte cloning) while full-thickness lesions with bone penetration display a limited and failed response. Age, however, is an important factor since full thickness lesions in immature articular cartilage heal better than in the adult (DePalma et al., 1966; Wei et al., 1997) and superficial lacerations in fetal articular cartilage heal completely in one month without any involvement of vasculature or bone-derived cells (Namba et al., 1998).

3) Current Approaches for Assisted Cartilage Repair

Current clinical treatments for symptomatic cartilage defects involve techniques aimed at: 1) removing surface irregularities by shaving and debridement 2) penetration of subchondral bone by drilling, fracturing or abrasion to augment the natural repair response described above (i.e. the family of bone-marrow stimulation techniques) 3) joint realignment or osteotomy to use remaining cartilage for articulation 4) pharmacological modulation 5) tissue transplantation and 6) cell transplantation (Newman, 1998; Buckwalter and Mankin, 1997). Most of these methods have been shown to have some short term benefit in reducing symptoms (months to a few years), while none have been able to consistently demonstrate successful repair of articular lesions after the first few years. The bone marrow-stimulation techniques of shaving, debridement, drilling, fracturing and abrasion athroplasty permit temporary relief from symptoms but produce a sub-functional fibrocartilagenous tissue that is eventually degraded. Pharmacological modulation supplying growth factors to defect sites can augment natural repair but to date insufficiently so (Hunziker and Rosenberg, 1996; Sellers et al., 1997). Allograft and autograft osteochondral tissue transplants containing viable chondrocytes can effect a more successful repair but suffer from severe donor limitations (Mahomed et al., 1992; Outerbridge et al., 1995).

4) Bone-Marrow Stimulation

The family of bone marrow-stimulation techniques include debridement, shaving, drilling, microfracturing and abrasion arthroplasty. They are currently used extensively in orthopaedic clinical practice for the treatment of focal lesions of articular cartilage that are full-thickness, i.e. reaching the subchondral bone, and are limited in size, typically less than 3 cm² in area. Use of these procedures was initiated by Pridie and others (Pridie, 1959; Insall, 1967; DePalma et al., 1966) who reasoned that a blood clot could be formed in the region of an articular cartilage lesion by violating the cartilage/bone interface to induce bleeding from the bone into the cartilage defect that is avascular. This hematoma could then initiate the classical cascade of wound healing events that leads to successful healing or at least scarring in wounds of vascularized tissues (Clark, 1996). Variations of the Pridie drilling technique were proposed later including abrasion arthroplasty (Childers and Ellwood, 1979; Johnson, 1991) and microfracturing (Rodrigo et al., 1993; Steadman et al., 1997). Abrasion arthroplasty uses motorised instruments to grind away abnormally dense subchondral bone to reach a blood supply in the softer deeper bone. The microfracture technique uses a pick, or an awl, to pierce the subchondral bone plate deep enough (typically 3–4 mm), again to reach a vascular supply and create a blood clot inside the cartilage lesion. Practitioners of the microfracture technique claim to observe a higher success rate than drilling due to the lack of any heat-induced necrosis and less biomechanical destabilisation of the subchondral bone plate with numerous smaller fracture holes rather than large gaps in the plate producing by drilling (Steadman et al., 1998). Yet another related technique for treating focal lesions of articular cartilage is mosaicplasty or osteochondral autograft transplantation (OATS) where cartilage/bone cylinders are transferred from a peripheral "unused" region of a joint to the highly loaded region containing the cartilage lesion (Hangody et al., 1997).

There is no universal consensus among orthopaedists on which type of articular cartilage lesion should receive which type of treatment. There is also a lack of rigorous scientific studies that demonstrate the efficacy of these treatments for particular indications. Thus the choice of treatment for cartilage lesions is largely dependent on the training, inclinations and personal experience of the practitioner. Reasons for this lack of consensus are multifold but include the variability in the type of lesion treated and a variable if not uncontrolled success in the formation of a "good quality" blood clot. Some of the problems associated with forming a good quality blood clot with these procedures are 1) the uncontrolled nature of the bleeding coming from the bone, which never fills up the cartilage lesion entirely 2) platelet mediated clot contraction occurring within minutes of clot formation reduces clot size and could detach it from surrounding cartilage (Cohen et al., 1975) 3) dilution of the bone blood with synovial fluid or circulating arthroscopy fluid and 4) the fibrinolytic or clot dissolving activity of synovial fluid (Mankin, 1974). Some of these issues were the motivation behind some studies where a blood clot was formed ex vivo and then cut to size and packed into a meniscal defect (Arnoczky et al., 1988) or an osteochondral defect (Palette et al., 1992). Something similar to the classical wound healing cascade then ensued to aid healing of the defect. This approach did clearly provide more filling of the defect with repair tissue, however the quality of the repair tissue was generally not acceptable, being predominantly fibrous and mechanically insufficient. Some probable reasons for a less than satisfactory repair tissue with this approach are 1) continued platelet mediated clot contraction 2) the lack of viability of some blood components due to extensive ex vivo manipulation and 3) the solidification of the clot ex vivo which precludes good adhesion to all tissue surfaces surrounding the cartilage defect and limits defect filling. In summary, current clinical procedures practised by orthopaedists for treating focal lesions of articular cartilage mostly depend on the formation of a blood clot within the lesion. However the ability to form a good quality blood clot that fills the lesion and contains all of the appropriate elements for wound healing (platelets, monocytes, fibrin network etc) in a viable state produces inconsistent and often unsatisfactory outcomes. One of the embodiments of the present invention ameliorates this situation by providing a composition and method for delivering these blood borne wound healing elements in a full-volume non-contracting matrix to an articular cartilage lesion.

5) Biomaterials and Growth Factors

Several experimental techniques have been proposed to repair cartilage lesions using biomaterials and growth factors, sometimes each alone but often in combination. The analogy with the above-described family of bone-marrow stimulation techniques is clear. The fibrin scaffold of the blood clot could be replaced with a prefabricated biomaterial scaffold and the natural mitogenic and chemotactic factors in the blood clot could be replaced with user-controlled quantities and species of soluble elements such as recombinant growth factors. Examples of this approach include the use of fibrin glues to deliver recombinant proteins such as insulin-like-growth factors (Nixon et al., 1999) and transforming growth factors (Hunziker and Rosenberg, 1996). Other biologics have been combined with generic biomaterials such as polylactic acid (PLA), polyglycolic acid (PGA), collagen matrices and fibrin glues including bone morphogenetic proteins (Sellers et al., 1997; Sellers, 2000; Zhang et al. Patent WO 00/44413, 2000), angiotensin-like peptides (Rodgers and Dizerega, Patent WO 00/02905, 2000), and extracts of bone containing a multiplicity of proteins called bone proteins or BP (Atkinson, Patent WO 00/48550, 2000). In the latter method, BP soaked collagen sponges needed to be held in the cartilage defect using an additional fibrin/thrombin based adhesive, creating a rather complex and difficult to reproduce wound healing environment. Coating the biomaterial with fibronectin or RGD peptides to aid cell adhesion and cell migration has been done (Breckke and Coutts, U.S. Pat. No. 6,005,161, 1999). Some previous methods have combined bone-marrow stimulation with post-surgical injection of growth hormone in the synovial space with limited success (Dunn and Dunn, U.S. Pat. No. 5,368,051, 1994). Specific biomaterials compositions have also been proposed such as mixtures of collagen, chitosan and glycoaminoglycans (Collombel et al., U.S. Pat. No. 5,166,187, 1992; Suh et al., Patent WO 99/47286, 1999), a crushed cartilage and bone paste (Stone, U.S. Pat. No. 6,110,209, 2000), a multicomponent collagen-based construct (Pahcence et al., U.S. Pat. No. 6,080,194, 2000) and a curable chemically reactive methacrylate-based resin (Braden et al., U.S. Pat. No. 5,468,787, 1995). None of these approaches has reached the clinic due to their inability to overcome some of the following problems 1) lack of retention and adherence of the biomaterial in the cartilage defect 2) lack of sustained release of active forms of these molecules at effective concentrations over prolonged periods of time 3) multiple and uncontrolled biological activities of the delivered molecules 4) cytotoxicity of acidic degradation products of PGA and PLA 5) inappropriate degradation kinetics or immunogencity of the carrier biomaterial and 6) undesirable systemic or ectopic affects (calcification of organs) of the active biologics. The successful implementation of these approaches awaits the solution to some or all of these issues.

6) Cell Transplantation

Techniques involving cell transplantation have provoked much recent interest due to their ability to enhance cartilage repair by introducing into articular defects, after ex vivo passaging and manipulation, large numbers of autologous chondrocytes (Grande et al., 1989; Brittberg et al., 1994 and 1996; Breinan et al., 1997), allogenic chondrocytes (Chesterman and Smith, 1968; Bently and Greer, 1971; Green, 1977; Aston and Bently, 1986; Itay et al., 1987; Wakatini et al., 1989; Robinson et al., 1990; Freed et al., 1994; Noguchi et al., 1994; Hendrickson et al., 1994; Kandel et al., 1995; Sams and Nixon, 1995; Specchia et al., 1996; Frankel et al., 1997; Hyc et al. 1997; Kawamura et al., 1998), xenogenic chondrocytes (Homminga et al., 1991), perichondrial cells (Chu et al., 1995; Chu et al., 1997), or autogenic and allogenic bone marrow-derived mesenchymal stem cells (Wakatini et al., 1994; Butnariu-Ephrat, 1996; Caplan et al., 1997; Nevo et al., 1998). The cell transplantation approach possesses some potential advantages over other cartilage repair techniques in that they 1) minimise additional cartilage and bone injury, 2) reduce reliance on donors by ex vivo cell production, 3) could mimic natural biological processes of cartilage development, and 4) may provide tailored cell types to execute better repair. One technique using autologous chondrocytes is in the public domain and is commercially available having been used in several thousand US and Swedish patients www.genzyme.com). In this technique chondrocytes are isolated from a cartilage biopsy of a non-load bearing area, proliferated during several weeks, and re-introduced into the cartilage lesion by injection under a sutured and fibrin-sealed periosteal patch harvested from the patient's tibia. Knowledge of its efficacy has been questioned (Messner and Gillquist, 1996; Brittberg, 1997; Newman, 1998) and is unfortunately not known due to the lack of completion of an FDA requested controlled and randomised clinical trial. Recent animal studies indicate that the injected passaged autologous chondrocytes contribute very little to the observed healing and that the outcome is similar to that obtained using bone-marrow stimulation (Breinan et al., 1997 and Breinan et al., 2000). Thus the surgical preparation of the defect could be the main factor inducing repair, in this procedure as well. Nonetheless, due to the enormous potential benefit of cell transplantation, a large number of patents have been granted in the past two years to protect aspects of autologous chondrocyte processing (Tubo et al., U.S. Pat. No. 5,723,331, 1998; Villeneuve, U.S. Pat. No. 5,866,415, 1999), as well as the use and preparation of adipocytes (Mueller and Thaler, U.S. Pat. No. 5,837,235, 1998; Halvorsen et al., Patent EP 1 077 253, 2001), hematopoeitic precursors (Peterson and Nousek-Goebl, U.S. Pat. No. 6,200,606, 2001), amniotic membrane cells (Sackier, 1997), mesenchymal stem cells (Caplan and Hayneworth, U.S. Pat. No. 5,811,094, 1998; Naughton and Naughton, U.S. Pat. No. 5,785,964, 1998; Naughton and Willoughby, U.S. Pat. No. 5,842,477, 1998; Grande and Lucas, U.S. Pat. No. 5,906,934, 1999; Johnstone and Yoo, U.S. Pat. No. 5,908,784, 1999), and general techniques using chondrocytes/fibroblasts and their progenitors, epithelial cells, adipocytes, placental cells and umbilical cord blood cells (Purchio et al., U.S. Pat. No. 5,902,741, 1999), all for use in cartilage repair.

7) The Cell Delivery Problem

Cell transplantation for assisted cartilage repair necessarily involves a technique to deliver and retain viable and functional transplanted cells at the site of injury. When cells are grown ex vivo with or without a support matrix, press-fitting may be used by preparing an implant that is slightly larger than the defect and forcing it therein (Aston and Bentley 1986; Wakatini et al., 1989; Freed et al., 1994; Chu et al., 1997; Frankel et al., 1997; Kawamura et al., 1998). Press-fitting necessitates the use of a tissue that is formed ex vivo and thus not optimised for the geometric, physical, and biological factors of the site in which it is implanted. Suturing or tacking the implant can aid retention (Sams and Nixon, 1995) although sutures are known to be an additional injury to the articular surface inducing yet another limited repair process (Breinan et al., 1997). Biological glues have been attempted with limited success (Kandel et al., 1995; Jurgenson et al., 1997). When the implant is not amenable to press fitting, such as with contracting collagen gels or fibrin clots, or when cells alone without a support matrix are implanted, often a sutured patch of periosteum or another similar tissue is used to retain the implant material within the defect site (Grande et al., 1989; Brittberg et al., 1994; Grande et al., 1989; Brittberg et al., 1996; Breinan et al., 1997). Such a technique may benefit from an ability of the periosteum to stimulate cartilage formation (O'Driscoll et al., 1988 and 1994), but suffers again from the introduction of sutures and the complex nature of the operation involving periosteal harvesting and arthrotomy. Cells have also been delivered to deep full thickness defects using a viscous hyaluronic acid solution (Robinson et al., 1990; Butnariu-Ephrat, 1996). As with cell sources for cartilage repair, there are several recently published patents for delivery vehicles in cartilage repair ranging from gel matrices (Griffith et al., 1998; Caplan et al., 1999), to sutures and fibres (Vacanti et al., 1998; Vacanti and Langer, 1998a and 1998b), to screw type devices (Schwartz, 1998), and magnetic systems (Halpern, 1997). Taking together the above, current cell delivery techniques for cartilage repair are clearly not optimal. A desirable cell delivery vehicle would be a polymeric solution loaded with cells which solidifies when injected into the defect site, adheres and fills the defect, and provides a temporary biodegradable scaffold to permit proper cell differentiation and the synthesis and assembly of a dense, mechanically functional articular cartilage extracellular matrix.

8) Repair of Other Tissues Including Meniscus, Ligament, Tendon, Bone, Skin, Cornea, Periodontal Tissues, Abscesses, Resected Tumours, and Ulcers Natural and assisted repair of musculoskeletal and other tissues are very broad fields with numerous complex biological processes and a wide variety of approaches to accelerate the repair process (as in bone repair), aid it in tissues that have little intrinsic repair capacity (as in cartilage repair), and to reduce scarring (as in burn treatments) (Clark, 1996). Although differences certainly occur in the biological elements and processes involved, the global events in (non-fetal) wound repair are identical. These include the formation of a blood clot at the site of tissue disruption, release of chemotactic and mitogenic factors from platelets, influx of inflammatory cells and pluripotential repair cells, vascularisation, and finally the resolution of the repair process by differentiation of repair cells their synthesis of extracellular matrix components. In a successful repair outcome the specific local tissue environment and the specific local population of pluripotential repair cells will lead to the formation of the correct type of tissue, bone to replace bone, skin to replace skin etc. Given the similarity of the general elements in the tissue repair process, it is not surprising that approaches to aid repair in one tissue could also have some success in aiding repair in other tissues. This possibility becomes much more likely if the method and composition to aid repair is based upon augmenting some aspect of the natural wound healing cascade without significantly deviating from this more or less optimised sequence of events. In the present invention particular composition and methods are proposed to provide a more effective, adhesive, and non-contracting blood clot at the site of tissue repair. Examples and preferred embodiments are shown for cartilage repair, one of the most difficult tissues to repair. However application of the composition and method and modifications thereof, conserving the same basic principles, to aid repair of other tissues including meniscus, ligament, tendon, bone, skin, cornea, periodontal tissues, abscesses, resected tumours, and ulcers, are obvious to those who are skilled in the art.

9) Use of Chitosan in Pharmaceuticals, Wound Healing, Tissue Repair and as a Hemostatic Agent Chitosan, which primarily results from the alkaline deacetylation of chitin, a natural component of shrimp and crab shells, is a family of linear polysaccharides that contains 1–4 linked glucosamine (predominantly) and N-acetyl-glucosamine monomers (Austin et al., 1981). Chitosan and its amino-substituted derivatives are pH-dependent, bio-erodible and biocompatible cationic polymers that have been used in the biomedical industry for wound healing and bone induction (Denuziere et al., 1998; Muzzarelli et al., 1993 and 1994), drug and gene delivery (Carreno-Gomez and Duncan, 1997; Schipper et al., 1997; Lee et al., 1998; Bernkop-Schnurch and Pasta, 1998) and in scaffolds for cell growth and cell encapsulation (Yagi et al, 1997, Eser Elcin et al., 1998; Dillon et al., 1998; Koyano et al., 1998; Sechriest et al., 2000; Lahiji et al 2000; Suh et al., 2000). Chitosan is termed a mucoadhesive polymer (Bernkop-Schnurch and Krajicek, 1998) since it adheres to the mucus layer of the gastrointestinal epithelia via ionic and hydrophobic interactions, thereby facilitating peroral drug delivery. Biodegradability of chitosan occurs via its susceptibility to enzymatic cleavage by chitinases (Fukamizo and Brzezinski, 1997), lysozymes (Sashiwa et al., 1990), cellulases (Yalpani and Pantaleone, 1994), proteases (Terbojevich et al., 1996), and lipabes (Muzzarelli et al., 1995). Recently, chondrocytes have been shown to be capable of expressing chitotriosidase (vasios et al., 1999), the human analogue of chitosanase; its physiological role may be in the degradation of hyaluronan, a linear polysaccharide possessing some similarity with chitosan since it is composed of disaccharides of N-acetyl-glucosamine and glucuronic acid.

Chitosan has been proposed in various formulations, alone and with other components, to stimulate repair of dermal, corneal and hard tissues in a number of reports (Sall et al., 1987; Bartone and Adickes, 1988; Okamoto et al., 1995; Inui et al., 1995; Shigemasa and Minami, 1996; Ueno et al., 1999; Cho et al., 1999; Stone et al., 2000; Lee et al., 2000) and inventions (Sparkes and Murray, U.S. Pat. No. 4,572,906, 1986; Mosbey, U.S. Pat. No. 4,956,350, 1990; Hansson et al., U.S. Pat. No. 5,894,070, 1999; Gouda and Larm, U.S. Pat. No. 5,902,798, 1999; Drohan et al., U.S. Pat. No. 6,124,273, 2000; Jorgensen WO 98/22114, 1998). The properties of chitosan that are most commonly cited as beneficial for the wound repair process are its biodegradability, adhesiveness, prevention of dehydration and as a barrier to bacterial invasion. Other properties that have also been claimed are its cell activating and chemotractant nature (Peluso et al., 1994; Shigemasa and Minami, 1996; Inui et al., 1995) its hemostatic activity (Malette et al., 1983; Malette and Quigley, U.S. Pat. No. 4,532,134, 1985) and an apparent ability to limit fibroplasia and scarring by promoting a looser type of granulation tissue (Bartone and Adickes, 1988; Stone et al., 2000). Although a general consensus about the beneficial effects of chitosan in wound healing is apparent, its exact mechanism of action is not known, nor is the most effective means of its application, i.e. as a powder, suspension, sponge, membrane, solid gel etc. Part of the reason for the ambiguity in its mechanism of action could be that many previous studies used chitosan that was not chemically defined (acetyl content and distribution, molecular weight) and of unknown purity. The interesting hemostatic potential of chitosan has also led to its direct application to reduce bleeding at grafts and wound sites (Malette et al., 1983; Malette and Quigley, U.S. Pat. No. 4,532,134, 1985). Some studies claim that the hemostatic activity of chitosan derives solely from it's ability to agglutinate red blood cells (Rao and Sharma, 1997) while others believe its polycationic amine character can activate platelets to release thrombin and initiate the classical coagulation cascade thus leading to its use as a hemostatic in combination with fibrinogen and purified autologous platelets (Cochrum et al. U.S. Pat. No. 5,773,033, 1998). In the context of the present invention, it is important to note in these reports and inventions a complete lack of any example where blood was mixed with chitosan in solution and applied therapeutically to aid tissue repair through the formation of a chitosan containing blot clot at the repair site.

One technical difficulty that chitosan often presents is a low solubility at physiological pH and ionic strength, thereby limiting its use in a solution state. Thus typically, dissolution of chitosan is achieved via the protonation of amine groups in acidic aqueous solutions having a pH ranging from 3.0 to 5.6. Such chitosan solutions remain soluble up to a pH near 6.2 where neutralisation of the amine groups reduces interchain electrostatic repulsion and allows attractive forces of hydrogen bonding, hydrophobic and van der Waals interactions to cause polymer precipitation at a pH near 6.3 to 6.4. A prior invention (Chenite Patent WO 99/07416; Chenite et al., 2000) has taught that admixing a polyol-phosphate dibasic salt (i.e. glycerol-phosphate) to an aqueous solution of chitosan can increase the pH of the solution while avoiding precipitation. In the presence of these particular salts, chitosan solutions of substantial concentration (0.5–3%) and high molecular weight (>several hundred kDa) remain liquid, at low or room temperature, for a long period of time with a pH in a physiologically acceptable neutral region between 6.8 and 7.2. This aspect facilitates the mixing of chitosan with cells in a manner that maintains their viability. An additional important property is that such chitosan/polyol-phosphate (C/PP) aqueous solutions solidify or gel when heated to an appropriate temperature that allows the mixed chitosan/cell solutions to be injected into body sites where, for example cartilage nodules can be formed in subcutaneous spaces in nude mice (Chenite et al., 2000). It is important to note that some other studies have retained chitosan in a soluble state at physiological pH but these studies necessitated the reduction of either chitosan concentration (to 0.1% in Lu et al Biomaterials 1999) or of chitosan, molecular weight and degree of deacetylation (to ~350 kD and 50% in respectively in Cho et al Biomaterials, 1999) Other studies have also shown that chitosan presents a microenvironment that supports the chondrocyte and osteoblast phenotype (Suh et al., 2000; Lahiji et al., 2000; Seichrist et al., 2000) however these studies were not based on liquid chitosan in a form that could be mixed with cells and injected. Finally NN-dicarboxylmethyl chitosan sponges have been soaked with BMP7 and placed into osteochondral defects of rabbits (Mattioli-Belmonte, 1999). Here again some improved histochemical and immunohistochemical outcome was observed, however, incomplete filling of the defect with repair tissue and a significant difficulty in retaining the construct within the defect appeared to be insurmountable problems. The present invention overcomes these issues and presents several novel solutions for the delivery of compositions for the repair of cartilage and other tissues.

10) Summary of Prior Art

In summary of prior art for assisted cartilage repair, it may be said that many techniques to improve the very limited natural repair response of articular cartilage have been proposed and experimentally tested. Some of these techniques have achieved a certain level of acceptance in clinical practice but this has mainly been so due to the absence of any practical and clearly effective method of improving the repair response compared to that found when the family of bone marrow stimulation techniques is applied. This invention addresses and solves several of the main problematic issues in the use of cells and blood components to repair articular cartilage. One main obstacle towards the development of an effective cartilage repair procedure is the absence of a composition and method to provide an appropriate macromolecular environment within the space requiring cartilage growth (cartilage defect or other site requiring tissue bulking or reconstruction) This macromolecular environment or matrix should 1) be amenable to loading with active biological elements (cells, proteins, genes, blood, blood components) in a liquid state 2) then be injectable into the defect site to fill the entire defect or region requiring cartilage growth 3) present a primarily nonproteinaceous environment to limit cell adhesion and cell-mediated contraction of the matrix, both of which induce a fibrocytic cellular phenotype (fibrous tissue producing) rather than chondrocytic cellular phenotype (cartilaginous tissue producing) and which can also disengage the matrix from the walls of the defect 4) be cytocompatible, possessing physiological levels of pH and osmotic pressure and an absence of any cytotoxic elements 5) be degradable but present for a sufficiently long time to allow included biologically active elements to fully reconstitute a cartilaginous tissue capable of supporting mechanical load without degradation. In addition it is obvious to those skilled in the art that such a combination of characteristics could be applied with minimal modifications towards the repair of other tissues such as meniscus, ligament, tendon, bone, skin, cornea, periodontal tissues, abscesses, resected tumors, and ulcers.

It would be highly desirable to be provided with a new composition for use in repair and regeneration of cartilaginous tissues.

SUMMARY OF THE INVENTION

One aim of the present invention is to provide a new composition for use in repair and regeneration of cartilaginous tissues.

In accordance with the present invention, there is thus provided a composition for use in repair, regeneration, reconstruction or bulking of tissues of cartilaginous tissues or other tissues such as meniscus, ligament, tendon, bone, skin, cornea, periodontal tissues, abscesses, resected tumors, and ulcers.

In accordance with the present invention, there is also provided the use of a polymer solution that can be mixed with biological elements and placed or injected into a body site where the mixture aids the repair, regeneration, reconstruction or bulking of tissues. Repaired tissues include for example without limitation cartilage, meniscus, ligament, tendon, bone, skin, cornea, periodontal tissues, abscesses, resected tumors, and ulcers.

The biological elements are preferably based on blood, blood components or isolated cells, both of autologous or non-autologous origin.

Also in accordance with the present invention, there is provided a method for repairing a tissue of a patient, said method comprising the step of introducing into said tissue a temperature-dependent polymer gel composition such that said composition adhere to the tissue and promote support for cell proliferation for repairing the tissue.

The composition preferably comprises at least one blood component.

Still in accordance with the present invention, there is provided a method for repairing a tissue of a patient, said method comprising the step of introducing a polymer composition in said tissue, said polymer composition being mixable with at least one blood component, said polymer composition when mixed with said blood component results in a mixture, said mixture turning into a non-liquid state in time or upon heating, said mixture being retained at the site of introduction and adhering thereto for repairing the tissue.

The polymer can be a modified or natural polysaccharide, such as chitosan, chitin, hyaluronan, glycosaminoglycan, chondroitin sulfate, keratan sulfate, dermatan sulfate, heparin, or heparin sulfate.

The polymer composition may comprise a natural, recombinant or synthetic protein such as soluble collagen or soluble gelatin or a polyamino acids, such as for example a polylysine.

The polymer composition may comprise polylactic acid, polyglycolic acid, a synthetic homo and block copolymers containing carboxylic, amino, sulfonic, phosphonic, phosphenic functionalities with or without additional functionalities such as for example without limitation hydroxyl, thiol, alkoxy, aryloxy, acyloxy, and aroyloxy.

The polymer composition is preferably initially dissolved or suspended in a buffer containing inorganic salts such as sodium chloride, potassium calcium, magnesium phosphate, sulfate, and carboxylate.

The polymer composition may be dissolved or suspended in a buffer containing an organic salt such as glycerolphosphate, fructose phosphate, glucose phosphate, L-Serine phosphate, adenosine phosphate, glucosamine, galactosamine, HEPES, PIPES, and MES.

The polymer composition has preferably a pH between 6.5 and 7.8 and an osmolarity adjusted to a physiological value between 250 mOsm/L and 600 mOsm/L.

The blood component may be for example without limitation whole blood, processed blood, venous blood, arterial blood, blood from bone, blood from bone-marrow, bone marrow, umbilical cord blood, or placenta blood. It may also comprise erythrocytes, leukocytes, monocytes, platelets, fibrinogen, thrombin or platelet rich plasma free of erythrocytes.

The blood component can also comprise an anticoagulant such as citrate, heparin or EDTA. To the opposite the blood component can comprise a pro-coagulant such as thrombin, calcium, collagen, ellagic acid, epinephrine, adenosine diphosphate, tissue factor, a phospholipid, and a coagulation factor like factor VII to improve coagulation/solidification at the site of introduction.

The blood component may be autologous or non-autologous.

The polymer composition is preferably used in a ratio varying from 1:100 to 100:1 with respect to the blood component.

The polymer composition and the blood component are preferably mechanically mixed using sound waves, stirring, vortexing, or multiple passes in syringes.

The tissue that can be repaired or regenerated is for example without limitation cartilage, meniscus, ligament, tendon, bone, skin, cornea, periodontal tissue, abscesses, resected tumors, or ulcers. In some cases, the site of introduction in the body may be surgically prepared to remove abnormal tissues. Such procedure can be done by piercing, abrading or drilling into adjacent tissue regions or vascularized regions to create channels for the polymer composition to migrate into the site requiring repair.

Further in accordance with the present invention, there is provided a chitosan solution for use in cell delivery to repair or regenerate a tissue in vivo, said chitosan solution comprising 0.5–3% w/v of chitosan and being formulated to be thermogelling, said solution being mixed with cells prior to being injected into a tissue to be repaired or regenerated. The solution may be induced to thermogel by addition of phosphate, glycerol phosphate or glucosamine, just to name a few for example. Preferable, the chitosan solution has a pH between 6.5 to 7.8.

The cells may be selected for example from the group consisting of primary cells, passaged cells, selected cells, platelets, stromal cells, stem cells, and genetically modified cells. Preferably the cells are suspended in a carrier solution, such as a solution containing hyaluronic acid, hydroxyethylcellulose, collagen, alginate, or a water-soluble polymer.

In accordance with the present invention, there is also provided a gelling chitosan solution for use in culturing cells in vitro, said chitosan solution comprising 0.5–3% w/v of chitosan and being formulated to be thermogelling, said solution being is mixed with cells prior to being cultured in vitro.

Preferably, the polymer composition contains between 0.01 and 10% w/v of 20% to 100% deacetylated chitosan with average molecular weight ranging from 1 kDa to 10 Mda and a blood component.

In accordance with the present invention, there is further provided a polymer composition for use in repairing a tissue, and the use thereof. The composition may also be used for the manufacture of a remedy for tissue repair.

For the purpose of the present invention the following terms are defined below.

The terms "polymer" or "polymer solution", both interchangeable in the present application are intended to mean without limitation a polymer solution, a polymer suspension, a polymer particulate or powder, and a polymer micellar suspension.

The term "repair" when applied to cartilage and other tissues is intended to mean without limitation repair, regeneration, reconstruction, reconstitution or bulking of tissues.

BRIEF DESCRIPTION OF THE DRAWINGS

FIGS. 2A to 2C illustrate the viability of chondrocytes after encapsulation and culture in a chitosan/glycerol-phosphate gel;

FIGS. 3A to 3E illustrates cartilage formation within chitosan gel in vitro, as measured by glycosaminoglycan (GAG) accumulation;

FIG. 4 illustrates a RNase protection analysis of cartilage-specific mRNAs expressed by primary chondrocytes cultured in chitosan gel for 0, 14 and 20 days;

FIG. 5 illustrates a western blot analysis of cartilage-specific proteins expressed by primary chondrocytes cultured in chitosan gel for 0, 14 and 20 days;

FIG. 7 is a schematic representation of polymer mixing with cells and subcutaneous injection into mice;

FIG. 9 illustrates a RNase protection analysis of cartilage-specific mRNAs expressed in in vivo implants of chitosan gel with or without primary chondrocytes;

FIG. 10 illustrates a western blot analysis of cartilage-specific proteins expressed in vivo in mouse implants of chitosan gel harboring primary chondrocytes;

FIG. 15A is a schematic representation showing the preparation, mixing and in vitro solidification of a blood/polymer mixture;

FIGS. 15B and 15C illustrate the liquid blood/polymer solidification in vitro, in an agarose well (FIG. 15B) or tube (FIG. 15C) composed of glass or plastic;

FIG. 21 illustrates a prolonged release of blood proteins from an in vitro-formed blood/polymer mixture versus blood alone;

FIGS. 22A to 22C illustrate the preparation, mixing and injection of polymer/blood mixture to improve healing of articular cartilage defects;

FIGS. 22D and 22E are a schematic representation of therapy to heal human articular cartilage;

FIGS. 23A and 23B illustrate enhanced chemotaxis of repair cells originating from bone marrow and migrating towards the cartilage defect, 1 week after delivery of the blood/polymer mixture to a chondral defect with bone-penetrating holes.

DETAILED DESCRIPTION OF THE INVENTION

Figure 1C:
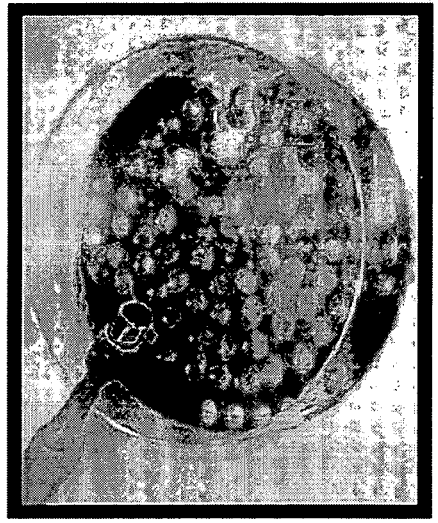
FIGS. 1A to 1F are schematic representation of the mixing of polymer solution with cells and in vitro solidification and culture for cartilage growth.

When combined with blood or blood components the polymer could be in an aqueous solution or in an aqueous suspension, or in a particulate state, the essential characteristics of the polymer preparation being that 1) it is mixable with blood or selected components of blood, 2) that the resulting mixture is injectable or can be placed at or in a body site that requires tissue repair, regeneration, reconstruction or bulking and 3) that the mixture has a beneficial effect on the repair, regeneration, reconstruction or bulking of tissue at the site of placement.

A preferred embodiment is shown in Example 5 where a solution of the natural polysaccharide, chitosan, was used at a concentration 1.5% w/v and in 0.135 moles/L disodium glycerol phosphate buffer at pH=6.8. This solution was mixed with peripheral rabbit blood at a ratio of 1 part polymer solution to 3 parts blood. The polymer/blood mixture was then injected into a surgically prepared articular cartilage defect in the rabbit where it solidified within 5 minutes (FIG. 22). Histological observations of the healing process revealed a stimulated repair that resulted in hyaline cartilage after 6–8 weeks (FIG. 24). Control defects that did not receive the polymer/blood mixture were incompletely healed or healed with non-functional fibrous or fibrocartilagenous tissue (FIG. 24). This example demonstrates that the use of a polymer/blood mixture can result in more effective healing and greater functionality of repaired tissue than simply inducing bleeding at the wound site. Trivial modifications of this invention are evident to those skilled in the art. Other polymers and other formulations of polymers or polymer blends may be substituted for the chitosan solution providing they retain the three characteristics cited in the previous paragraph. And clearly, this approach may be trivially applied to the repair of tissues other than cartilage such as meniscus, ligament, tendon, bone, skin, cornea, periodontal tissues, abscesses, resected tumors, and ulcers. Applications in tissue bulking and reconstruction are also evident.

We present examples and evidence to teach possible mechanisms of action of this invention including 1) inhibition of the typical platelet-mediated contraction of a blood clot by mixing blood with the polymer prior to solidification (FIG. 17) 2) the resulting maintained full-volume scaffold and therefore better defect filling for tissue repair (FIG. 18) 3) adherence of the solidified polymer/blood mixture to the surrounding tissues (FIG. 22A) 4) a slower release of chemotactic and mitogenic protein factors from the polymer/blood mixture than from a simple blood clot (FIG. 21) 5) maintenance of leukocyte and platelet viability in the polymer blood/mixture (FIG. 20) and 6) provision of a polysaccharide environment in the repair site that is more conducive to cartilage formation than is a purely proteinaceous matrix (FIGS. 2–6, 8–10, 24). These phenomena are demonstrated to occur in our examples. Their demonstration does not, however, reject the possibility that other important events occur such as those involving the kinetics of cellular degradation of the polymer, and binding/concentration of endogenous factors by the chitosan.

A second preferred embodiment of this invention is shown in Examples 1 and 2 where a thermogelling chitosan solution was used to deliver primary chondrocytes to subcutaneous regions in mice or to culture chambers in vitro. In this case the absence of blood components necessitates a gelling capability on the part of the chitosan solution alone, and this property is endowed via a particular preparation of the chitosan solution using glycerol phosphate and other similar buffers. In our examples we demonstrate that the polymer solution may be mixed with cells and the polymer/cell solution injected in vivo or in vitro whereupon it gels, maintaining functionality and viability of the cells (FIGS. 1-11). The cells may be resuspended in a physiological buffer, or other cell carrier suspension such as cellulose in an isotonic buffer, prior to mixing with the chitosan solution. We show data demonstrating the formation of cartilage tissue in vitro (FIGS. 2–6) and in vivo (FIGS. 8–11) when primary chondrocytes are injected with this polymer solution. Trivial modifications and extensions of this embodiment of the invention are also evident to those skilled in the art where, for example, other cell types may be used and concentrations of the chitosan and the buffer may be changed to achieve the same result.

The present invention will be more readily understood by referring to the following examples, which are given to illustrate the invention rather than to limit its scope.

EXAMPLE 1

Mixing of Thermogelling Chitosan Solution with Primary Chondrocytes for In Vitro Growth of Cartilage Chitosan (0.22 g, 85% deacetylated) as an HCl salt powder was sterilized by exposure to ultraviolet radiation in a biological laminar flow hood and then dissolved in 7.5 ml $H_2O$ resulting in a pH near 5.0. D(+)-glucosamine (0.215 g, MW 215.6) was dissolved in 10 ml of 0.1M NaOH and filter sterilized using a 22 µm pore size disk filter. Glycerol phosphate (0.8 g, MW 297 including 4.5 mole water per mole glycerol phosphate) was dissolved in 2.0 ml of $H_2O$ and filter sterilized using a 22 µm pore size disk filter. 2.25 ml of the glucosamine solution was added drop-by-drop under sterile conditions to the chitosan solution with agitation at a temperature of 4° C. Then 1 ml of the glycerol phosphate solution was added under the same conditions. This final solution is still a liquid and remains so for an extended period (i.e. days) if the temperature is kept low, i.e. near 4° C. The pH of this solution is physiological at 6.8 and the osmolarity is also physiological, around 376 mOsm/kg-$H_2O$. It is of critical importance to retain these two parameters within the limits required to maintain cell viability. These limits vary with cell type but are generally $6.6 < pH < 7.8$ and $250$ mOsm/kg-$H_2O$<osmolarity<450 mOsm/kg-$H_2O$. A solution is prepared by dissolving 150 mg hydroxyethyl cellulose (Fluka) and 6 ml DMEM (Dulbecco's modified Eagles Medium), and filter sterilized using a 22 µm pore size disk filter. A cell pellet is resuspended with 2 ml of hydroxyethyl cellulose-DMEM solution, and admixed into the chitosan-glycerol phosphate solution. As a negative control, the chitosan solution mixed with 2 ml of hydroxyethyl cellulose-DMEM solution with no cells was generated. When this solution is heated to 37° C. it transforms into a solid hydrogel similarly to the thermogelling solution disclosed in a previous invention (Chenite et al. Patent WO 99/07416). Most importantly, this previous invention did not demonstrate that cell viability was maintained throughout the thermogelling process in this chitosan solution, and thus did not enable the use of this chitosan solution for cell delivery, tissue repair and tissue regeneration.

Figure 1F:
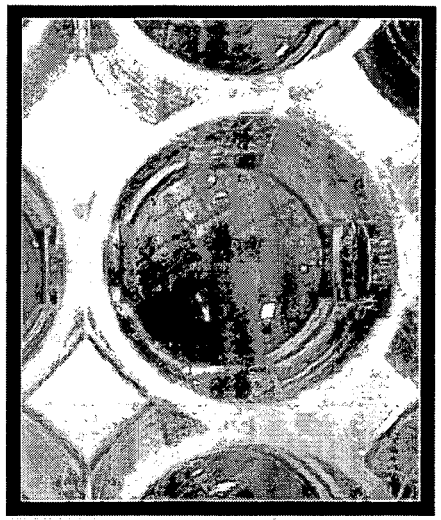
Figure 1B:
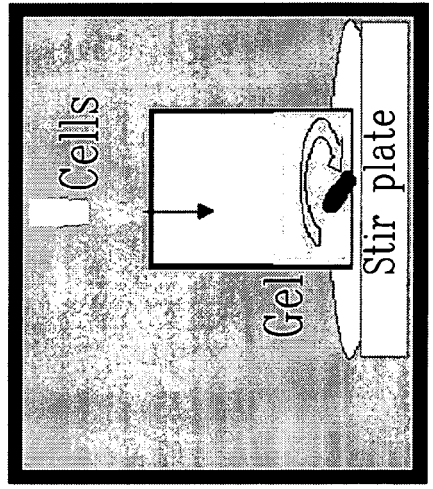
Figure 1E:
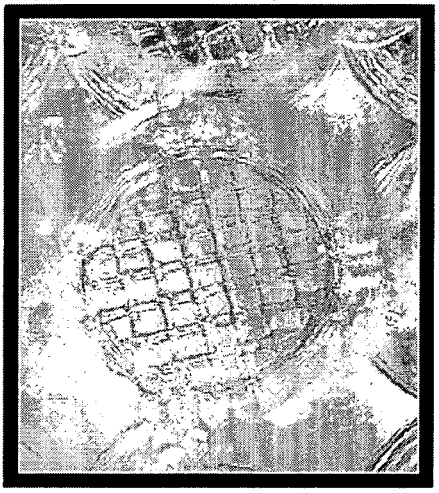
Figure 1A:
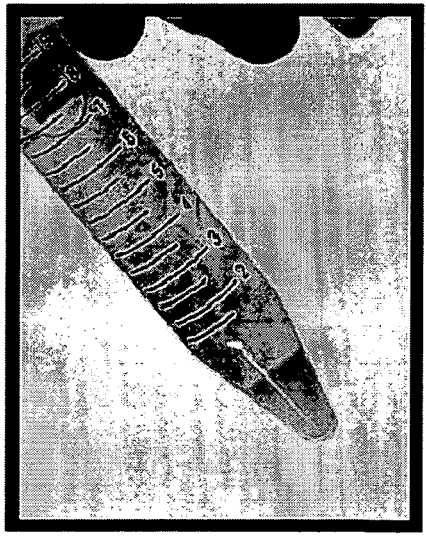
Figure 1D:
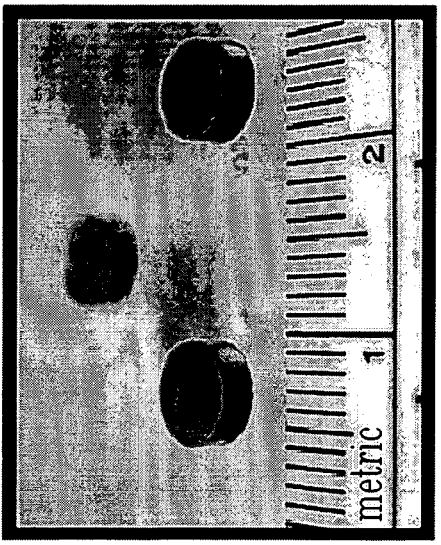

The above solution in the liquid state at 4° C. was mixed with enzymatically isolated primary chondrocytes (Buschmann et al., 1992) and then poured into a plastic culture dish (FIGS. 1A to 1F). In FIG. 1A, a cell pellet is resuspended and admixed (FIG. 1B) into the liquid chitosan gel solution at 4° C. In FIGS. 1C and 1D, the liquid solution is poured into a tissue culture petri and allowed to solidify at 37° C. for 30 minutes, after which the solid gel with cells is washed with DMEM, and discs cored using a biopsy punch. In FIG. 1E, 1000 µm pore mesh grids are placed in 48-well plates. In FIG. 1F, the chitosan gel discs with cells are placed in culture in individual wells.

A gel harboring cells formed after a 20 minute incubation at 37° C. Using a biopsy punch, 6 mm diameter 1 mm thick discs were cored from the gel and placed in culture for up to 3 weeks. Discs were cultured individually in 48-well tissue culture plates with sterile nylon 1000 µM meshes beneath to allow media access to all surfaces. Over 90% of the encapsulated cells were viable immediately after encapsulation, and throughout the culture period (FIGS. 2A to 2C). Samples were incubated in calcein AM and ethidium homodimer-1 to reveal live (green) and dead (red) cells. Freshly isolated chondrocytes (FIG. 2A) were encapsulated in the gel, solidified and tested immediately for viability (FIG. 2B), or after 20 days of culture in the gel (FIG. 2C). FIG. 2C shows cells with typical chondrocyte morphology from the middle of the gel.

Several distinct cell types exhibited the same high degree of viability after encapsulation and cell culture, including Rat-1, COS, 293T, and de-differentiated bovine articular chondrocytes, confirming that the gelation process maintained cell viability, and could thus be used to deliver cells in vivo by injection. Toluidine blue staining of the gel with cells after 22 days of culture revealed a metachromatic ring of staining surrounding encapsulated primary chondrocytes, indicating the build-up of proteoglycan, or GAG, which was beginning to fuse between closely adjacent cells (FIG. 3D). These regions also stained with antibodies raised against aggrecan, type II collagen and link protein. The chitosan gel matrix was also found to bind Toluidine blue (FIG. 3C). This property enabled to observe the lattice structure of the gel, after employing an aldehyde fixation. Interestingly, the pericellular ring of GAG observed around the chondrocytes contained little chitosan matrix, the latter appearing to have been degraded by chondrocyte-produced factors (FIG. 3D). Primary calf chondrocytes were encapsulated in chitosan gel at $2 \times 10^7$ primary chondrocytes per ml and cultured as 6 mm discs for up to 20 days. Primary calf chondrocytes were encapsulated and cultured in 2% agarose and analyzed in parallel. Day 0 and day 20 cultures were processed by paraffin sectioning and toluidine blue staining for agarose gel cultures (FIGS. 3A and 3B) and chitosan gel cultures (FIGS. 3C and 3D). At day=0, nuclei stain dark blue (FIGS. 3A and 3C) whereas accumulated pericellular GAG stains metachromatic blue-violet (FIGS. 3B and 3D, large arrows). These pericellular regions were immunopositive for aggrecan, collagen (II) and cartilage link protein. At a magnification of 40× in FIG. 3E, quantitative biochemical analysis of GAG present at days 0, 14, and 20 of culture using the DMMB assay revealed a similar accumulation of GAG in chitosan gel compared with agarose gel.

RNA analysis of type II collagen and aggrecan mRNA expressed by the encapsulated chondrocytes revealed high levels at 14 and 22 days of culture (FIG. 4, lanes 4 and 5) that were comparable to those levels observed in articular chondrocytes in cartilage (FIG. 4, lane 6). A mixture of antisense $^{32}$P-labeled RNA probes complementary to bovine type II collagen, aggrecan, and GAPDH was hybridized with tRNA (lane 1), or total RNA, from bovine kidney (lane 2), from primary chondrocytes ($10^7$/ml) cultured in chitosan gel for 0 days (lane 3) 14 days (lane 4) or 20 days (lane 5), or adult bovine articular cartilage (lane 6). Samples were treated with RNase A and T1, then submitted to electrophoresis and autoradiography. Protected bands showing the presence of individual transcripts are as indicated. The maintenance of the chondrocyte phenotype in the chitosan/glycerol-phosphate gel is shown by the continued expression of aggrecan and type II collagen.

Western analysis of proteins produced by encapsulated cells showed an accumulation of cartilage matrix link protein between 2 and 3 weeks in culture (FIG. 5). Total proteins were extracted, separated by SDS-PAGE, and immunoblotted with antisera recognizing vimentin, PCNA, the C-propeptide of type II collagen, or cartilage link protein. Samples analyzed include chitosan gel with no cells (lane 1), bovine kidney (lane 2), duplicate samples of primary chondrocytes ($10^7$/ml) cultured in chitosan gel at day=0 (lanes 3 and 4), day=14 (lanes 5 and 6), or day=20 (lanes 7 and 8), 2-week calf articular cartilage (lane 9), or adult bovine cartilage (lane 10). Results show the accumulation of cartilage-specific proteins CP2 and link at 14 and 20 days, as well as the persistence of PCNA expression through culture day 20, as a marker for cell proliferation.

Figure 6:
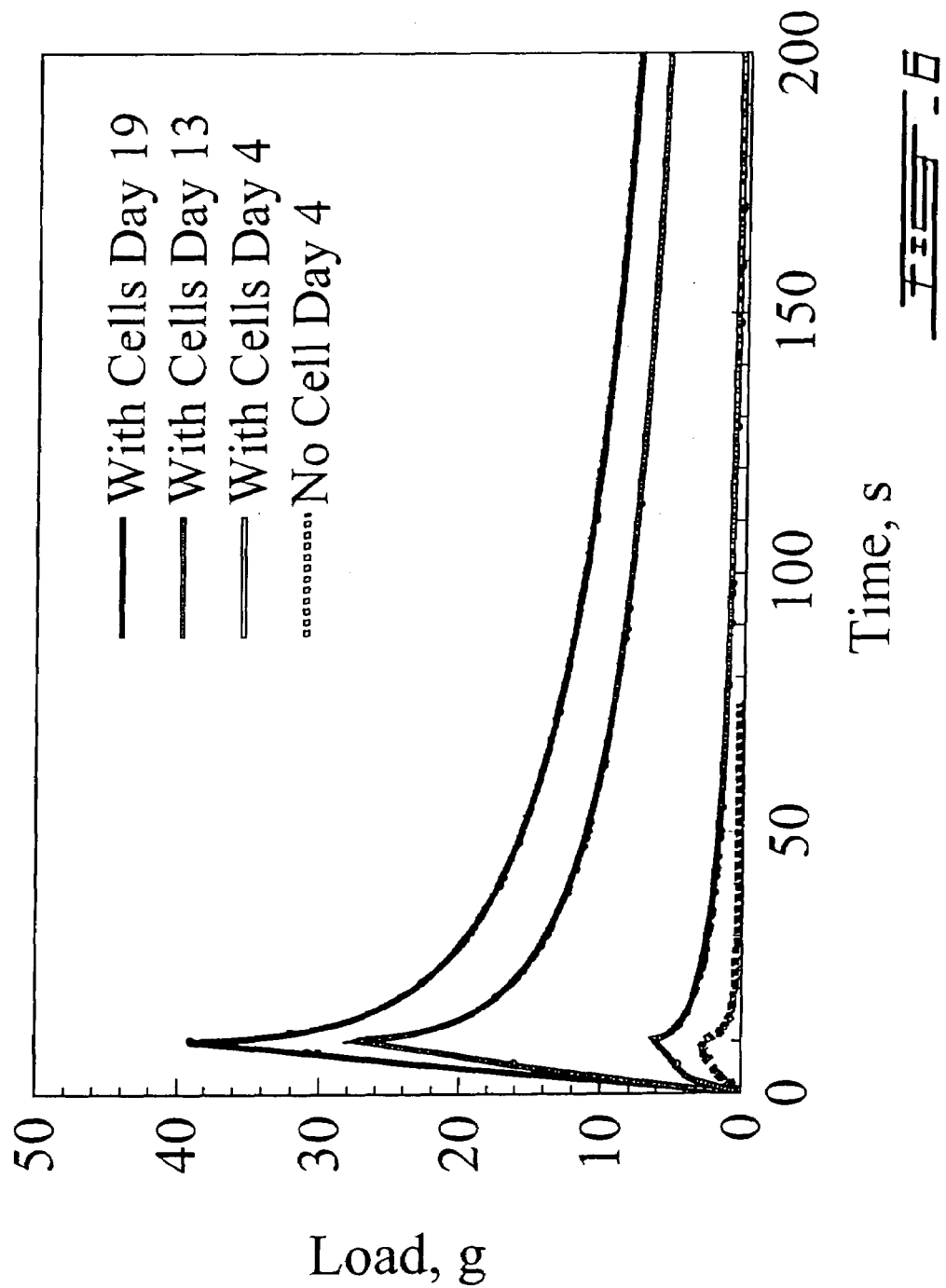
FIG. 6 illustrates a mechanical behavior of gel discs cultured with and without chondrocytes.

Discs containing primary bovine articular chondrocytes were mechanically evaluated at days 4 and 13 of culture using uniaxial unconfined compression stress relaxation tests. By comparing to control gels with no cells, a significant, cell-dependent degree of stiffening was observed even at day 4 and became much more dramatic at day 13 (FIG. 6). Discs (~5 mm diameter) from days 4, 13 and 19 of culture were mechanically tested in unconfined compression by applying 5 ramps of 10% the disk thickness (~1.5 mm) during 10 seconds and holding that displacement during subsequent stress relaxation (the 2nd ramp from 10–20% is shown in the graph). The gel discs without cells displayed a weak behavior while cell-laden gels became evidently stiffer with time in culture and more characteristically viscoelastic, like articular cartilage.

By analyzing these data with a composite poroelastic model (Soulhat et al., 1999) a doubling of the non-fibrillar matrix modulus (2.5→5 kPa) was found, a 5× increase in the fibrillar matrix modulus (100→500 kPa) was also found together with a near 100× reduction in hydraulic permeability (5→0.08×10–12 N-s/m4) due to the presence of primary chondrocytes in these gels during only 13 days of culture in vitro. Taken together, these results demonstrate that the chitosan gel is cytocompatible and cytodegradable, conducive to maintenance of the chondrocyte phenotype, and permits the elaboration of a neo-cartilage matrix with a significant increase in mechanical stiffness in vitro.

EXAMPLE 2

Mixing of Thermogelling Chitosan Solution with Primary Chondrocytes and Subcutaneous Injection for In Vivo Growth of Cartilage To demonstrate that this in situ gelling system can be employed in animals, athymic mice (CD1 nu/nu) were subjected to dorsal, subcutaneous injections of 100 to 300 µl of chitosan gel described in Example 1, containing 10 million calf articular chondrocytes per ml (FIG. 7). A cell pellet of primary calf chondrocytes was admixed with liquid chitosan gel at 4° C. to achieve a concentration of 1 to $2 \times 10^7$ cells/ml, and injected in liquid form as 100 µl subcutaneous dorsal implants in anesthetized nude mice. In situ gelling was apparent by palpation 5 to 10 minutes post-injection.

Figure 8A:
FIGS. 8A and 8B illustrate a toluidine blue histology of cartilage grown subcutaneously in nude mice.
Figure 8B:
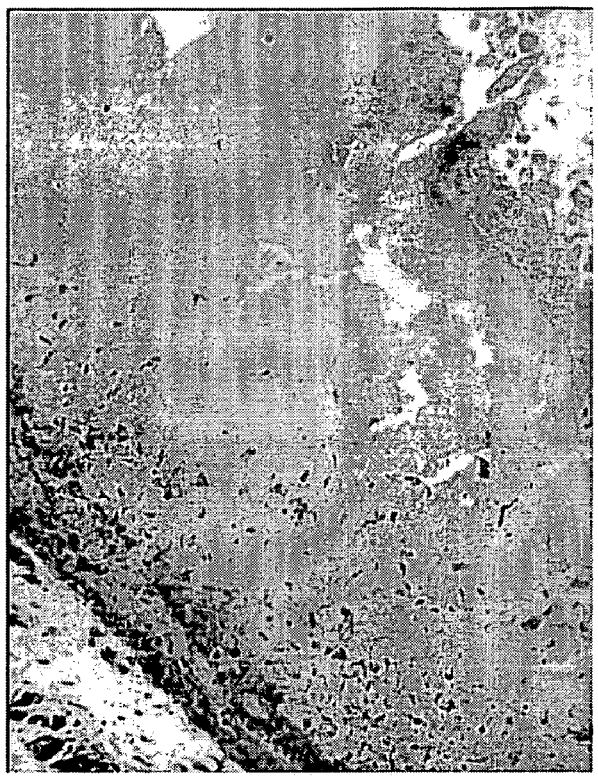

Control mice were similarly injected with chitosan gel alone. A palpable gel was formed within 10 minutes of injection. Implants were recovered at 21, 48, and 63 days post-injection. Toluidine blue staining revealed the gross production of GAG-rich extracellular matrix by the implants containing cells (FIG. 8A). No GAG accumulation was seen in implants of chitosan gel alone (FIG. 1B). Primary calf chondrocytes at $2\times10^7$ cells/ml liquid chitosan gel were injected in liquid form as 100 µl subcutaneous dorsal implants in anesthetized nude mice. Control mice received 100 µl subcutaneous dorsal implants of liquid chitosan gel alone. 48 days after injection, implants were harvested and processed for paraffin histology and toluidine blue staining. Metachromatic violet staining reveals the accumulation of GAG in the implant with chondrocytes (FIG. 8A). No GAG accumulation is detected in the implant with chitosan gel only (FIG. 8B).

Cartilage-specific mRNA expression, collagen type II and aggrecan, was detected in the in vivo implants with primary chondrocytes at day 48 post-injection (FIG. 9).

No type II collagen or aggrecan expression was detected in implants of chitosan gel alone (FIG. 9). A mixture of antisense $^{32}$P-labelled RNA probes complementary to bovine type II collagen, aggrecan, and GAPDH were hybridized with tRNA (lane 1), or total RNA, from bovine kidney (lane 2), from day=48 in vivo nude mouse implants with chitosan gel only (lane 3) or day=48 in vivo implants of chitosan gel with primary chondrocytes at $2\times10^7$ cells/ml (lane 4), or adult bovine articular cartilage (lane 5). Samples were treated with RNase A and T1, then submitted to electrophoresis and autoradiography. Protected bands showing the presence of individual transcripts are as indicated. The maintenance in vivo of the chondrocyte phenotype in the chitosan/glycerol-phosphate gel is shown by the expression of aggrecan and type II collagen.

Cartilage-specific proteins were detected in in vivo implants with primary chondrocytes from days 48 and 63 post-injection (FIG. 10). No cartilage-specific proteins were detected in implants with chitosan gel only (FIG. 10). Total proteins were extracted, separated by SDS-PAGE, and immunoblotted with antisera recognizing vimentin, PCNA, the C-propeptide of type II collagen, or cartilage link protein. Samples analysed include chitosan gel with no cells (lane 1), bovine kidney (lane 2), two distinct in vivo nude mouse implants of chitosan gel only at day 63 (lanes 3 and 4), of in vivo implants of chitosan gel with $2\times10^7$ calf chondrocytes per ml gel at days 48 (lane 5) or day 63 (lane 6), 2-week calf cartilage (lane 7), or adult bovine cartilage (lane 8). Results show the accumulation of cartilage-specific extracellular matrix proteins CP2 and link, in only those chitosan gel implants carrying chondrocytes. The acronym PCNA means "proliferating cell nuclear antigen". CP refers to type 2 collagen C pro-peptide and link refers to cartilage link protein.

Figure 11:
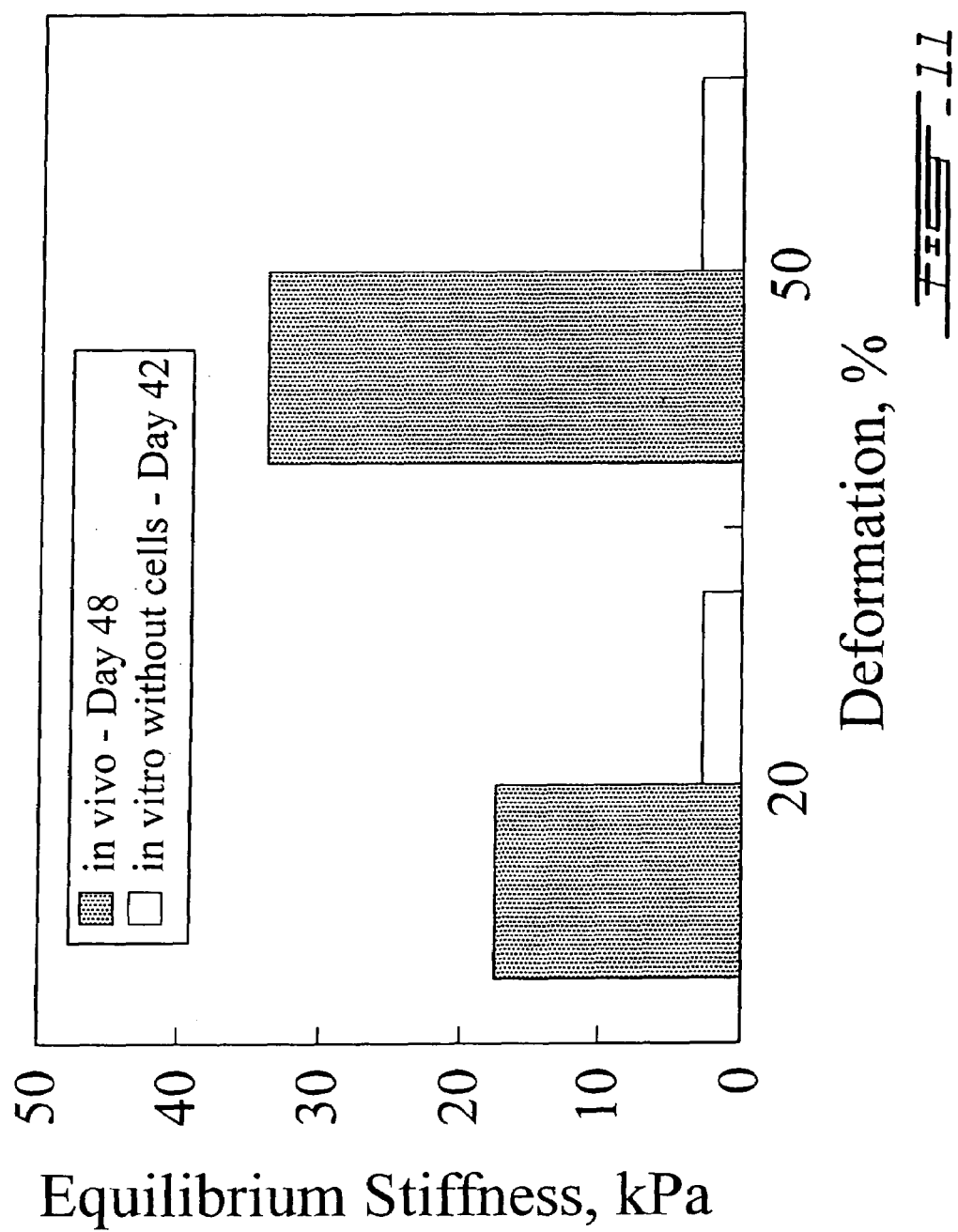
FIG. 11 illustrates the mechanical properties of cartilage implants grown subcutaneously in nude mice.

The in vivo implants with no cells had a pasty consistency, whereas the implants with cells could be cored into 3 to 5 mm discs and subjected to mechanical testing to reveal a high mechanical stiffness not found in an in vitro disc without cells (FIG. 11). These data indicate that chondrocytes can be delivered in situ, via injection, with the chitosan thermogelling solution as a carrier. The injected chondrocytes remain viable, and synthesize and assemble significant levels of a proteoglycan-rich extracellular matrix that stiffens over time to form a functional cartilaginous tissue. In FIG. 11, primary calf chondrocytes at $2\times10^7$ cells/ml liquid chitosan gel were injected in liquid form as 100 µl subcutaneous dorsal implants in anesthetized nude mice. Control mice received 100 µl subcutaneous dorsal implants of liquid chitosan gel alone. 48 days after injection, implants were harvested. Implants of chitosan gel only had a paste-like consistency, and could not be mechanically tested. Implants with primary chondrocytes had the appearance of cartilage, and a 3 mm biopsy was cored from the center of the implant, and tested in unconfined compression using 2.5% thickness compression with a relaxation criteria of 0.05 g/min. The equilibrium modulus at 20% and 50% compression offset is shown for the 48 day implant containing cells compared to a control disk left in vitro during a 42 day period. The in vivo grown chondrocyte laden gel has developed substantial mechanical stiffness during 48 days due to the synthesis and assembly of a functional cartilage matrix (FIG. 8A).

EXAMPLE 3

Adhesion of Thermogelling Chitosan Solution to Cartilage and Bone Surfaces

Figure 12B:
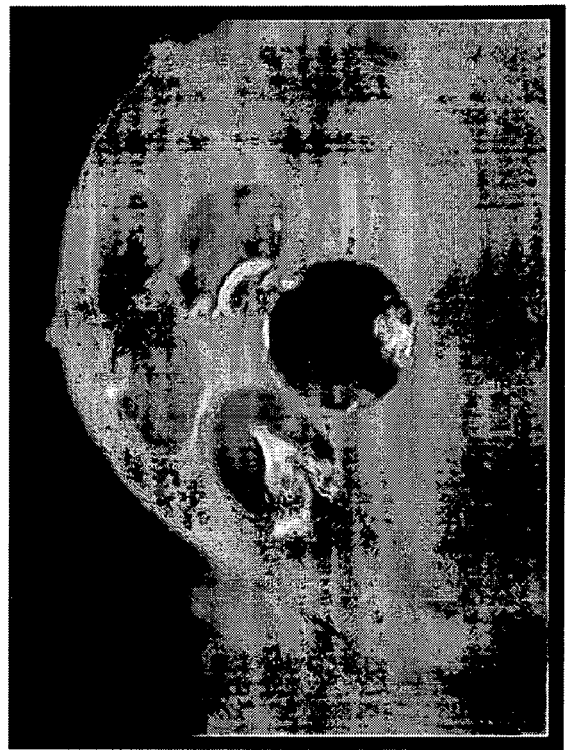
FIGS. 12A and 12B illustrate adhesion of thermogelling chitosan solution to chondral only defects in ex vivo porcine femoral condyles of intact joints.
Figure 12A:
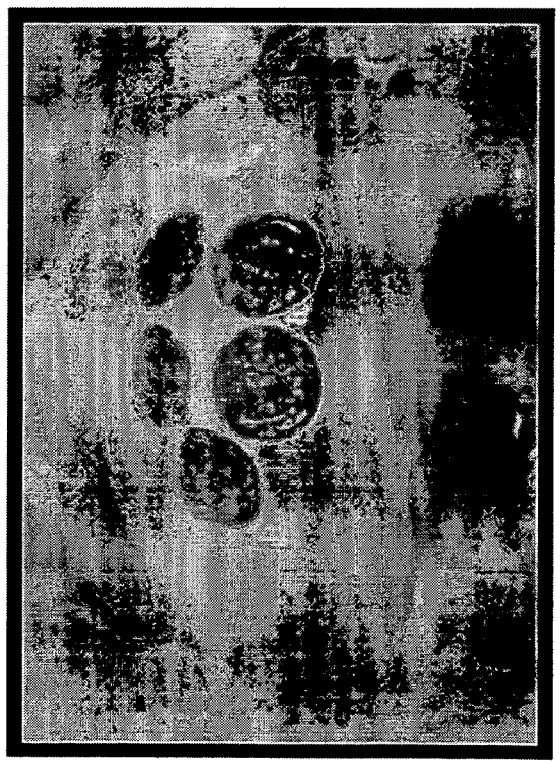

One of the most significant advantages of this chitosan thermogelling formulation for cartilage repair is its ability to conform and adhere to irregular cartilage defects and other irregularly shaped cavities in the body that require tissue repair, regeneration, reconstruction or bulking. Many current tissue repair procedures suffer drastically in this respect. Chitosan-glycerol phosphate liquid gel without cells was delivered ex vivo to porcine femoral condylar intra-chondral (not involving bone) defects. Disc-shaped defects in the articular cartilage were created using a biopsy punch (FIG. 12A) and the chitosan solution described in Example 1 was injected into these defects and allowed to solidify in an incubator at 37° C. The articulating cartilage surface was opposed and simulated joint motions were performed after which the gel was observed to remain in the cartilage defect (FIG. 12B). The gel not only remained in the defect but also adhered to the surrounding bone and cartilage surfaces and did not contract. In FIGS. 12A and 12B, liquid chitosan gel was deposited in 6 mm diameter full-thickness cartilage defects (FIG. 12A) and allowed to solidify at 37° C. for 30 minutes in a humidified incubator. The joint was then closed, and joint motion simulated for several minutes. The chitosan gel adhered to and was retained in all of the defects after simulated joint motion (FIG. 12B).

Figure 13B:
FIGS. 13A and 13B illustrate loading of thermogelling chitosan solution to chondral defects in rabbits, and 24 hours residence in vivo.
Figure 13A:

In vivo filling of intrachondral defects was also performed on the patellar groove of rabbits. A rectangular (4 mm×5 mm) defect was created by shaving off cartilage down to the harder calcified cartilage layer with a microsurgical knife. Several microfracture holes were introduced using a 16-gauge needle, The thermogelling chitosan solution described in Example 1 was injected into this defect and allowed to solidify for 5 minutes (FIG. 13A) and the rabbit knee joint sutured up. The rabbit was allowed to ambulate freely and the following day it was euthanised and the treated knee joint prepared for histological analysis (FIG. 13B). A live New Zealand White rabbit was anesthetized, and a 3×4 mm chondral-only defect created in the trochlea of the femoral patellar groove. Several microfracture holes were introduced with a 16 gauge needle. Liquid thermogelling chitosan was loaded into the defect and allowed to gel for 5 minutes in situ (FIG. 13A). The joint was closed, and the rabbit allowed to recover with unrestricted motion for 24 hours before sacrifice and joint dissection (FIG. 13B).

Figure 14:
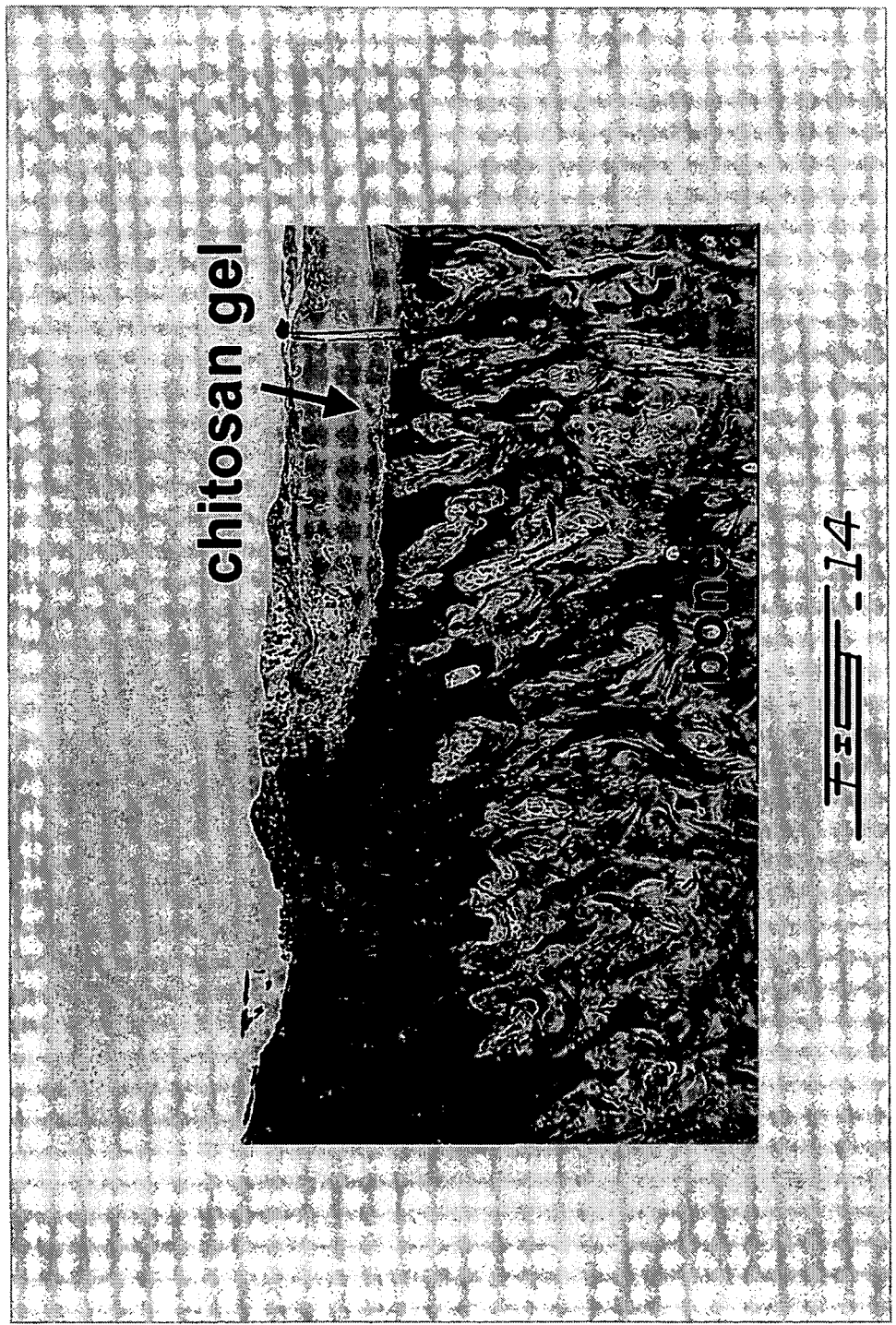
FIG. 14 illustrates the retention of thermogelling chitosan solution in chondral defects in rabbits, 24 hours after injection.

Histological analysis (FIG. 14) revealed the retention of this thermogelling chitosan gel in the very thin cartilage layer of the rabbit (only about 0.8 mm thick). The gel adhered firmly to surrounding bone and cartilage tissue, demonstrating good retention, thereby enabling its use as an injectable thermogelling polymer delivery vehicle for the repair of cartilage and other tissues. The joint and defect shown in FIG. 13B (filled with thermogelling chitosan, and residing 24 hours in vivo) was fixed, embedded in LR White plastic resin, sectioned, and stained with Toluidine Blue. A cross-section of the defect reveals retention of the chitosan gel in situ, as well as adherence to cartilage and bone surfaces in the defect.

EXAMPLE 4

Preparation, Mixing and In Vitro Solidification of Blood/Polymer Mixture

Several distinct mixing methods were employed to admix blood with an aqueous polymer solution (FIG. 15A). Blood and polymer are admixed in a recipient, resulting in a homogenous liquid blend of blood and polymer.

Figure 16:
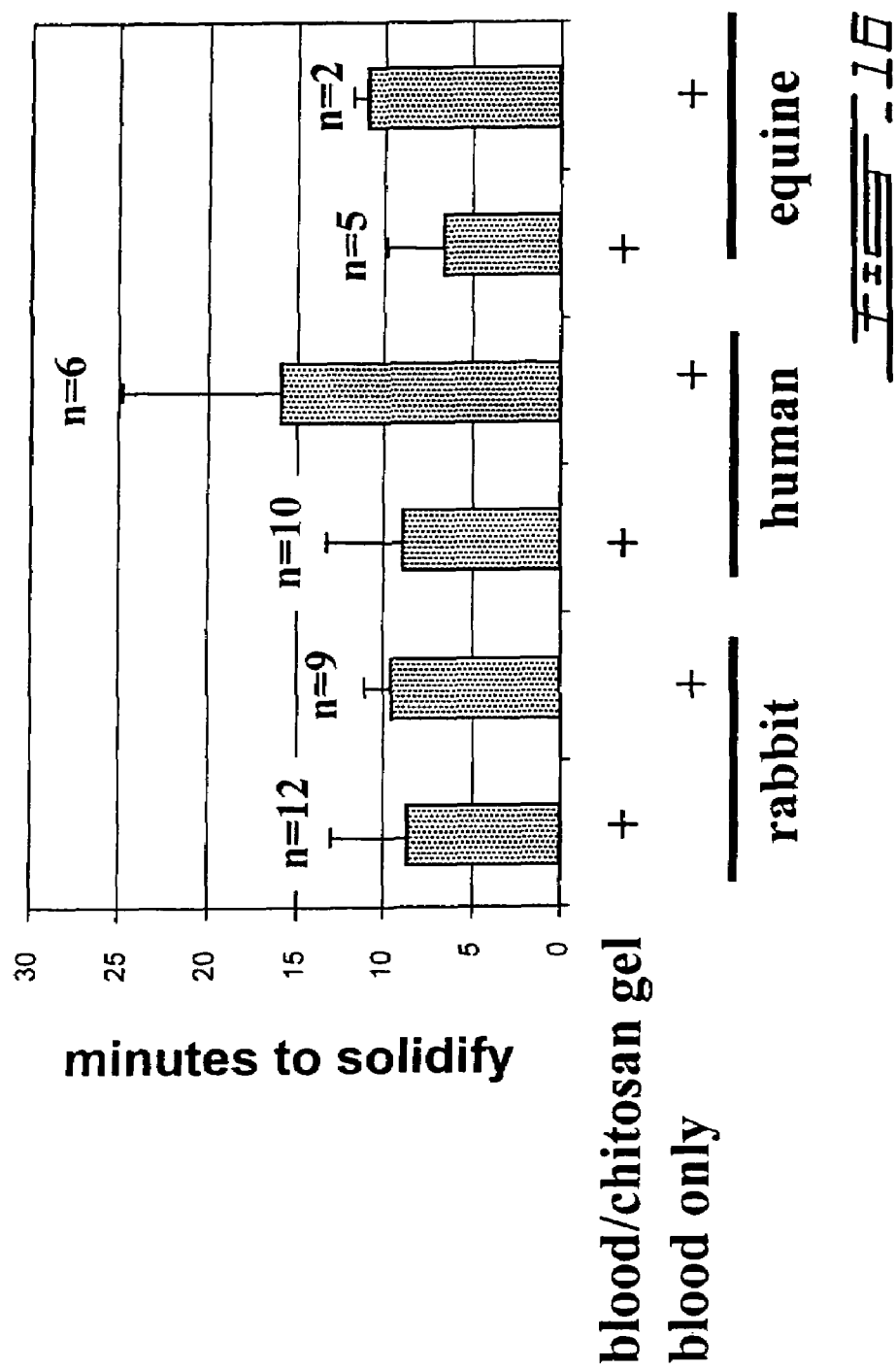
FIG. 16 illustrates an average solidification time of a blood/chitosan mixture versus blood alone using blood from three different species.

In general, 3 volumes blood was mixed with 1 volume of 1.5% polysaccharide in an isotonic and iso-osmolaric solution. In the case of chitosan gel, 1.5% chitosan was dissolved in 70 mM HCl and 135 mM β-glycerol phosphate. In the first blood/polymer mixing method, one, 1 cc syringe was loaded with 750 µl whole peripheral blood, and a second 1 cc syringe was loaded with 250 µl liquid polymer solution. The syringes were interconnected, and mixed by pumping the two phases back-and-forth 40 times, until apparently homogenous. In the second mixing method, 625 µl of liquid polymer solution was deposited in a 2.0 ml cryovial (Corning) with several 3 mm–6 mm steel balls. The cryovial was filled with 1.875 ml whole blood, the cap screwed on, and the vial shaken vigorously for 10 seconds. In the third mixing method, 2 ml of liquid polymer solution was deposited in a sterile 12 ml glass borosilicate vial (InterGlass 5 cc serological vial). The vial closed with a rubber stopper and metal crimper, and a 25 ml air vacuum was drawn in the vial with a 10 ml syringe and 20-gauge needle. Using proper phlebotomy techniques, peripheral blood from either rabbit artery, or human or equine vein was drawn into a sterile 10 ml syringe. A 20-gauge needle was attached to the syringe, and inserted through the rubber stopper of the vial. 6 ml of peripheral blood was admitted to the vial. The vial was vortex mixed for 10 seconds at full speed. Following any of these mixing techniques, the resulting mixture was deposited into a 4 ml borosilicate glass vial at room temperature, a plastic vial at 37° C., or an agarose well (FIGS. 15B and 15C), or an articular cartilage defect ex vivo. As a control, the same treatment was performed with peripheral whole blood only. As another control, a vacutainer vial of EDTA-treated blood was drawn to measure CBC and platelet number. All blood samples tested displayed normal CBC and platelet counts for the respective species. Regardless of the species, the prepared blood/polymer, solidified and adhered strongly to the walls of the glass vial within 2.5 to 18 minutes after mixing (FIG. 16). Mixed whole peripheral blood solidified in general more slowly compared to blood/chitosan gel (FIG. 16). Separate samples of blood, with or without liquid chitosan gel, were mixed and solidification time was measured by the number of minutes elapsed between mixing, and achieving a solid adherent mass in the original mixing vial, or secondary recipient.

Figure 17A:
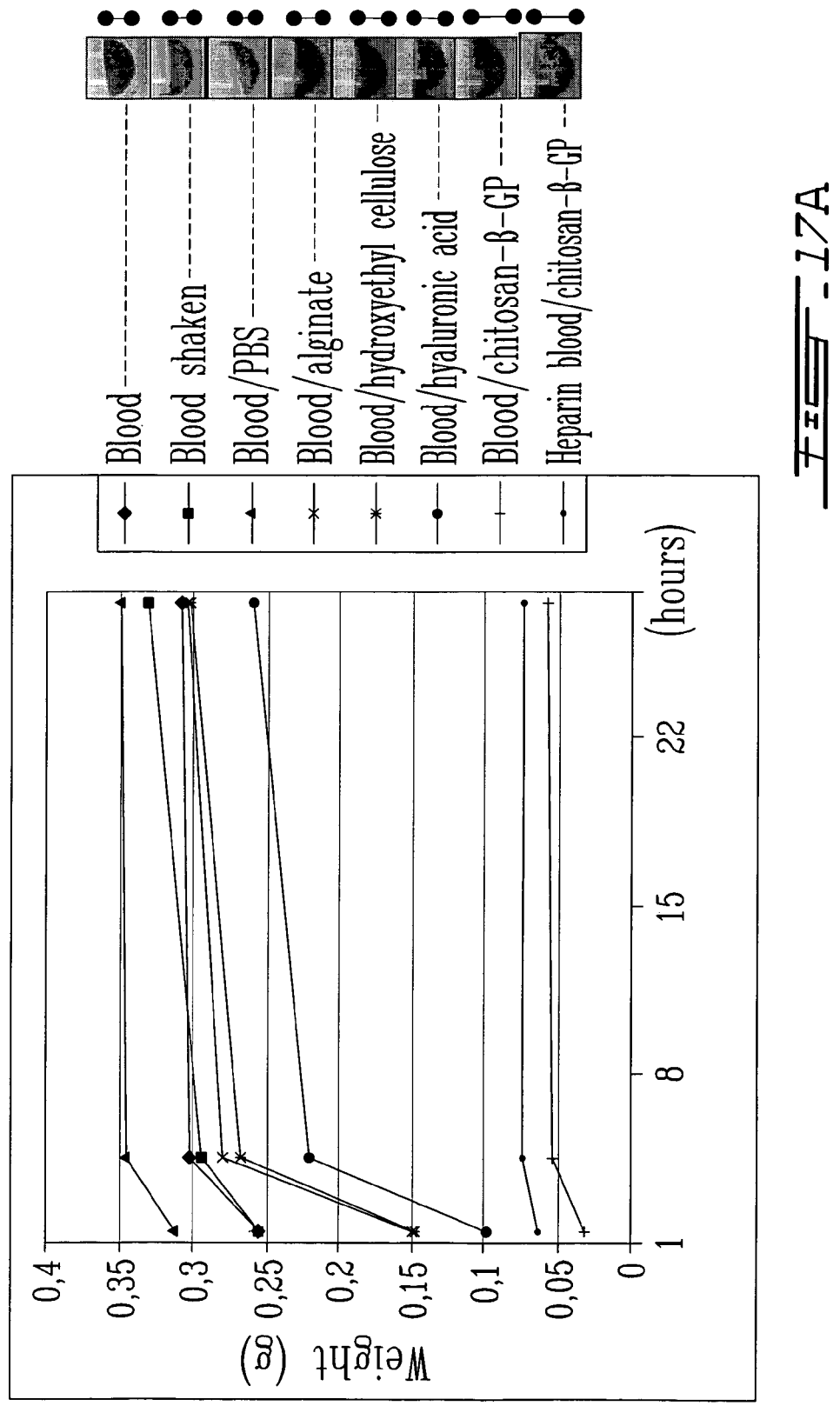
FIG. 17A illustrates a clot contraction of blood, or blood/polymer mixtures, as measured by plasma release with time, after deposition in a glass vial.

Testing of additional blood/polymer solutions, including blood/hyaluronic acid, blood/hydroxyethyl cellulose, and blood/alginate, revealed that these mixtures also solidify in a time period that is comparable to blood alone (FIG. 17A). Here it was concluded that admixture of chitosan liquid gel into whole peripheral blood accelerates clot formation, and that blood/chitosan gel solidification time is acceptable for clinical application. Contraction was tested on mixed fresh peripheral rabbit blood, or rabbit blood mixed with PBS or various 1.5% polysaccharide solutions including chitosan in glycerol phosphate buffer. Fresh blood without mixing was also analyzed. A heparin blood/chitosan in glycerol phosphate buffer mixture was also analyzed. 500 µl of each sample was deposited into a 4 ml glass tube at 37° C. At distinct time points, all excluded plasma was removed from each tube and weighed, to determine the amount of clot contraction. All samples except blood/chitosan glycerol phosphate mixtures contracted to 30–50% of their original volume. Blood/chitosan mixtures contracted minimally maintaining approximately 90% of their initial volume.

Figure 17B:
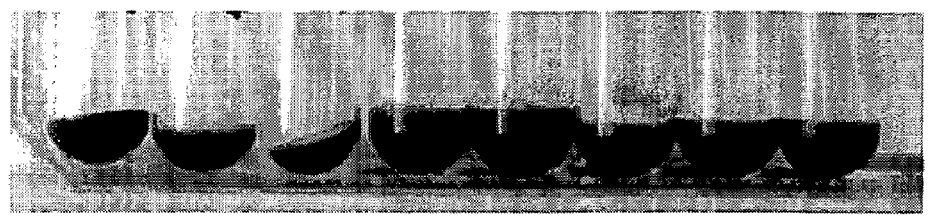
FIGS. 17B and 17C illustrate the physical appearance of solid blood and blood/polymer mixtures, 28 hours post-contraction, in glass tubes (FIG. 17B) or as free-swelling discs cast in agarose wells and incubated in Tyrode's buffer (FIG. 17C)
Figure 17C:

To test for the degree of contraction of solidified blood/polymer mixes relative to coagulated whole blood, a clot contraction test was performed on an array of blood/polymer samples, using several controls (FIGS. 17A, 17B and 17C). One group of controls consisted of non-agitated whole peripheral blood, or agitated whole peripheral blood, or whole peripheral blood agitated 3:1 (volume:volume) with phosphate-buffered saline. These samples were compared with experimental samples containing 3 volumes whole peripheral blood agitated with 1 volume of distinct 1.5% polysaccharide solutions dissolved in PBS (alginate, hydroxyethyl cellulose, or hyaluronic acid). Another sample consisted of 3 volumes whole peripheral blood mixed with 1 volume chitosan-glycerol phosphate solution. At intervals up to 18 hours after solidification, the excluded serum for each condition was measured in triplicate, as an indication of degree of contraction. Samples with peripheral blood, ±PBS, contracted to 30% of the original mass (FIG. 17A). Peripheral blood admixed with the polysaccharides alginate, hydroxyethyl cellulose, or hyaluronic acid contracted to 40%–50% of the original mass (FIG. 17A). The blood/chitosan gel samples showed negligible contraction, with contraction to 90% of the original mass (FIG. 17A). The heparinised blood/chitosan gel samples also resisted contraction, to 85% of the original mass (FIG. 17A). From these data it was concluded that blood/chitosan gel resists contraction, and provides a more space-filling fibrin scaffolding inside the cartilage defect. In FIGS. 17B and 17C, samples shown include blood (1), or mixed blood (2), blood/PBS (3), blood/chitosan in glycerol-phosphate (4), heparin blood/chitosan (S), blood/alginate (6), blood/hydroxyethyl cellulose (7), and blood/hyaluronic acid (8).

Figure 18:
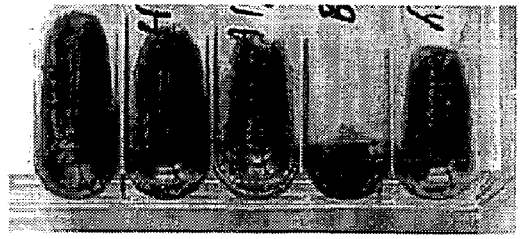
FIG. 18 illustrates an admixture of liquid chitosan, but not other liquid polysaccharide solutions, reversing heparin-mediated anti-coagulation.

To test whether anti-coagulated blood could be used to generate blood/polysaccharide in situ solidifying implants, 3 volumes of blood treated with 1.5 mM EDTA, 0.38% citrate, acid-0.38% citrate dextrose, or sodium heparin (Becton Dickinson) was mixed with 1 volume chitosan-glycerol phosphate solution. Chitosan-glycerol-phosphate solution was able to reverse heparin- (FIG. 18), EDTA-, and citrate-mediated anti-coagulation. 1.5% chitosan in glycerol-phosphate solution, or three distinct 1.5% polysaccharide solutions, were admixed at a ratio of 1 volume polysaccharide solution, to 3 parts whole peripheral blood. 500 µl of each sample was deposited in a glass borosilicate tube and allowed to solidify for 60 minutes at 37° C. Different polysaccharides include hyaluronic acid-PBS (1), hydroxyethyl cellulose-PBS (2), alginate-PBS (3), and chitosan-glycerol phosphate (4). As a control, heparin blood only was analyzed (5). After 60 minutes, the tubes were laid horizontally and photodocumented. Only the mixture of chitosan-glycerol phosphate and heparinised blood became solid. Other heparin blood/polysaccharide mixtures using hydroxyethyl cellulose, alginate, or hyaluronic acid, failed to solidify (FIG. 18). From these data it was concluded that blood/chitosan in situ solidifying implants can be generated using anti-coagulated blood.

Figures 19A, 19B, 19C:
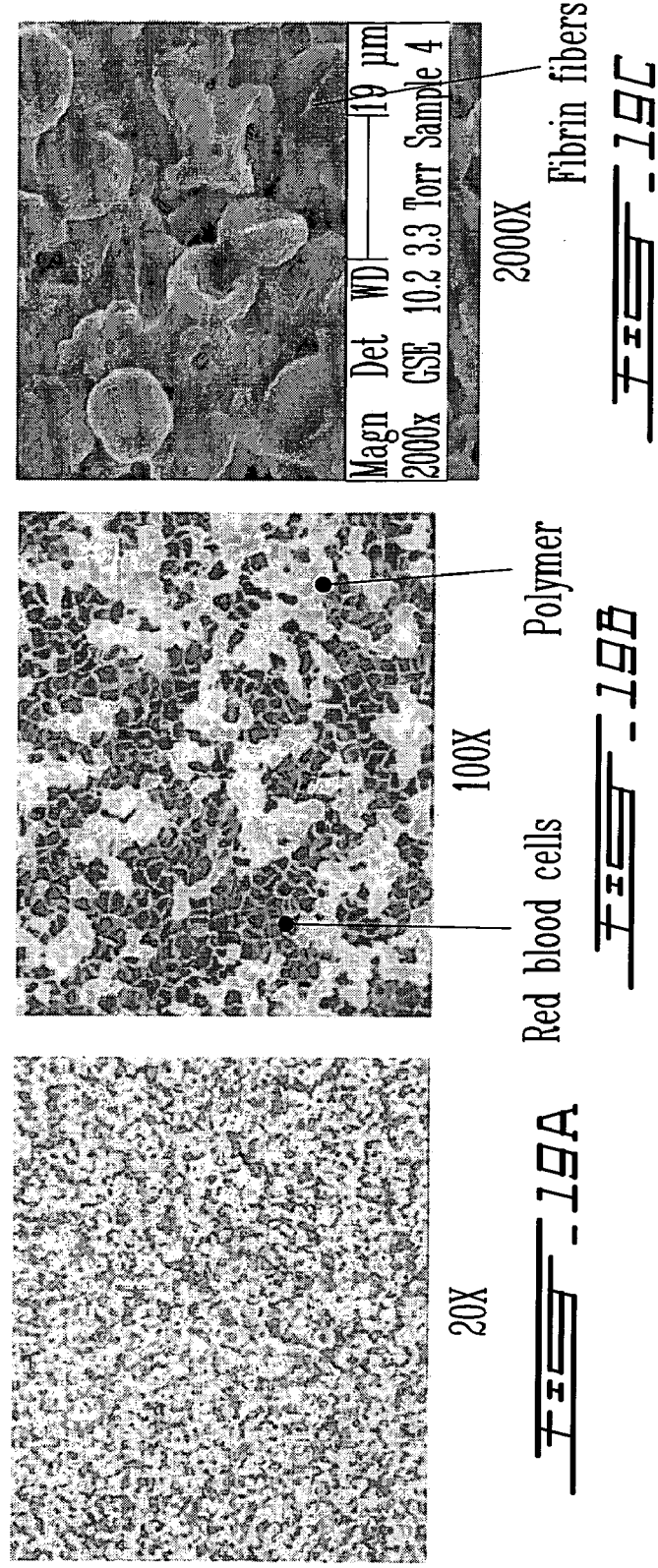
FIGS. 19A to 19C illustrate an histology of blood/polymer mixture.

Histological sections of solid blood/polymer samples showed that mixtures were homogenous, that red blood cells did not hemolyse after mixing or solidification, and that platelets became activated and were functional (as evidenced by the generation of a dense fibrin network) (FIGS. 19A to 19C). A solidified mixture of blood/chitosan was fixed, embedded in LR White plastic, sectioned, and stained with Toluidine Blue. (In FIG. 19A, at 20× magnification, global homogeneous mixing is apparent. In FIG. 19B, at 100× magnification, intermixed pools of red blood cells and chitosan hydropolymer is apparent. At 2000× magnification (by environmental electron scanning microscopy) the presence of fibrin fiber network throughout the blood/chitosan composite is evident.

Figure 20B:
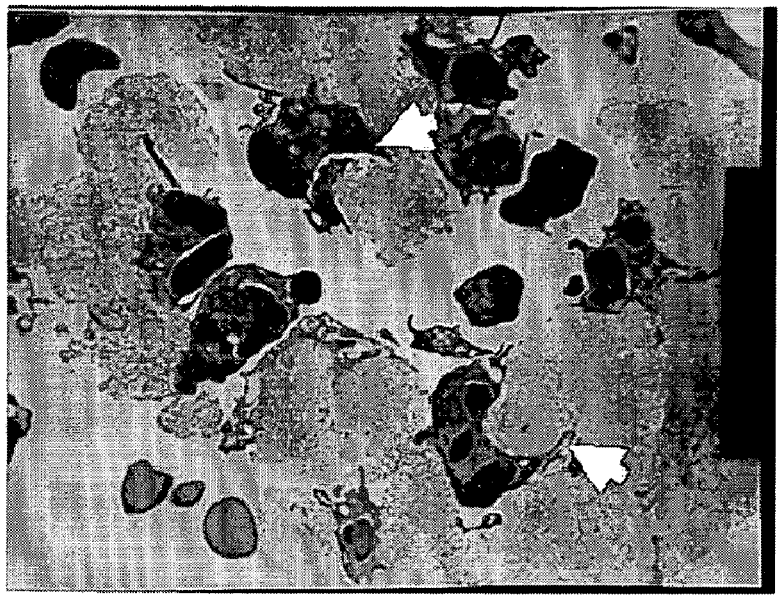
FIGS. 20A and 20B illustrates viability of leukocytes and platelets after mixing with a chitosan solution.
Figure 20A:
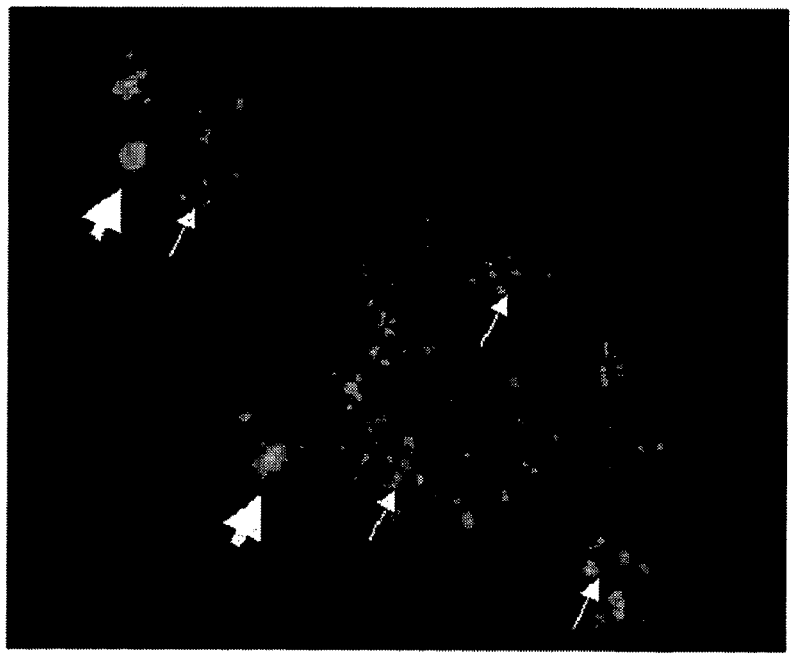

Some leukocytes remained viable a number of hours following mixing and solidification (FIG. 20). Peripheral whole blood was mixed with chitosan gel and allowed to solidify. In FIG. 20A, 60 minutes post-solidification, the plug was placed in viability stain with calcein AM/ethidium homodimer-1 to reveal live white blood cells (green cells, large arrows), live platelets (green cells, small arrows), and dead white blood cells (red nuclei). In FIG. 20B, a distinct sample was fixed at 180 minutes post-solidification, embedded in LR-White, and submitted to Transmission Electron Microscopy. Active phagocytosis by peripheral monocytes (arrow head), reflecting cell viability, is evident in TEM micrographs at 3 hours post-mixing and solidification.

An analysis of the total serum proteins lost from either blood or blood/chitosan following solidification was performed. Equal volumes of blood, or blood/chitosan gel were solidified in agarose wells. The discs were transferred to individual wells of a 48-well plate containing 1 ml PBS and incubated at 37° C. for 3 hours. The discs were successively changed into fresh PBS solution at 37° C. at 4, 5, 7, and 19 hours. PBS washes were lightly centrifuged to remove any cells prior to analysis. Several discs were extracted for total protein after 3 or 19 hours in PBS. Total proteins present in the discs, or PBS washes, were analysed by SDS-PAGE and total protein stain with Sypro Orange. Serum proteins were released more slowly more sustained from the blood/chitosan samples compared with blood samples (FIG. 21). These data suggest that blood and platelet-derived proteins involved in wound healing are released in a more sustained and prolonged manner from blood/chitosan-filled defects, compared with blood clot-filled defects. Solid discs of blood/chitosan gel, or blood only, were generated from 150 µl initial liquid volume. Resulting discs were washed in 1 ml PBS for 3 hours, then transferred successively at 4, 5, 7, and 19 hours for a total of four additional 1 ml PBS washes. After 3 or 19 hours of washing, representative discs were extracted with GuCl to solubilise total retained proteins. Soluble proteins were precipitated from equal volumes of GuCl extracts or PBS washes, separated on SDS-PAGE gels, and stained for total proteins using Sypro Orange. Comparatively, more proteins were retained in the blood/polymer discs than the blood discs throughout the 19 hour wash period. Comparatively, a slower and more prolonged release of serum proteins into the PBS washes was seen for blood/chitosan than blood over the 19 hour wash period.

EXAMPLE 5

Preparation, Mixing and Injection of Blood/Polymer Mixture to Improve Healing of Articular Cartilage Defects Chondral defects with perforations to the subchondral bone were treated with a peripheral blood/chitosan-glycerol phosphate mixture that was delivered as a liquid, and allowed to solidify in situ (FIGS. 22A to 22C). In FIG. 22A, a full-thickness cartilage defect, 3×4 mm square, was created in the femoral patellar groove of an adult (more than 7 months) New Zealand White rabbit. Four, 1 mm diameter microdrill holes were pierced to the bone, until bleeding was observed. In FIG. 22B, liquid whole blood was mixed at a ratio of 3 volumes blood to 1 volume chitosan in glycerol phosphate solution, and deposited to fill the defect. In FIG. 22C, after 5 minutes in situ, the blood/chitosan implant appeared to solidify. The capsule and skin were sutured, and the animal allowed to recover with unrestricted motion.

A similar treatment in human patients is schematized in FIG. 22D, where prepared cartilage defects receive an arthroscopic injection of liquid blood/polymer that solidifies in situ. Alternatively, an arthroscopic injection of liquid polymer is mixed with bone-derived blood at the defect site (FIG. 22E). In FIG. 22D, the patient blood is mixed with the polymer ex vivo, and delivered to a prepared defect by arthroscopic injection, or (FIG. 22E) the polymer is delivered arthroscopically or during open knee surgery and mixed at the defect site with patient blood issuing from the defect.

As a proof-of-concept study, the effects of blood/chitosan gel treatment were tested in rabbits. Adult, skeletally mature New Zealand White rabbits (7 months and older) were anesthetized, with xylazine-ketamine followed by isofluorene/oxygen gas anesthesia. The trochlea of the femoral patellar groove was exposed by a parapatellar incision and patellar displacement. A full-thickness cartilage defect, up to 4×5 mm, in the trochlea of the femoral patellar groove, was produced with a microsurgical knife. Four, 4 mm deep, 1 mm diameter bone-penetrating holes were generated by either microdrill with constant irrigation with 4° C. PBS, or by puncture with a custom-made awl and hammer. The defect was flushed with PBS, and depending on the degree of bleeding, up to 200 µl of sterile epinephrine (2 µg/ml) in phosphate buffered saline was injected into the bleeding holes. The cartilage defect was covered with a sterile gauze soaked with PBS. Rabbit peripheral blood was removed from the central artery of the ear with a vacutainer™ needle and untreated, siliconized glass 4 cc vacutainer™ vials from Becton Dickison.

In one treatment, 750 µl blood was drawn into a sterile 1 cc syringe. A second syringe holding 250 µl of chitosan-glycerol phosphate solution (1.5% chitosan/70 mM HCl/135 mM β-glycerol phosphate) was interconnected with the blood-containing syringe with a sterile plastic connector. The syringes were pumped back-and-forth 40 times. The mix was drawn into one syringe, to which a 20-gauge needle was attached. After purging half of the mix, one drop (about 25 µl) was deposited into the defect. In a separate treatment, 2 ml blood was added to a polypropylene cryovial tube containing 667 µl 1.5% chitosan/70 mM HCl/135 mM β-glycerol phosphate and 6 sterile 3.2 mm diameter stainless steel beads. The tube was capped, and shaken for 10 seconds, rigorously (around 40 to 50 actions). The resulting liquid blood/chitosan mix was removed from the vial with a sterile 1 cc syringe, and a 20 g needle was attached to the syringe. After purging 200 µl from the syringe, one drop (about 25 µl) was deposited to fill the cartilage defect. The blood/chitosan mixture was allowed to solidify for 5 minutes, after which the capsule and skin were sutured, and the wound disinfected. Rabbits were sacrificed at 1 week (n=1, male) or at 51 or 56 days (n=2, 1 male, 1 female). Joints were fixed, decalcified, embedded in LR/White plastic, sectioned, and stained with Toluidine Blue. Blood/chitosan-treated defects at 1 week of healing revealed large numbers of chemotactic cells migrating towards the blood/chitosan-filled zone (FIG. 23A). Untreated defects had a relatively weak chemotactic response (FIG. 23B) towards the blood clot at the top of the defect. A chondral defect with microdrill holes was created in both femoral patellar grooves of an adult New Zealand White rabbit, one of which was filled with blood/chitosan gel, and another left untreated. One week after healing, the joints were fixed, processed in LR-White, and Toluidine blue stained. At 2 to 3 mm below the surface of the cartilage, a large number of cells migrating towards the defect filled with blood/chitosan were evident (FIG. 23A), whereas fewer migrating cells were seen at the same region of the untreated defect (FIG. 23B).

Figure 24B:
FIGS. 24A and 24B illustrate the growth of hyaline cartilage in defects treated with a blood/polymer mixture versus growth of fibrotic tissue in untreated defects.
Figure 24A:
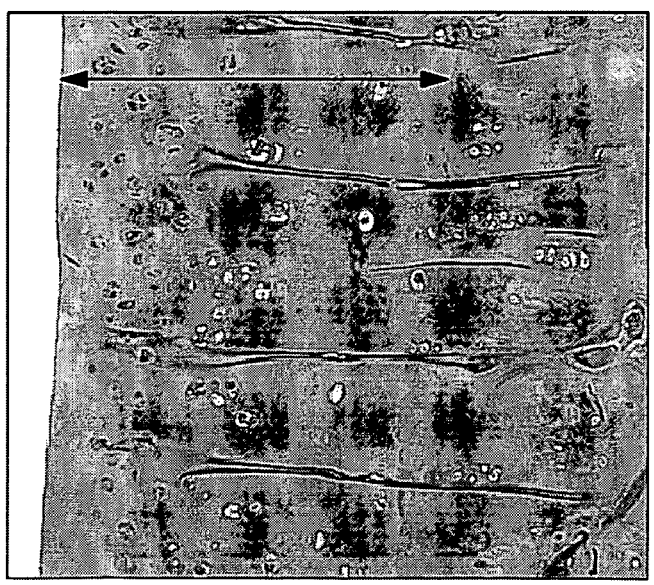

After 5 to 8 weeks healing, the blood/chitosan-treated defect was filled with hyaline repair tissue in 2 rabbits (1 male, 1 female)(FIG. 24A). This blood/chitosan-based repair tissue had the appearance of hyaline, GAG-rich cartilage repair tissue. The repair tissue from untreated, or blood-only treated microfracture defects, had the appearance of fibrocartilage (FIG. 24B). There was no histological evidence of blood/chitosan or blood clot persisting within the defect site at or beyond 3 weeks post-delivery. A chondral defect with microdrill holes was created in both femoral patellar grooves of an adult New Zealand White rabbit, one of which was filled with blood/chitosan gel, and another left untreated. At 51 or 56 days after healing, the joints were fixed, processed in LR-White, and Toluidine blue stained. In FIG. 24A, repair tissue from the blood/chitosan-treated defect had the appearance of metachromatically staining hyaline cartilage, which adhered to the defect surfaces, and filled the defect. In FIG. 24B, repair tissue from the untreated defect had the appearance of fibrocartilage, with practically no metachromatic staining for GAG, and only partial defect filling.

While the invention has been described with particular reference to the illustrated embodiments, it will be understood that numerous modifications thereto will appear to those skilled in the art. Accordingly, the above description and accompanying drawings should be taken as illustrative of the invention and not in a limiting sense. For example, we have demonstrated that mixing chitosan in solution with blood allows the formation of polymer/blood clot that does not contract significantly, demonstrates a slowed release of chemotactic and mitogenic blood proteins, maintenance of blood cell viability, and a dramatically improved repair of articular cartilage defects. It is obvious to those skilled in the art that the chitosan solution could be prepared differently to achieve the same result. Examples include: 1) altered chitosan concentration and mixing ratio with blood 2) altered choice of aqueous solution by changing buffer type and species concentration 3) an aqueous suspension of chitosan aggregates 4) a particulate chitosan powder combined with a proper mixing technique to distribute these particle throughout the blood and partly dissolve them. Other polymers may be used such as 1) another polysaccharide like hyaluronan if its anti-coagulant effect is overcome by formulating it in a procoagulating state (such as by using a low concentration or combining it with thrombin) and 2) a protein polymer such as polylysine or collagen could be used to achieve similar effects. Although it is not believed that these latter approaches will be as successful as our preferred embodiment, due to immunogenicity, toxicity, and cell adhesion/contraction effects, these and other formulations are considered part of the present invention since they possess the characteristics of the polymer preparation of the present invention being that 1) it is mixable with blood or selected components of blood, 2) that the resulting mixture is injectable or can be placed at or in a body site that requires tissue repair, regeneration, reconstruction or bulking and 3) that the mixture has a beneficial effect on the repair, regeneration, reconstruction or bulking of tissue at the site of placement.

REFERENCES

Arnoczky, S. P., R. F. Warren, and J. M. Spivak. 1988. Meniscal repair using an exogenous fibrin clot. An experimental study in dogs. J Bone Joint Surg Am 70, no. 8: 1209–17.

Aston, J. E., and G. Bentley. 1986. Repair of articular surfaces by allografts of articular and growth-plate cartilage. Journal of Bone & Joint Surgery—British Volume 68-B, no. 1: 29–35.

Ateshian, G. A. 1997. A theoretical formulation for boundary friction in articular cartilage. Journal of Biomechanical Engineering 119, no. 1: 81–86.

Austin, P. R., C. J. Brine, J. E. Castle, and J. P. Zikakis. 1981. Chitin: New facets of research. Science 212, no. 4496: 749–53.

Atkinson, B., inventor. 24 Aug. 2000. "Device and method for regeneration and repair of cartilage lesions." Sulzer Biologics, assignee. WO Patent 00/48550.

Bartone, F. F, E. D. Adickes, 1988, Chitosan: effects on wound healing in urogenital tissue: preliminary report: J Urol, v. 140, p. 1134–7.

Bentley, G., and R. B. Greer. 1971. Homotransplantation of isolated epiphyseal and articular cartilage chondrocytes into joint surfaces of rabbits. Nature 230: 385–8.

Bernkop-Schnurch, A., and M. Pasta. 1998. Intestinal peptide and protein delivery—novel bioadhesive drug-carrier matrix shielding from enzymatic attack. Journal of Pharmaceutical Sciences 87, no. 4: 430–434

Braden, M., S. Downes, M. P. Patel, and K. W. M. Davy, inventors. 21 Nov. 1995. "Biomaterials for tissue repair." U.S. Pat. No. 5,468,787.

Breinan, H. A., T. Minas, H. P. Hsu, S. Nehrer, C. B. Sledge, and M. Spector. 1997. Effect of cultured autologous chondrocytes on repair of chondral defects in a canine model. Journal of Bone & Joint Surgery—American Volume 79, no. 10: 1439–51, Breinan, H. A., S. D. Martin, H. P. Hsu, and M. Spector. 2000. Healing of canine articular cartilage defects treated with microfracture, a type-II collagen matrix, or cultured autologous chondrocytes. J Orthop Res 18, no. 5: 781–9.

Brekke, J. H., and R. D. Coutts, inventors. 21 Dec. 1999. "Method and device for reconstruction of articular cartilage." THM Biomedicals, assignee. U.S. Pat. No. 6,005,161.

Brittberg, M., A. Lindahl, G. Homminga, A. Nilsson, O. Isaksson, and L. Peterson. 1997. A critical analysis of cartilage repair. Acta Orthopaedica Scandinavica 68, no. 2: 186–91.

Brittberg, M., A. Lindahl, A. Nilsson, C. Ohlsson, O. Isaksson, and L. Peterson. 1994. Treatment of Deep Cartilage Defects in the Knee with Autologous Chondrocyte Transplantation. N. Engl. J. Med. 331, no. 14: 889–95.

Brittberg, M., A. Nilsson, A. Lindahl, C. Ohlsson, and L. Peterson. 1996. Rabbit articular cartilage defects treated with autologous cultured chondrocytes. Clinical Orthopaedics & Related Research, no. 326: 270–83.

Buckwalter, J. A., and H. J. Mankin. 1997. Articular cartilage 0.2. Degeneration and osteoarthrosis, repair, regeneration, and transplantation (review). Journal of Bone & Joint Surgery—American Volume 79A, no. 4: 612–32.

Buschmann, M. D., Y. A. Gluzband, A. J. Grodzinsky, J. H. Kimura, and E. B. Hunziker. 1992. Chondrocytes in agarose culture synthesize a mechanically functional extracellular matrix. Journal of Orthopaedic Research 10, no. 6: 745–58.

Butnariu-Ephrat, M., D. Robinson, D. G. Mendes, N. Halperin, and Z. Nevo. 1996. Resurfacing of goat articular cartilage by chondrocytes derived from bone marrow. Clinical Orthopaedics & Related Research, no. 330: 234–43.

Caplan, A. I., M. Elyaderani, Y. Mochizuki, S. Wakitani, and V. M. Goldberg. 1997. Principles of cartilage repair and regeneration. Clinical Orthopaedics & Related Research, no. 342: 254–69.

Caplan, A. I., D. J. Fink, and R. G. Young, inventors. 5 Jan. 1999. "Biomatrix for soft tissue regeneration." U.S. Pat. No. 5,855,619.

Caplan, A. I., and S. E. Haynesworth, inventors. 22 Sep. 1998. "Connective tissue regeneration using human mesenchymal stem cell preparations." U.S. Pat. No. 5,811,094.

Carreno-Gomez, B., and R. Duncan. 1997. Evaluation of the biological properties of soluble chitosan and chitosan microspheres. Intl J of Pharmaceutics 148: 231–40.

Chenite, A., C. Chaput, C. Combes, F. Jalal, A. Selmani. Temperature-controlled pH-dependent formation of ionic polysaccharide gels. WO Patent 99/07416.

Chenite, A., C. Chaput, D. Wang, C. Combes, M. D. Buschmann, C. D. Hoemann, J. C. Leroux, B. L. Atkinson, F. Binette, and A. Selmani. 2000. Novel injectable neutral solutions of chitosan form biodegradable gels in situ. *Biomaterials* 21, no. 21: 2155–61.

Chesterman, P. J., and A. U. Smith. 1968. Homotransplantation of articular cartilage and isolated chondrocytes. An experimental study in rabbits. Journal of Bone & Joint Surgery—British Volume 50, no. 1: 184–97.

Childers, J. C. Jr, and S. C. Ellwood. 1979. Partial chondrectomy and subchondral bone drilling for chondromalacia. *Clin Orthop*, no. 144: 114–20.

Cho, Y. W., Y. N. Cho, S. H. Chung, G. Yoo, S. W. Ko, 1999, Water-soluble chitin as a wound healing accelerator: Biomaterials, v. 20, p. 2139–45.

Chu, C. R., R. D. Coutts, M. Yoshioka, F. L. Harwood, A. Z. Monosov, and D. Amiel. 1995. Articular cartilage repair using allogeneic perichondrocyte-seeded biodegradable porous polylactic acid (PLA): a tissue-engineering study. Journal of Biomedical Materials Research 29, no. 9: 1147–54.

Chu, C. R., J. S. Dounchis, M. Yoshioka, R. L. Sah, R. D. Coutts, and D. Amiel. 1997. Osteochondral repair using perichondrial cells, A 1-year study in rabbits. Clinical Orthopaedics & Related Research, no. 340: 220–9.

Clark, Richard A. F. 1996. *The molecular and cellular biology of wound repair.* 2 ed. New York; Plenum.

Cochrum, K. C., H. R. Parker, and M. M. C. Chu, inventors. 30 Jun. 1998. "Fibrogen/Chitosan hemostatic agents." The Regents of the University of California, assignee. U.S. Pat. No. 5,773,033.

Cohen, I., J. Gabbay, T. Glaser, and A. Oplatka. 1975. "Fibrin-blood platelet interaction in a contracting clot." Br J Haematol 31, no. 1: 45–50.

Collombel, C., O. Damour, C. Gagnieu, F. Poisignon, C. Echinard, and J. Marichy, inventors. 24 Nov. 1992. "Biomaterials with a base of mixtures of collagen, chitosan and glycosaminoglycans process for preparing them and their application in human medicine." Centre National de la Recherche, assignee. U.S. Pat. No. 5,166,187.

Denuziere, A., D. Ferrier, O. Damour, and A. Domard. 1998. Chitosan-chondroitin sulfate and chitosan-hyaluronate polyelectrolyte complexes: biological properties. Biomaterials 19, no. 14: 1275–85.

Depalma, A. F., C. D. McKeever, and D. K. Subin. 1966. Process of repair of articular cartilage demonstrated by histology and autoradiography with tritiated thymidine. Clinical Orthopaedics & Related Research 48: 229–42.

Dillon, G. P., X. Yu, A. Sridharan, J. P. Ranieri, and R. V. Bellamkonda. 1998. The Influence of Physical Structure and Charge on neurite Extension in a 3D Hydrogel Scaffold. Journal of Biomaterials Science Polymer Edition 9, no. 10: 1049–69.

Drohan, W. N., M. J. MacPhee, S. I. Miekka, S. S. Manish, Clive Elson, and John R. Taylor, inventors. 26 Sep. 2000. "Chitin hydrogels, methods of their production and use." Inc. Chitogenics, The American National Red Cross, and Coalition for Hemophilia, assignees. U.S. Pat. No. 6,124,273.

Dunn, A. R., and S. L. Dunn, inventors. 29 Nov. 1994. "Method of regenerating articular cartilage." U.S. Pat. No. 5,368,051.

Eser, E. A., Y. M. Elcin, and G. D. Pappas. 1998. Neural Tissue Engineering; Adrenalin Chromaffin Cell Attachment and Viability on Chitosan Scaffolds. Neurological Research 20: 648–54.

Frankel, S. R., B. Toolan, D. Menche, M. I. Pitman, and J. M. Pachence. 1997. Chondrocyte transplantation using a collagen bilayer matrix for cartilage repair. J. Bone Joint Surg. 79-B, no. 5: 831–36.

Freed, L. E., D. A. Grande, Z. Lingbin, J. Emmanual, J. C. Marquis, and R. Langer. 1994. Joint resurfacing using allograft chondrocytes and synthetic biodegradable polymer scaffolds. Journal of Biomedical Materials Research 28, no. 8: 891–9.

Fukamizo, T., and R. Brzezinski. 1997. Chitosanase from *streptomyces* sp. Strain n174—a comparative review of its structure and function (review). Biochemistry and Cell Biology-Biochimie Et Biologie Cellulaire 75, no. 6: 687–96.

Gouda, I., and O. Larm, inventors. 11 May 1999. "Method of promoting dermal wound healing with chitosan and heparin or heparin sulfate." Medicarb, assignee. U.S. Pat. No. 5,902,798.

Grande, D. A., and P. A. Lucas, inventors. 25 May 1999. "Mesenchymal stem cells for cartilage repair." Morphogen Pharmaceuticals Inc., and North Shore University Hospital Research Corp., assignees. U.S. Pat. No. 5,906,934.

Grande, D. A., M. I. Pitman, L. Peterson, D. Menche, and M. Klein. 1989. The repair of experimentally produced defects in rabbit articular cartilage by autologous chondrocyte transplantation. J. Orthop. Res. 7, no. 2: 208–18.

Green, W. T. 1977. Articular cartilage repair. Behavior of rabbit chondrocytes during tissue culture and subsequent allografting. Clinical Orthopaedics & Related Research, no. 124: 237–50.

Griffith-Cima, L., A. Atala, C. A. Vacanti, and K. T. Paige, inventors. 20 Jan. 1998. "Tissue formation by injecting a cell-polymeric solution that gels in vivo." M.I.T., assignee. U.S. Pat. No. 5,709,854.

Halvorsen, Y-D. C., W. O. Wilkison, and J. Gimble, inventors. 21 Feb. 2001. "Use of adipose tissue-derived stromal cells for chondrocyte differentiation and cartilage repair." EP Patent 1,077,253

Hall, B. K. 1983. Cartilage. New York, N.Y.: Academic Press.

Halpern, A. A., inventor. 12 Aug. 1997. "Method for cartilage repair."U.S. Pat. No. 5,655,546.

Hangody, L., G. Kish, Z. Karpati, I. Szerb, and I. Udvarhelyi. 1997. Arthroscopic autogenous osteochondral mosaicplasty for the treatment of femoral condylar articular defects. A preliminary report. *Knee Surg Sports Traumatol Arthrosc* 5, no. 4: 262–7.

Hangody, L., G. Kish, Z. Karpati, I. Szerb, and R. Eberhardt. 1997. Treatment of osteochondritis dissecans of the talus: use of the mosaicplasty technique—a preliminary report. *Foot Ankle Int* 18, no. 10: 628–34

Hansson, H-A., G. Johasson-Ruden, and O. Larm, inventors. 13 Apr. 1999. "Hard Tissue stimulating agent." Astra Akiebolag, assignee. U.S. Pat. No. 5,894,070.

Hendrickson, D. A., A. J. Nixon, D. A. Grande, R. J. Todhunter, R. M. Minor, H. Erb, and G. Lust. 1994. Chondrocyte-fibrin matrix transplants for resurfacing extensive articular cartilage defects. Journal of Orthopaedic Research 12, no. 4: 485–97.

Higaki, H., T. Murakami, and Y. Nakanishi. 1997. Lubricating ability of langmuir-blodgett films as boundary lubricating films on articular surfaces. JSME International Journal Series C-Mechanical Systems Machine Elements & Manufacturing 40, no. 4: 776–81.

Homminga, G. N., S. K. Bulstra, R. Kuijer, and A. J. van der Linden. 1991. Repair of sheep articular cartilage defects with a rabbit costal perichondrial graft. Acta Orthopaedica Scandinavica 62, no. 5.415–6.

Hunziker, E. B., and L. C. Rosenberg. 1996. Repair of partial-thickness defects in articular cartialge—cell recruitment from the synovial membrane. Journal of Bone & Joint Surgery—American Volume 78A, no. 5: 721–33.

Hyc, A., J. Malejczyk, A. Osiecka, and S. Moskalewski. 1997. Immunological response against allogeneic chondrocytes transplanted into joint surface defects in rats. Cell Transplantation 6, no. 2: 119–24.

Insall, J. N. 1967. Intra-articular surgery for degenerative arthritis of the knee. A report of the work of the late K. H. Pridie. *J Bone Joint Surg Br* 49, no. 2: 211–28.

Inui, H., M. TsujLkubo, S. Hirano, 1995, Low molecular weight chitosan stimulation of mitogenic response to platelet-derived growth factor in vascular smooth muscle cells: Biosci Biotechnol Biochem, v. 59, p. 2111–4.

Itay, S., A. Abramovici, and Z. Nevo. 1987. Use of cultured embryonal chick epiphyseal chondrocytes as grafts for defects in chick articular cartilage. Clinical Orthopaedics & Related Research, no. 220: 284–303.

Johnson, L. L., 1991. Arthroscopic abrasion arthroplasty. In *Operative arthroscopy*. McGinty, J. B. (Ed.) et al., 341–60. New York: Raven.

Johnstone, B., and J. Yoo, inventors. 1 Jun. 1999. "In vitro chondrogenic induction of human mesenchymal stem cells." Case Western Reserve University, assignee. U.S. Pat. No. 5,908,784.

Jorgensen, T., J. Moss, and H. Nicolajsen, inventors. 28 May 1998. "A method for promoting tissue repair." Dumex-Alpharma, assignee. WO Patent 98/22114.

Jurgensen, K., D. Aeschlimann, V. Cavin, M. Genge, and E. B. Hunziker. 1997. A new biological glue for cartilage-cartilage interfaces—tissue transglutaminase. Journal of Bone & Joint Surgery—American Volume 79A, no. 2: 185–93.

Kandel, R. A., H. Chen, J. Clark, and R. Renlund. 1995. Transplantation of cartilaginous tissue generated in vitro into articular joint defects. Art. Cells, Blood subs., and Immob. Biotech. 23, no. 5: 565–77.

Kawamura, S., S. Wakitani; T. Kimura, A. Maeda, A. I. Caplan, K. Shino, and T. Ochi. 1998. Articular cartilage repair. Rabbit experiments with a collagen gel-biomatrix and chondrocytes cultured in it. Acta Orthopaedica Scandinavica 69, no. 1: 56–62.

Koyano, T., N. Minoura, M. Nagura, and K. Kobayashi. 1998. Attachment and growth of cultures fibroblast cells on pva/chitosan-blended hydrogels. Journal of Biomedical Materials Research 39, no. 3: 486–90.

Kuettner, K. E. 1992. Biochemistry of articular cartilage in health and disease. Clin Biochem 25, no. 3: 155–63.

Lahiji, A, A Sohrabi, D S Hungerford, C G Frondoza, 2000, Chitosan supports the expression of extracellular matrix proteins in human osteoblasts and chondrocytes: J Biomed Mater Res, v. 51, p. 586–95.

Lee, K. Y., I. C. Kwon, Y. H. Kim, W, H. Jo, and S. Y. Jeong. 1998. Preparation of chitosan self-aggregates as a gene delivery system. Journal of Controlled Release 51, no. 2–3: 213–20.

Lee, Y M, Y J Park, S J Lee, Y Ku, S B Han, S M Choi, P R Klokkevold, C P Chung, 2000, Tissue engineered bone formation using chitosan/tricalcium phosphate sponges: J Periodontol, v. 71, p. 410–7.

Lu, J. X., F. Prudhommeaux, A. Meunier, L. Sedel, and G. Guillemin. 1999. Effects of chitosan on rat knee cartilages. *Biomaterials* 20, no. 20: 1937–44.

Mahomed, M. N., R. J. Beaver, and A. E. Gross. 1992. The long-term success of fresh, small fragment osteochondral allografts used for intraarticular post-traumatic defects in the knee joint. Orthopedics (Thorofare, N.J.) 15, no. 10: 1191–9.

Malette, W. G., H. J. Quigley, R. D. Gaines, N. D. Johnson, w, G. Rainer, 1983, Chitosan: a new hemostatic: Ann Thorac Surg, v. 36, p. 55–8.

Malette, W. G., and H. J. Quigley, inventors. 19 Jul. 1983. "Method of acheving hemostasis." U.S. Pat. No. 4,394,373.

Malette, W. G., and H. J. Quigley, inventors. 30 Jul. 1985. "Method of achieving hemostasis, inhibiting fibroplasia, and promoting tissue regeneration in tissue wound." U.S. Pat. No. 4,532,134.

Mankin, H. J. 1974. The reaction of articular cartilage to injury and osteoarthritis (first of two parts). *N Engl J Med* 291, no. 24: 1285–92.

1974. The reaction of articular cartilage to injury and osteoarthritis (second of two parts). *N Engl J Med* 291, no. 25: 1335–40.

Mattioli-Belmonte, M., A. Gigante, R. A. Muzzarelli, R. Politano, A. De Benedittis, N. Specchia, A. Buffa, G. Biagini, F. Greco, 1999, N,N-dicarboxymethyl chitosan as delivery agent for bone morphogenetic protein in the repair of articular cartilage: Med Biol Eng Comput, v. 37, p. 130–4.

McCarty, Daniel J, and William J Koopman. 1993. Arthritis and allied conditions. A textbook of rheumatology. Philadelphia: Lea and Febiger.

Messner, K., and J. Gillquist. 1996. Cartilage repair—a critical review (review). Acta Orthopaedica Scandinavica 67, no. 5: 523–29.

Minas, T., and S. Nehrer. 1997. Current concepts in the treatment of articular cartilage defects. (Review) (41 refs). Orthopedics (Thorofare, N.J.) 20, no. 6: 525–38.

Mosbey, D. T., inventor. 11 Sep. 1990. "Wound filling composition." Minnesota Mining and Manufacturing Company, assignee. U.S. Pat. No. 4,956,350.

Mueller, W., and T. Thaler, inventors. 17 Nov. 1998. "Process for regenerating bone and cartilage." Sulzer Medizinaltechnik A G., assignee. U.S. Pat. No. 5,837,235.

Muzzarelli, R. A. A., and G. Biagini. 1993. Role and fate of exogenous chitosans in human wound tissues. Chitin Enzymology: 187–96.

Muzzarelli, R. A. A., W. S. Xia, M. Tomasetti, and P. Ilari. 1995. Depolymerization of chitosan and substituted chitosans with the aid of a wheat germ lipase preparation. Enzyme & Microbial Technology 17, no. 6: 541–45.

Muzzarelli, R. A., M. Mattioli-Belmonte, C. Tietz, R. Biagini, G. Perioli, M. A. Brunelli, M. Fini, R. Giardino, P. Ilari, and G. Biagini. 1994. Stimulatory effect on bone formation exerted by a modified chitosan. Biomaterials 15, no. 13: 1075–81.

Namba, R. S., M. Meuli, K. M. Sullivan, A. X. Le, and N. S. Adzick. 1998. Spontaneous repair of superficial defects in articular cartilage in a fetal lamb model. Journal of Bone & Joint Surgery—American Volume 80A, no. 1: 4–10.

Naughton, C. K., and B. A. Naughton, inventors. 28 Jul. 1998. "Three-dimensional genetically engineered cell and tissue culture system." U.S. Pat. No. 5,785,964.

Naughton, G. K., and J. Willoughby, inventors. 1 Dec. 1998. "Method for repairing cartilage." U.S. Pat. No. 5,842,477.

Nevo, Z., D. Robinson, S. Horowitz, A. Hasharoni, and A. Yayon. 1998. The manipulated mesenchymal stem cells in regenerated skeletal tissues. Cell Transplantation 7, no. 1: 63–70.

Newman, A. P. 1998. Articular cartilage repair. American Journal of Sports Medicine 26, no. 2: 309–24.

Nixon, A. J., L. A. Fortier, J. Williams, and H. Mohammed. 1999. Enhanced repair of extensive articular defects by insulin-like growth factor-1-laden fibrin composites. *J Orthop Res* 17, no. 4: 475–87.

Noguchi, T., M. Oka, M. Fujino, M. Neo, and T. Yamamuro. 1994. Repair of osteochondral defects with grafts of cultured chondrocytes. Comparison of allografts and isografts. Clinical Orthopaedics & Related Research, no. 302: 251–8.

O'Driscoll, S. W., F. W. Keeley, and R. B. Salter. 1988. Durability of regenerated articular cartilage produced by free autogenous periosteal grafts in major full-thickness defects in joint surfaces under the influence of continuous passive motion. A follow-up report at one year. Journal of Bone & Joint Surgery—American Volume 70, no. 4: 595–606.

O'Driscoll, S. W., A. D. Recklies, and A. R. Poole. 1994. Chondrogenesis in periosteal explants. An organ culture model for in vitro study. Journal of Bone & Joint Surgery—American Volume 76, no. 7: 1042–51.

Okamoto, Y, K Shibazaki, S Minami, A Matsuhashi, S Tanioka, Y Shigemasa, 1995, Evaluation of chitin and chitosan on open would healing in dogs: J Vet Med Sci, v. 57, p. 851–4.

Outerbridge, H. K., A. R. Outerbridge, and R. E. Outerbridge. 1995. The use of a lateral patellar autologous graft for the repair of a large osteochondral defect in the knee. Journal of Bone & Joint Surgery—American Volume 77, no. 1: 65–72.

Pachence, J. M., S. Frenkel, and D. Menche, inventors. 27 Jun. 2000. "Multi-stage collagen-based template or implant for use in the repair of cartialge lesions." Hospital for Joint Disease Orthopaedic institute, assignee. U.S. Pat. No. 6,080,194

Paletta, G. A., S. P. Arnoczky, and R. F. Warren. 1992. The repair of osteochondral defects using an exogenous fibrin clot. An experimental study in dogs. *Am J Sports Med* 20, no. 6: 725–31.

Pechak, D. G., M. J. Kujawa, and A. I. Caplan. 1986. Morphology of bone development and bone remodeling in embryonic chick limbs. Bone 7, no. 6: 459–72.

Peluso, G., O. Petillo, M. Ranieri, M. Santin, L. Ambrosio, D. Calabro, B. Avallone, G. Balsamo, 1994, Chitosan-mediated stimulation of macrophage function: Biomaterials, v. 15, p. 1215–20.

Peterson, D. R. and N. Nousek-Goebl. 13 Mar. 2001. "Isolation of precursor cells from hematopoietic and non-hematopoietic tissues and their use in vivo bone and cartilage regeneration". DePuy Orthopaedics, assignee. U.S. Pat. No. 6,200,606.

Pridie, K. H., A method of resurfacing osteoarthritic knee joints. 1959. In Proceedings of the British Orthopaedic Association. J. Bone and Joint Surg. 41-B: 618–619

Purchio, A. F., M. Zimber, N. Dunkelman, G. K. Naughton, and B. A. Naughton, inventors. 11 May 1999. "Three-dimensional cartilage cultures." Advanced Tissue Sciences Inc., assignee. U.S. Pat. No. 5,902,741.

Rao, S. B., C. P. Sharma, 1997, Use of chitosan as a biomaterial: studies on its safety and hemostatic potential: J Biomed Mater Res, v. 34, p. 21–8

Robinson, D., N. Halperin, and Z. Nevo. 1990. Regenerating hyaline cartilage in articular defects of old chickens using implants of embryonal chick chondrocytes embedded in a new natural delivery substance. Calcif. Tissue Int. 46, no. 4: 246–53.

Rodgers, K., and G. Dizerega, inventors. 20 Jan. 2000. "Methods for accelerating bone and cartilage growth and repair." University of Southern California, assignee. WO Patent 00/02905.

Rodrigo, J. J., J. R. Steadman, and J. P. Sillima. 1993. Osteoarticular injuries of the knee. *Operative orthopaedics*. Second edition ed., 2077–82.

Sackier, J. M., C. B. Wood, R. Krishnan, G. R. Wiggington, and D. M. H. Butler, inventors, 18 Mar. 1997. "Method of regenerating or replacing cartilage tissue using amniotic cells." Genethics Limited, assignee. U.S. Pat. No. 5,612,028

Sall, K. N., J. K. Kreter, R. H. Keates, 1987, The effect of chitosan on corneal wound healing: Ann Ophthalmol, v. 19, p. 31–3.

Sams, A. E., and A. J. Nixon. 1995. Chondrocyte-laden collagen scaffolds for resurfacing extensive articular cartilage defects. Osteoarthritis & Cartilage 3, no. 1: 47–59.

Sashiwa, H., H. Saimoto, Y. Shigemasa, R. Ogawa, and S. Tokura. 1990. Lysozyme susceptibility of partially deacetylated chitin. International Journal of Biological Macromolecules 12, no. 5: 295–6.

Schipper, N. G. M., S. Olsson, J. A. Hoogstraate, A. G. Deboer, K. M. Varum, and P. Artursson. 1997. Chitosans as absorption enhancers for poorly absorbable drugs 0.2. Mechanism of absorption enhancement. Pharmaceutical Research 14, no. 7: 923–29.

Schwartz, R. E., inventor. 12 May 1998. "Cartilage repair unit and method of assembling same." Matrix Biotechnologies Inc., assignee. U.S. Pat. No. 5,749,874.

Schwarz, I. M., and B. A. Hills. 1998. Surface-active phospholipid as the lubricating component of lubricin. British Journal of Rheumatology 37, no. 1: 21–26.

Sechriest, V. F., Y. J. Miao, C. Niyibizi, A. Westerhausen-Larson, H. W. Matthew, C. H. Evans, F. H. Fu, and J. K. Suh. 2000. GAG-augmented polysaccharide hydrogel: a novel biocompatible and biodegradable material to support chondrogenesis. *J Biomed Mater Res* 49, no. 4: 534–41.

Sellers, R. S., D. Peluso, and E. A. Morris. 1997. The effect of recombinant human bone morphogenetic protein-2 (rhBMP-2) on the healing of full-thickness defects of articular cartilage. Journal of Bone & Joint Surgery—American Volume 79, no. 10: 1452–63.

Sellers, R. S., R. Zhang, S. S. Glasson, H. D. Kim, D. Peluso, D. A. D'Augusta, K. Beckwith, and E. A. Morris. 2000. Repair of articular cartilage defects one year after treatment with recombinant human bone morphogenetic protein-2 (rhBMP-2). *J Bone Joint Surg Am* 82, no. 2: 151–60.

Shigemasa, Y., and S. Minami. 1996. Applications of chitin and chitosan for biomaterials. *Biotechnol Genet Eng Rev* 13: 383–420.

Soulhat, J, M. D. Buschmann, and A. Shirazi-Adl. 1999. A fibril-network reinforced biphasic model of cartilage in unconfined compression. Journal of Biomechanical Engineering 121, no. 3: 340–7.

Sparkes, B. G., and D. G. Murray, inventors. 25 Feb. 1986. "Chitosan based wound dressing materials." Her Majesty the Queen in right of Canada, assignee. U.S. Pat. No. 4,572,906.

Specchia, N., A. Gigante, F. Falciglia, and F. Greco. 1996. Fetal chondral homografts in the repair of articular cartilage defects. Bulletin—Hospital for Joint Diseases 54, no. 4: 230–5.

Steadman, J. R., W. G. Rodkey, K. K. Briggs, and J. J. Rodrigo. 1998. The microfracture procedure: Rationale, technique, and clinical observations for treatment of articular cartilage defects. *J. Sports Traumatol. Rel. Res.* 20, no. 2: 61–70.

Stone, C. A., H. Wright, T. Clarke, R. Powell, V. S. Devaraj, 2000, Healing at skin graft donor sites dressed with chitosan: Br J Plast Surg, v. 53, p. 601–6.

Stone, K. R., inventor. 29 Aug. 2000. "Method and paste for articular cartilage transplatation." U.S. Pat. No. 6,110,209.

Suh, J., H. Matthew, P. Fu, and F. Fu, inventors. 23 Sep. 1999. "Chitosan-based composite materials containing glycosaminoglycan for cartilage repair." University of Pittburg, assignee. WO Patent 99/47186.

Suh, J. K., H. W. Matthew, 2000, Application of chitosan-based polysaccharide biomaterials in cartilage tissue engineering: a review: Biomaterials, v. 21, p. 2589–98.

Terbojevich, M., A. Cosani, and R. A. A. Muzzarelli. 1996. Molecular parameters of chitosans depolymerized with the aid of papain. Carbohydrate Polymers 29, no. 1: 63–68.

Tubo, R. A., L. M. Barone, and C. A. Wrenn, inventors. 3 Mar. 1998. "Methods and compositions for the repair of articular cartilage defects in mammals." Genzyme Corp., assignee. U.S. Pat. No. 5,723,331.

Ueno, H., H. Yamada, I. Tanaka, N. Kaba, M. Matsuura, M. Okumura, T. Kadosawa, T. Fujinaga, 1999, Accelerating effects of chitosan for healing at early phase of experimental open wound in dogs: Biomaterials, v. 20, p. 1407–14.

Vacanti, J. P., and R. S. Langer, inventors. 23 June 1998a. "Preparation of three-dimensional fibrous scaffold for attaching cells to produce vascularized tissue in vivo." U.S. Pat. No. 5,770,193.

Vacanti, J. P., and R. S. Langer, inventors. 23 Jun. 1998b. "Three-dimensional fibrous scaffold containing attached cells for producing vascularized tissue in vivo." U.S. Pat. No. 5,770,417.

Vacanti, J. P., C. A. Vacanti, and R. S. Langer, inventors. 7 Apr. 1998. "Biodegradable synthetic polymeric fibrous matrix containing chondrocyte for in vivo production of a cartilaginous structure." M.I.T., and Children's Medical Center Corp., assignees. U.S. Pat. No. 5,736,372.

Vasios, G. W., P. D. DiBenedetto, C. A. Preston, R. A. Tubo, and J. M. McPherson. 1999. Chitotriosidase is expressed in normal chondrocytes and is upregulated in chondrocytes derived from osteoarthritic cartilage. 45th Annual Meeting, Orthopaedic Research Society.

Villeneuve, P. E., inventor. 2 Feb. 1999. "Materials for healing cartilage and bone defects." U.S. Pat. No. 5,866,415.

Wakitani, S., T. Kimura, A. Hirooka, T. Ochi, M. Yoneda, H. Owaki, K. Ono, and N. Yasui. 1989. Repair of rabbit articular surfaces with allografts of chondrocytes embedded in collagen gels. Nippon Seikeigeka Gakkai Zasshi—Journal of the Japanese Orthopaedic Association 63, no. 5: 529–38.

Wakitani, S., T. Goto, S. J. Pineda, R. G. Young, J. M. Mansour, A. I. Caplan, and V. M. Goldberg. 1994. Mesenchymal cell-based repair of large, full-thickness defects of articular cartilage. *J Bone Joint Surg Am* 76, no. 4: 579–92.

Wei, X., J. Gao, and K. Messner. 1997. Maturation-dependent repair of untreated osteochondral defects in the rabbit knee joint. Journal of Biomedical Materials Research 34, no. 1: 63–72.

Yagi, K., N. Michibayashi, N. Kurikawa, Y. Nakashima, T. Mizoguchi, A. Harada, S. Higashiyama, H. Muranaka, and M. Kawase. 1997. Effectiveness of fructose-modified chitosan as a scaffold for hepatocyte attachment. Biological & Pharmaceutical Bulletin 20, no. 12: 1290–4.

Yalpani, M., and D. Pantaleone. 1994. An examination of the unusual susceptibility of aminoglycans to enzymatic hydrolysis. Carbohydrate Research 256, no. 1: 159–75.

Zhang, R., E. Morris, and D. Peluso, inventors. 3 Aug. 2000. "Methods and compositions for healing and repair of articular cartilage." Inc. Genetics Institute, assignee. WO Patent 00/44413.

The invention claimed is:

1. A method for repair and/or regeneration in cartilaginous tissue comprising administering at a site of the cartilaginous tissue in need of repair an effective amount of a polymer composition comprising:
   a solution of a polymer; and
   blood,
   wherein the polymer includes at least one selected from the group consisting of a polysaccharide, a protein, and a polyamino acid, and further wherein when the polymer is combined with blood the polymer composition is converted into a non-liquid state in time or upon heating such that the polymer compositions when placed at the site in need of repair, the polymer composition will adhere to the site in need of repair to effect reconstruction or bulking of the tissue and/or regeneration thereof.

2. The method of claim 1, wherein the polysaccharide is a modified or natural polysaccharide.

3. The method of claim 2, wherein the polysaccharide is selected from the group consisting of chitosan, chitin, hyaluronan, glycosaminoglycan, chondroitin sulfate, keratan sulfate, dermatan sulfate, heparin, and heparin sulfate.

4. The method of claim 1, wherein the polysaccharide is chitosan.

5. The method of claim 1, wherein cartilaginous tissue is selected from the group consisting of cartilage, meniscus, ligament and tendon.

6. The method of claim 1, wherein the protein is a natural, recombinant or synthetic protein.

7. The method of claim 3, wherein said protein is a polyamino acid.

8. The method of claim 7, wherein the polyamino acid is a polylysine.

9. The method of claim 6, wherein the natural protein is soluble collagen or gelatin.

10. The method of claim 1, wherein the polymer composition is dissolved or suspended in a buffer containing organic or inorganic salts.

11. The method of claim 10, wherein the inorganic salts are selected from the group consisting of sodium chloride or phosphates, sulfates or carboxylates of potassium, calcium and magnesium.

12. The method of claim 1, wherein said polymer composition has a pH between 6.5 and 7.8.

13. The method of claim 1, wherein said polymer solution has an osmolarity adjusted to a physiological value between 250 mOsm/L and 600 mOsm/L.

14. The method of claim 1, wherein the blood is anticoagulated.

15. The method of claim 1, wherein the blood further comprises an anticoagulant selected from the group consisting of citrate, heparin or EDTA.

16. The method of claim 1, wherein the blood further comprises a pro-coagulant to improve coagulation/solidification at the site of introduction.

17. The method of claim 1, wherein the pro-coagulant is selected from the group consisting of thrombin, calcium, collagen, ellagic acid, epinephrine, adenosine diphosphate, tissue factor, a phospholipid, and a coagulation factor.

18. The method of claim 1, wherein the blood is autologous or non-autologous.

19. The method of claim 18, wherein the blood is free of at least one of erythrocytes and/or leukocytes.

20. The method of claim 18, wherein the blood is enriched in platelets.

21. The method of claim 1, wherein the polymer composition is used in a ratio varying from 1:100 to 100:1 with respect to the blood.

22. The method of claim 1, wherein said polymer and blood are mechanically mixed using sound waves, stirring, vortexing, or multiple passes in syringes.

23. The method of claim 10, wherein the organic salts are selected from the group consisting of glycerol-phosphate, fructose phosphate, glucose phosphate, L-serine phosphate, adenosine phosphate, glucosamine, galactosamine, HEPES, PIPES and MES.

24. The method of claim 1, wherein the blood is selected from the group consisting of whole blood, processed blood, venous blood, arterial blood, blood from bone-marrow, umbilical cord blood and placenta blood.

25. The method of claim 17, wherein the coagulation factor is factor VII.

26. The method of claim 4, wherein the chitosan is dissolved in an organic or inorganic phosphate buffer.

27. The method of claim 26, wherein the organic or inorganic phosphate buffer is a phosphate or glycerol phosphate containing buffer.

28. The method of claim 26, wherein the chitosan in the composition is in a soluble state, said composition having a pH between 6.5 and 7.4.

29. The method of claim 1, wherein the cartilaginous tissue is selected from the group consisting of articular cartilage, nose cartilage, ear cartilage, meniscus and avascular cartilage.

30. A method for repair and/or regeneration in cartilaginous tissue comprising administering at a site of the cartilaginous tissue in need of repair an effective amount of a thermogelling composition comprising:
a solution of the polymer chitosan;
glycerol phosphate; and
blood,
wherein the thermogelling composition is converted into a non-liquid state in time or upon heating, said composition once converted into a non-liquid state adheres to the site in need of repair when placed thereon to effect reconstruction or bulking of the tissue and/or regeneration thereof.

31. The method of claim 30, wherein cartilaginous tissue is selected from the group consisting of cartilage, meniscus, ligament and tendon.

32. The method of claim 30, wherein said polymer composition has a pH between 6.5 and 7.8, and wherein said chitosan is in solution at said pH.

33. The method of claim 30, wherein said polymer solution has an osmolarity adjusted to a physiological value between 250 mOsm/L and 600 mOsm/L.

34. The method of claim 30, wherein the blood is anticoagulated.

35. The method of claim 30, wherein the blood further comprises an anticoagulant selected from the group consisting of citrate, heparin or EDTA.

36. The method of claim 30, wherein the blood further comprises a pro-coagulant to improve coagulation/solidification at the site of introduction.

37. The method of claim 30, wherein the pro-coagulant is selected from the group consisting of thrombin, calcium, collagen, ellagic acid, epinephrine, adenosine diphosphate, tissue factor, a phospholipid, and a coagulation factor.

38. The method of claim 30, wherein the blood is autologous or non-autologous.

39. The method of claim 38, wherein the blood is free of at least one of erythrocytes and/or leukocytes.

40. The method of claim 38, wherein the blood is enriched in platelets.

41. The method of claim 30, wherein said chitosan, glycerol phosphate and blood are mechanically mixed using sound waves, stirring, vortexing, or multiple passes in syringes.

42. The method of claim 30, wherein the blood is selected from the group consisting of whole blood, processed blood, venous blood, arterial blood, blood from bone-marrow, umbilical cord blood and placenta blood.

43. The method of claim 37, wherein the coagulation factor is factor VII.

44. The method of claim 30, wherein the cartilaginous tissue is selected from the group consisting of articular cartilage, nose cartilage, ear cartilage, meniscus and avascular cartilage.

* * * * *

UNITED STATES PATENT AND TRADEMARK OFFICE
CERTIFICATE OF CORRECTION

PATENT NO. : 7,148,209 B2  
APPLICATION NO. : 11/031325  
DATED : December 12, 2006  
INVENTOR(S) : Hoemann et al.

Page 1 of 1

It is certified that error appears in the above-identified patent and that said Letters Patent is hereby corrected as shown below:

On title page, item 73 Assignee, replace

"Ecole Polytechnique, Montreal (CA)" with

-- Bio Syntech Canada Inc. --.

Signed and Sealed this

Twelfth Day of February, 2008

JON W. DUDAS  
*Director of the United States Patent and Trademark Office*